(12) United States Patent
Dai et al.

(10) Patent No.: US 7,799,829 B2
(45) Date of Patent: *Sep. 21, 2010

(54) ACYLOXYALKYL CARBAMATE PRODRUGS OF α-AMINO ACIDS, METHODS OF SYNTHESIS AND USE

(75) Inventors: Xuedong Dai, San Jose, CA (US); Archana Gangakhedkar, San Jose, CA (US); Jia-Ning Xiang, Palo Alto, CA (US); Mark A Gallop, Los Altos, CA (US)

(73) Assignee: XenoPort, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/416,823

(22) Filed: Apr. 1, 2009

(65) Prior Publication Data

US 2009/0192225 A1 Jul. 30, 2009

Related U.S. Application Data

(63) Continuation of application No. 11/878,661, filed on Jul. 26, 2007, now Pat. No. 7,531,572.

(60) Provisional application No. 60/833,774, filed on Jul. 28, 2006.

(51) Int. Cl.
*A61K 31/27* (2006.01)
*C07C 69/74* (2006.01)

(52) U.S. Cl. ........................... 514/484; 560/124
(58) Field of Classification Search ................ None
See application file for complete search history.

(56) References Cited

U.S. PATENT DOCUMENTS

| | | | |
|---|---|---|---|
| 4,426,391 A | 1/1984 | Alexander et al. | |
| 4,760,057 A | 7/1988 | Alexander | |
| 5,086,072 A | 2/1992 | Trullas et al. | |
| 5,401,868 A | 3/1995 | Lund | |
| 5,428,069 A | 6/1995 | Skolnick et al. | |
| 5,523,323 A | 6/1996 | Maccecchini | |
| 5,607,691 A | 3/1997 | Hale et al. | |
| 5,672,584 A | 9/1997 | Borchardt et al. | |
| 5,837,730 A | 11/1998 | Javitt | |
| 5,854,286 A | 12/1998 | Javitt et al. | |
| 6,017,957 A | 1/2000 | Skolnick et al. | |
| 6,162,827 A | 12/2000 | Javitt | |
| 6,355,681 B2 | 3/2002 | Javitt | |
| 6,361,957 B1 | 3/2002 | Javitt | |
| 6,667,297 B2 | 12/2003 | Tsai et al. | |
| 6,927,036 B2 | 8/2005 | Gallop et al. | |
| 6,974,821 B2 | 12/2005 | Tsai et al. | |
| 7,227,028 B2 | 6/2007 | Gallop et al. | |
| 7,232,924 B2 | 6/2007 | Raillard et al. | |
| 7,531,572 B2 * | 5/2009 | Dai et al. ............... | 514/476 |
| 2002/0010212 A1 | 1/2002 | Javitt | |
| 2002/0013364 A1 | 1/2002 | Javitt | |
| 2002/0035145 A1 | 3/2002 | Tsai et al. | |
| 2002/0161048 A1 | 10/2002 | Javitt | |
| 2002/0183390 A1 | 12/2002 | Javitt | |
| 2002/0193429 A1 | 12/2002 | Tsai et al. | |
| 2004/0014940 A1 | 1/2004 | Raillard et al. | |
| 2004/0087596 A1 | 5/2004 | Schneider | |
| 2004/0092530 A1 | 5/2004 | Tsai et al. | |
| 2004/0208923 A1 | 10/2004 | Davis et al. | |
| 2005/0070715 A1 | 3/2005 | Bhat et al. | |
| 2005/0096396 A1 | 5/2005 | Davis et al. | |
| 2005/0159488 A1 | 7/2005 | Javitt | |
| 2005/0222431 A1 | 10/2005 | Gallop et al. | |
| 2005/0250851 A1 | 11/2005 | Tsai et al. | |

FOREIGN PATENT DOCUMENTS

| | | |
|---|---|---|
| EP | 0 416 689 B1 | 11/1995 |
| WO | WO 93/25197 A1 | 12/1993 |
| WO | WO 01/05813 A1 | 1/2001 |
| WO | WO 02/085928 A2 | 10/2002 |
| WO | WO 2005/066122 A2 | 7/2005 |

OTHER PUBLICATIONS

Andersen et al., "Spatial Memory Deficits Induced by Perinatal Treatment of Rats with PCP and Reversal Effect of D-Serine," *Neuropsychopharmacology* Natue Publishing Group (2004) 29, 1080-1090.

Bennett et al., "Modulation of striatal dopamine release in vitro by agonists of the glycine$_B$ site of NMDA receptors; interaction with antipsychotics," *European Journal of Pharmacology* (2005) 527, 52-59, www.sciencedirect.com.

Diagnostic and Statistical Manual of Mental Disorders (DSM-IV-TR, Fourth Edition, Text Revision, American Psychiatric Association, Arlington, VA (2000).

Goff et al., "Dose-Finding Trial of D-Cycloserine Added to Neuroleptics for Negative Symptoms in Schizophrenia," *American Journal of Psychiatry* (1995) 152:8, 1213-1215.

Goff et al., "A Placebo-Controlled Trial of D-Cycloserine Added to Conventional Neuroleptics in Patients with Schizophrenia," *Archives of General Psychiatry* (1999), 56:1, 21-27.

Heresco-Levy et al., "Double-Blind, Placebo-Controlled, Crossover Trial of Glycine Adjuvant Therapy for Treatment-Resistant Schizophrenia," *British Journal of Psychiatry* 1996, 169, 610-617.

(Continued)

*Primary Examiner*—Paul A Zucker
(74) *Attorney, Agent, or Firm*—Finnegan, Henderson, Farabow, Garrett & Dunner, LLP

(57) ABSTRACT

Acyloxyalkyl carbamate prodrugs of α-amino acids, pharmaceutical compositions thereof, methods of making acyloxyalkyl carbamate prodrugs of α-amino acids and methods of using acyloxyalkyl carbamate prodrugs of α-amino acids, and pharmaceutical compositions thereof to treat a disease are disclosed. Acyloxyalkyl carbamate prodrugs of α-amino acids suitable for oral administration using sustained release dosage forms are also disclosed.

24 Claims, No Drawings

OTHER PUBLICATIONS

Heresco-Levy et al., "Efficacy of High-Dose Glycine in the Treatment of Enduring Negative Symptoms of Schizophrenia," *Archives of General Psychiatry* (1999) 56, 29-36.

Heresco-Levy et al., "Placebo-Controlled Trial of D-Cycloserine Added to Conventional Neuroleptics, Olanzapine, or Risperidone in Schizophrecia," *America Journal Psychiatry* (2002) 159, 480-482.

Javitt, D.C. & Zukin, S.R., "Recent Advances in the Phencyclidine Model of Schizophrenia," *American Journal of Psychiatry* (1991), 148:10, 1301-1308.

Javitt et al., "Amelioration of Negative Symptoms in Schizophrenia by Glycine," *American Journal of Psychiatry* (1994), 151:8, 1234-1236.

Javitt, "Management of Negative Symptoms of Schizophrenia," *Current Psychiatry Rep* (2001) 3, 413-417.

Javitt, "Glycine modulators in schizophrenia," *Current Opinion in Investigational Drugs* (2002), 3(7), 1067-72.

Lane et al., "Sarcosine or D-Serine Add-on Treatment for Acute Exacerbation of Schizophrenia," *Archives of General Psychiatry* (2005) 62, 1196-1204.

Millan, "N-Methyl-D-aspartate receptors as a target for improved antipsychotic agents: novel insights and clinical perspectives," *Psychopharmacology (Berl.)* (2005) 179(1), 30-53.

Mulvihill et al., "Benzaldehyde-derived chloroformates and their application towards the synthesis of methoxyfenozide-N-[(acyloxy)benzyloxy]carbonyl derivatives," *Tetrahedron Letters.* (2001) 42, 7751-7754.

Mulvihill et al., "Synthesis and Application of Novel Glyoxylate-derived Chloroformates," *Synthesis* (2002) 3, 365-370.

Nahum-Levy et al., "Putative Partial Agonist 1-Aminocyclopropanecarboxylic Acid Acts Concurrently as a Glycine-Site Agonist and a Glutamate-Site Antagonist at N-methyl-D-aspartate Receptors," *Molecular Pharmacology* (1999) 56, 1207-1218.

Ogawa et al., "D-Cycloserine for the treatment of ataxia in spinocerebellar degeneration," *J Neur Sci* (2003) 210, 53-56.

Ogawa, "Pharmacological treatments of cerebellar ataxia," *Cerebellum* (2004) 3(2), 107-111.

Rabe, C. S., & Tabakoff, B. "Glycine Site-Directed Agonists Reverse the Actions of Ethanol at the N-Methyl-D-aspartate Receptor," *Mol Pharmacol*, (1990) 38(6), 753-757.

Richardson et al., "Facilitation of Fear Extinction by D-Cycloserine: Theoretical and Clinical Implications," *Learn. Mem.* (2004) 11, 510-516.

Sun et al., "N-Acyloxymethyl Carbamate Linked Prodrugs of Pseudomycins Are Novel Antifungal Agents," *Bioorg. Med. Chem. Lett.* 2001, 11, 1875-1879.

Sun et al., "Synthesis and Evaluation of Novel Pseudomycin Side-Chain Analogues. Part 3," *Bioorg. Med. Chem. Lett.* (2001), 11, 3055-3059.

Supplisson et al., "Why glycine transporters have different stoichiometries," *FEBS Letters Published by Elsevier.*( 2002) 529, 93-101.

Tsai et al., "D-Serine Added to Antipsychotics for the Treatment of Schizophrenia," *Biol. Psychiatry* (1998) 44, 1081-1089.

Tsai et al., "Glycine Transporter I Inhibitor, N-Methylglycine (Sarcosine), Added to Antipsychotics for the Treatment of Schizophrenia," *Biol. Psychiatry* (2004), 55, 452-456.

Tsai et al., D-Alanine Added to Antipsychotics for the Treatment of Schizophrenia, *Biol. Psychiatry* (2006) 59, 230-234.

Tuominen, H. J., Tiihonen, J., & Wahlbeck, K. (2005). "Glutamatergic drugs for schizophrenia: a systematic review and meta-analysis," *Schizophr Res*, 72(2-3), 225-234.

Van Berckel et al., "Efficacy and Tolerance of D-Cycloserine in Drug-Free Schizophrenic Patients," *Biol. Psychiatry* (1996) 40, 1298-1300.

A.R. Hamel et al., "Water-soluable prodrugs of cyclosporine A with tailored conversion rates", Journal of Peptide Research vol. 65, No. 3, 2005, pp. 364-374, GB Blackwell Publishing Ltd., Oxford.

International Search Report and Written Opinion mailed Jan. 2, 2008 from corresponding International Application No. PCT/US2007/016739, international filing date Jul. 26, 2007.

Office Action mailed Jul. 3, 2008 for U.S. Appl. No. 11/878,661, filed Jul. 26, 2007.

Notice of Allowance mailed Dec. 31, 2008 for U.S. Appl. No. 11/878,661, filed Jul. 26, 2007.

* cited by examiner

ACYLOXYALKYL CARBAMATE PRODRUGS OF α-AMINO ACIDS, METHODS OF SYNTHESIS AND USE

This application is a continuation application of U.S. patent application Ser. No. 11/878,661 filed on Jul. 26, 2007, now allowed issued as U.S. Pat. No. 7,531,572, which claims the benefit under 35 U.S.C. §119(e) of U.S. Provisional Application No. 60/833,774 filed Jul. 28, 2006, each of which is incorporated by reference herein in its entirety.

FIELD

The disclosure relates to acyloxyalkyl carbamate prodrugs of α-amino acids, methods of making acyloxyalkyl carbamate prodrugs of α-amino acids, methods of using acyloxyalkyl carbamate prodrugs of α-amino acids, and pharmaceutical compositions comprising acyloxyalkyl carbamate prodrugs of α-amino acids to treat disease. The disclosure also relates to acyloxyalkyl carbamate prodrugs of α-amino acids suitable for oral administration using sustained release dosage forms.

BACKGROUND

Schizophrenia is a psychotic disorder associated with positive, negative, and cognitive symptoms, neuropsychological deficits, and poor social functioning. Classical theories of schizophrenia have focused on abnormal dopaminergic neurotransmission, and clinical treatments for schizophrenia include use of the typical ("first generation") and atypical ("second generation") antipsychotics, which function in part as dopamine antagonists. Examples of typical antipsychotics (or neuroleptics) include chlorpromazine, haloperidol, fluphenazine, and thioridazine. Examples of atypical antipsychotic include clozapine, risperidone, olanzapine, quetiapine, ziprasidone, aripiprazole, and sertindole.

Recent theories have postulated that schizophrenia is associated with dysfunction or dysregulation of neurotransmission mediated at brain N-methyl-D-aspartate (NMDA)-type glutamate receptors (Javitt, D. C. and Zukin, S. R., *Am. J. Psychiatry* 1991, 148, 1301-1308; Javitt, U.S. Pat. No. 5,837,730; Javitt et al., U.S. Pat. No. 5,854,286; Javitt, U.S. Pat. No. 6,162,827; Javitt, U.S. Pat. No. 6,355,681; Javitt, U.S. Pat. No. 6,361,957; Tsai and Coyel, U.S. Pat. No. 6,667,297; Tsai and Coyel, U.S. Pat. No. 6,974,821; Javitt, U.S. Application Publication No. 2002/0010212; Javitt, U.S. Application Publication No. 2002/0013364; Tsai and Coyel, U.S. Application Publication No. 2002/0035145; U.S. Application Publication No. 2002/0161048; Javitt, U.S. Application Publication No. 2002/0183390; Tsai and Coyel, U.S. Application Publication No. 2002/0193429; Tsai and Coyel, U.S. Application Publication No. 2004/0092530; Javitt, U.S. Application Publication No. 2005/0159488; and Tsai and Coyet, U.S. Application Publication No. 2005/0250851). NMDA glycine-site agonists (including glycine, D-serine, and D-alanine) and partial agonists (e.g., D-cycloserine) induce significant improvement in negative and cognitive symptoms in schizophrenics (Javitt et al., *Am. J. Psychiatry* 1994, 151, 1234-1236; Heresco-Levy et al., *Br. J. Psychiatry* 1996, 169, 610-617; Heresco-Levy et al., *Arch. Gen. Psychiatry* 1999, 56, 29-36; Heresco-Levy et al., *Am. J. Psychiatry* 2002, 159, 480-482; Goff, et al., *Am. J. Psychiatry* 1995, 152, 1213-1215; Goff et al., *Arch. Gen. Psychiatry* 1999, 56, 21-27; van Berckel et al., *Biol. Psychiatry* 1996, 40, 1298-1300; Tsai et al., *Biol. Psychiatry* 1998, 44, 1081-1089; and Tsai et al., *Biol. Psychiatry* 2006, 59, 230-234, each of which is incorporated by reference herein in its entirety), supporting the role of glutamatergic hypofunctioning in this psychotic disorder. While clinical studies of schizophrenia using NMDA agonists as single agents have been undertaken (e.g., van Berckel et al., *Biol. Psychiatry* 1996, 40, 1298-1300), in the majority of the published studies these compounds were administered adjunctively with either conventional neuroleptics or atypical antipsychotic drugs to augment the activity of standard therapies.

Synaptic levels of the endogenous agonists for the NMDA receptor glycine site, for example, glycine and D-serine, are regulated in the mammalian brain by the activity of reuptake transporters. Inhibition of such transporters can potentiate signaling by the endogenous agonist and can provide an alternative to direct administration of the agonist itself. High affinity glycine transporters are encoded by two separate genes: GLYT1 and GLYT2 (Supplisson et al., *FEBS Lett.* 2002, 529, 93-101). GLYT1 is expressed abundantly in glial cells and is believed to be a primary regulator of glycine concentrations at the NMDA receptor. Sarcosine (N-methylglycine) is a transported, competitive inhibitor of GLYT1 that has been dosed adjunctively with typical and atypical antipsychotic agents and is shown to improve positive, negative, and cognitive symptom domains in schizophrenic patients (Tsai et al., *Biol. Psychiatry* 2004, 55, 452-456; and Lane et al., *Arch. Gen. Psychiatry* 2005, 62, 1196-1204).

1-Aminocyclopropanecarboxylic acid is frequently characterized in the literature as an NMDA partial agonist acting at the glycine site, although a recent detailed mechanistic analysis supports concurrent high affinity, fully efficacious agonist activity at the glycine site and lower affinity antagonist activity at the glutamate binding site of the NMDA heterodimer (Nahum-Levy et al., *Mol. Pharmacol.* 1999, 56, 1207-1218). The utility of 1-aminocyclopropanecarboxylic acid as therapy for a variety of neurodegenerative and neuropsychiatric disorders is predicated on its functional antagonism of NMDA neurotransmission at relatively high doses (Trullas and Skolnick., U.S. Pat. No. 5,086,072; Skolnick et al., U.S. Pat. No. 5,428,069; Maccecchini, U.S. Pat. No. 5,523,323; Skolnick et al., U.S. Pat. No. 6,017,957; Schneider, U.S. Application Publication No. 2004/0087596; Davis and Ressler, U.S. Application Publication No. 2004/0208923; and Davis and Ressler, U.S. Application Publication No. 2005/0096396).

The sub-optimal biopharmaceutical properties of α-amino acid NMDA glycine-site agonists such as glycine, D-serine, D-alanine, and 1-aminocyclopropanecarboxylic acid, and GLYT1 inhibitors such as sarcosine can significantly limit the clinical utility of these agents in the treatment of schizophrenia and other CNS disorders. Glycine has limited blood-brain-barrier permeability and enormous doses (about 30-60 g/day) must be administered to produce a beneficial effect in schizophrenics. While oral therapy with D-serine and sarcosine has allowed for more pharmaceutically practical doses (about 2 g/day), the intrinsically rapid clearance of these amino acids has necessitated frequent daily administration (t.i.d), providing a therapeutic regimen that discourages compliance and is inconvenient for patients. Moreover, the short half-lives of these amino acids ensure that plasma levels fluctuate widely, potentially limiting exposure to optimum therapeutic levels throughout the day.

This disclosure satisfies an unmet need for new medicinal agents that can provide for stimulation of NMDA receptor signaling pathways and are suitable for administration to patients in need of such therapy once daily or multiple times daily. Such compounds, and pharmaceutical compositions comprising the compounds, can be useful for the treatment of, for example, positive, negative, and/or cognitive symptom domains in schizophrenics, and may be administered alone or adjunctive to other antipsychotic medicaments. These compounds, and pharmaceutical compositions comprising the compounds, can also be useful for treatment of other neuropsychiatric and neurodegenerative diseases such as dementia, depression, attention-deficit disorders, learning and memory disorders, and other diseases where NMDA-mediated neurotransmission is implicated.

SUMMARY

In a first aspect, compounds of Formula (I):

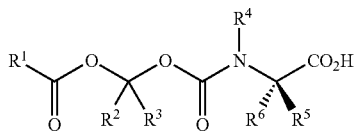

pharmaceutically acceptable salts thereof, and pharmaceutically acceptable solvates of any of the foregoing, are provided, wherein:

$R^1$ is chosen from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^2$ and $R^3$ are independently chosen from hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl, and substituted heteroarylalkyl, or $R^2$ and $R^3$, together with the carbon atom to which they are bonded, form a ring chosen from a cycloalkyl, substituted cycloalkyl, cycloheteroalkyl, and substituted cycloheteroalkyl ring;

$R^4$ is chosen from hydrogen and methyl;

$R^5$ is chosen from hydrogen, methyl, and hydroxymethyl; and $R^6$ is hydrogen, or $R^5$ and $R^6$ together with the carbon atom to which they are bonded form a ring chosen from a 1,1-cyclopropane ring and substituted 1,1-cyclopropane ring.

In a second aspect, pharmaceutical compositions comprising at least one pharmaceutically acceptable vehicle and a therapeutically effective amount of at least one compound of Formula (I) are provided.

In a third aspect, sustained release oral dosage forms comprising at least one compound of Formula (I) are provided.

In a fourth aspect, methods of synthesizing compounds of Formula (I), pharmaceutically acceptable salts thereof, and pharmaceutically acceptable solvates of any of the foregoing are provided, comprising contacting a compound of Formula (II) with a compound of Formula (III) to provide the compounds of Formula (I):

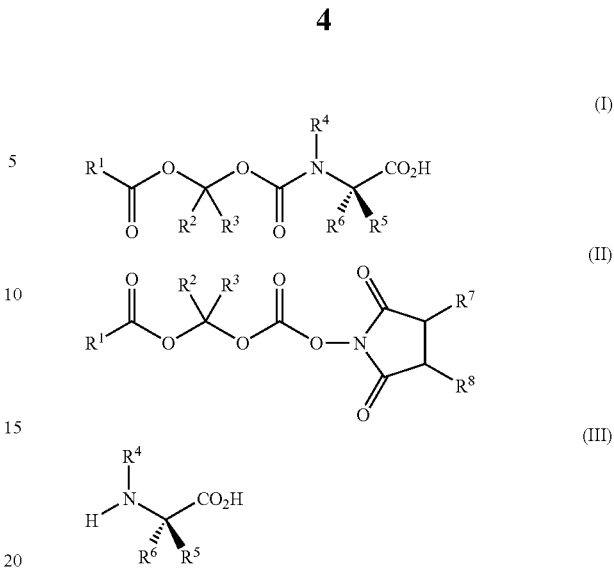

wherein:

$R^1$, $R^2$, $R^3$, $R^4$, $R^5$ and $R^6$ are as defined above; and $R^7$ and $R^8$ are independently chosen from hydrogen, acylamino, acyloxy, alkoxycarbonylamino, alkoxycarbonyloxy, alkyl, substituted alkyl, alkoxy, substituted alkoxy, aryl, substituted aryl, arylalkyl, substituted arylalkyl, carbamoyloxy, dialkylamino, heteroaryl, substituted heteroaryl, hydroxy, and sulfonamido, or $R^7$ and $R^8$ together with the atoms to which they are bonded form a ring chosen from a substituted cycloalkyl, substituted cycloheteroalkyl, and substituted aryl ring.

In a fifth aspect, methods of treating a disease in a patient are provided, the methods comprising administering to a patient in need of such treatment a therapeutically effective amount of a colonically absorbable form of at least one α-amino acid.

In a sixth aspect, methods of treating a disease in a patient are provided, the methods comprising administering to a patient in need of such treatment a therapeutically effective amount of at least one compound of Formula (I).

These and other aspects are provided by the disclosure herein of acyloxyalkyl carbamate prodrugs of α-amino acids, pharmaceutical compositions of acyloxyalkyl carbamate prodrugs of α-amino acids, methods of making acyloxyalkyl carbamate prodrugs of α-amino acids, and methods of using acyloxyalkyl carbamate prodrugs of α-amino acids and/or pharmaceutical compositions thereof to treat various diseases such as cognitive disorders, anxiety disorders, schizophrenia, psychosis, substance-related or addictive disorders, pain, obesity, eating disorders, dyskinesias, neuropsychiatric disorders, neurodegenerative disorders, urinary incontinence, neuronal damage, emesis, and sleep disorders. In certain embodiments, an acyloxyalkyl carbamate prodrug of an α-amino acid is an acyloxylalkyl carbamate prodrug of an α-amino acid chosen from D-serine, D-alanine, 1-aminocyclopropanecarboxylic acid, and sarcosine.

DETAILED DESCRIPTION

Definitions

A dash ("-") that is not between two letters or symbols is used to indicate a point of attachment for a moiety or substituent. For example, —$CONH_2$ is a moiety bonded through the carbon atom.

"Acyl," by itself or as part of another substituent, refers to the radical —C(O)R$^{30}$, where R$^{30}$ is chosen from hydrogen, alkyl, cycloalkyl, cycloheteroalkyl, aryl, arylalkyl, heteroalkyl, heteroaryl, and heteroarylalkyl as defined herein. Examples of acyl groups include, but are not limited to, formyl, acetyl, cyclohexylcarbonyl, cyclohexylmethylcarbonyl, benzoyl, benzylcarbonyl, and the like.

"Acylamino," by itself or as part of another substituent, refers to the radical —NR$^{31}$C(O)R$^{32}$, where R$^{31}$ and R$^{32}$ are independently chosen from hydrogen, alkyl, cycloalkyl, cycloheteroalkyl, aryl, arylalkyl, heteroalkyl, heteroaryl, and heteroarylalkyl as defined herein. Examples of acylamino groups include, but are not limited to formamido, acetamido, and benzamido.

"1-Acyloxy-alkyl carbamate" refers to an N—1-acyloxy-alkoxycarbonyl derivative of an α-amino acid as encompassed by compounds of Formula (I) disclosed herein.

"Alkyl," by itself or as part of another substituent, refers to a saturated or unsaturated, branched or straight-chain monovalent hydrocarbon radical derived by the removal of one hydrogen atom from a single carbon atom of a parent alkane, alkene or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double, and triple carbon-carbon bonds. Where a specific level of saturation is intended, the terms "alkanyl," "alkenyl," and "alkynyl" are used. In certain embodiments, alkyl groups comprise from 1 to 20 carbon atoms, in certain embodiments, from 1 to 6 carbon atoms, and in certain embodiments, from 1 to 3 carbon atoms.

"Alkanyl," by itself or as part of another substituent, refers to a saturated, branched or straight-chain alkyl radical derived by the removal of one hydrogen atom from a single carbon atom of a parent alkane. Examples of alkanyl groups include, but are not limited to, methanyl; ethanyl; propanyls such as propan-1-yl, propan-2-yl (isopropyl), etc.; butanyls such as butan-1-yl, butan-2-yl (sec-butyl), 2-methyl-propan-1-yl (isobutyl), 2-methyl-propan-2-yl (t-butyl), etc.; and the like.

"Alkenyl," by itself or as part of another substituent, refers to an unsaturated, branched or straight-chain alkyl radical having at least one carbon-carbon double bond derived by the removal of one hydrogen atom from a single carbon atom of a parent alkene. The group may be in either the cis or trans conformation about each double bond. Examples of alkenyl groups include, but are not limited to, ethenyl; propenyls such as prop-1-en-1-yl, prop-1-en-2-yl, prop-2-en-1-yl (allyl), prop-2-en-2-yl, butenyls such as but-1-en-1-yl, but-1-en-2-yl, 2-methyl-prop-1-en-1-yl, but-2-en-1-yl, but-2-en-2-yl, but-2-en-2-yl, buta-1,3-dien-1-yl, buta-1,3-dien-2-yl, etc.; and the like.

"Alkynyl," by itself or as part of another substituent, refers to an unsaturated, branched or straight-chain alkyl radical having at least one carbon-carbon triple bond derived by the removal of one hydrogen atom from a single carbon atom of a parent alkyne. Examples of alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyloxy," by itself or as part of another substituent, refers to the radical —OC(O)R$^{33}$, where R$^{33}$ is chosen from alkyl, cycloalkyl, cycloheteroalkyl, aryl, arylalkyl, heteroalkyl, heteroaryl, and heteroarylalkyl, as defined herein. Examples of acyloxy groups include, but are not limited to acetoxy, isobutyroyloxy, benzoyloxy, phenylacetoxy, and the like.

"Alkoxy," by itself or as part of another substituent, refers to the radical —OR$^{50}$ where R$^{50}$ represents an alkyl or cycloalkyl group, as defined herein. Examples of alkoxy groups include, but are not limited to, methoxy, ethoxy, propoxy, butoxy, cyclohexyloxy, and the like.

"Alkoxycarbonyl," by itself or as part of another substituent refers to the radical —C(O)OR$^{51}$ where R$^{51}$ represents an alkyl group, as defined herein. Examples of alkoxycarbonyl groups include, but are not limited to, methoxycarbonyl, ethoxycarbonyl, propoxycarbonyl, butoxycarbonyl, and the like.

"Alkoxycarbonylamino," by itself or as part of another substituent, refers to the radical —NR$^{36}$C(O)—OR$^{37}$ where R$^{36}$ is chosen from alkyl and cycloalkyl; and R$^{37}$ is chosen from alkyl, cycloalkyl, cycloheteroalkyl, aryl, arylalkyl, heteroalkyl, heteroaryl, and heteroarylalkyl, as defined herein. Examples of alkoxycarbonylamino groups include, but are not limited to, methoxycarbonylamino, tert-butoxycarbonylamino, and benzyloxycarbonylamino.

"Alkoxycarbonyloxy," by itself or as part of another substituent, refers to the radical —OC(O)—OR$^{38}$ where R$^{38}$ is chosen from alkyl and cycloalkyl, as defined herein. Examples of alkoxycarbonyloxy include, but are not limited to, methoxycarbonyloxy, ethoxycarbonyloxy, and cyclohexyloxycarbonyloxy.

"Alkylamino," by itself or as part of another substituent, refers to the radical —NHR$^{53}$ where R$^{53}$ is chosen from alkyl and cycloalkyl, as defined herein.

"α-Amino acid" refers to a compound of Formula (III):

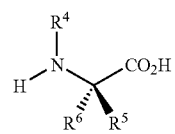

(III)

wherein R$^4$ is chosen from hydrogen and methyl, R$^5$ is chosen from hydrogen, methyl, and hydroxymethyl; and R$^6$ is hydrogen; or R$^5$ and R$^6$ together with the carbon atom to which they are bonded form a ring chosen from a 1,1-cyclopropane ring and a substituted 1,1-cyclopropane ring. In certain embodiments, an α-amino acid is chosen from D-serine, D-alanine, 1-aminocyclopropanecarboxylic acid, and sarcosine "Aryl," by itself or as part of another substituent, refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, aryl groups have from 5 to 20 carbon atoms, and in certain embodiments, from 5 to 12 carbon atoms. In certain embodiments, aryl has from 6 to 10 carbon atoms.

"Arylalkyl," by itself or as part of another substituent, refers to an acyclic alkyl radical in which one of the hydrogen atoms bonded to a carbon atom, typically a terminal or $sp^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the nomenclature "arylalkanyl," "arylalkenyl," or "arylalkynyl" is used. In certain embodiments, an arylalkyl group is $C_{7-30}$ arylalkyl, e.g., the alkanyl, alkenyl or alkynyl moiety of the arylalkyl group is $C_{1-10}$ and the aryl moiety is $C_{6-20}$ and in certain embodiments, an arylalkyl group is $C_{7-20}$ arylalkyl, e.g., the alkanyl, alkenyl or alkynyl moiety of the arylalkyl group is $C_{1-8}$ and the aryl moiety is $C_{6-12}$. In certain embodiments, arylalkyl is $C_{6-10}$ arylalkyl.

"AUC" is the area under a curve representing the concentration of a compound or metabolite thereof in a biological fluid in a patient as a function of time following administration of the compound to the patient. In certain embodiments, the compound is a prodrug and the metabolite is a drug. Examples of biological fluids include plasma, blood, and cerebrospinal fluid. The AUC may be determined by measuring the concentration of a compound or metabolite thereof in a biological fluid such as the plasma or blood using methods such as liquid chromatography-tandem mass spectrometry (LC/MS/MS), at various time intervals, and calculating the area under the plasma concentration-versus-time curve. Suitable methods for calculating the AUC from a drug concentration-versus-time curve are well known in the art. For example, an AUC for an α-amino acid may be determined by measuring the concentration of the α-amino acid in the plasma or blood of a patient following administration of a compound of Formula (I) to the patient.

"$C_{max}$" is the maximum concentration of a drug in the plasma or blood of a patient following administration of a dose of the drug or prodrug to the patient.

"$T_{max}$" is the time to the maximum concentration ($C_{max}$) of a drug in the plasma or blood of a patient following administration of a dose of the drug or prodrug to the patient "Carbamoyl," by itself or as part of another substituent, refers to the radical —C(O)NR$^{39}$R$^{40}$ where R$^{39}$ and R$^{40}$ are independently chosen from hydrogen, alkyl, cycloalkyl, and aryl, as defined herein.

"Carbamoyloxy," by itself or as part of another substituent refers to the radical —OC(O)$_2$NR$^{41}$R$^{42}$ where R$^{41}$ and R$^{42}$ are independently chosen from hydrogen, alkyl, cycloalkyl, cycloheteroalkyl, aryl, arylalkyl, heteroalkyl, heteroaryl, and heteroarylalkyl, as defined herein, or R$^{41}$ and R$^{42}$ together with the nitrogen atom to which they are bonded form a ring chosen from a cycloheteroalkyl and a heteroaryl ring.

"Cleave" refers to breakage of chemical bonds and is not limited to chemical or enzymatic reactions or mechanisms unless clearly intended by the context.

"Compounds" of Formula (I) disclosed herein include any specific compounds within the formula having a structure is disclosed herein. Compounds may be identified by their chemical structure and/or chemical name. If the chemical structure and chemical name conflict, the chemical structure is determinative of the identity of the compound.

The compounds described herein may comprise one or more chiral centers and/or double bonds and therefore may exist as stereoisomers such as double-bond isomers (i.e., geometric isomers), enantiomers, and diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques and stereoisomerically pure forms may be synthesized using chiral synthesis techniques well known to the skilled artisan.

Compounds of Formula (I) include, but are not limited to, optical isomers of compounds of Formula (I), racemates thereof, and other mixtures thereof. In such embodiments, the single enantiomers or diastereomers, i.e., optically active forms, may be obtained by asymmetric synthesis or by resolution of the racemates. Resolution of the racemates may be accomplished, for example, by conventional methods such as crystallization in the presence of a resolving agent, or chromatography, using, for example, a chiral high-pressure liquid chromatography (HPLC) column. In addition, compounds of Formula (I) include Z- and E-forms (or cis- and trans-forms) of compounds with double bonds. In embodiments in which compounds of Formula (I) exist in various tautomeric forms, compounds of Formula (I) include any and all tautomeric forms of the compound.

The compounds of Formula (I) may also exist in several tautomeric forms including the enol form, the keto form, and mixtures thereof. Accordingly, the chemical structures depicted herein encompass any and all possible tautomeric forms of the illustrated compounds. The compounds of Formula (I) also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds may exist in unsolvated forms as well as solvated forms, including hydrated forms and as N-oxides. In general, compounds may be hydrates, solvates, or N-oxides. Certain compounds may exist in multiple crystalline, co-crystalline, or amorphous forms. Compounds of Formula (I) include pharmaceutically acceptable salts thereof, pharmaceutically acceptable solvates of the free acid form of any of the foregoing, as well as crystalline or co-crystalline forms of any of the foregoing.

In general, all physical forms are equivalent for the uses contemplated herein and are intended to be within the scope of the present disclosure. Further, it should be understood, when partial structures of the compounds are illustrated, that an asterisk indicates the point of attachment of the partial structure to the rest of the molecule.

"Corresponding α-amino acid" refers to an α-amino acid of Formula (III) having the same $R^4$, $R^5$, and $R^6$ groups as the α-amino acid prodrug of Formula (I).

"Cycloalkoxycarbonyl," by itself or as part of another substituent, refers to the radical —C(O)O$R^{52}$ where $R^{52}$ represents an cycloalkyl group as defined herein. Examples of cycloalkoxycarbonyl groups include, but are not limited to, cyclobutyloxycarbonyl, cyclohexyloxycarbonyl, and the like.

"Cycloalkyl," by itself or as part of another substituent, refers to a saturated or partially unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-10}$ cycloalkyl, and in certain embodiments, $C_{3-7}$ cycloalkyl.

"Cycloheteroalkyl," by itself or as part of another substituent, refers to a saturated or partially unsaturated cyclic alkyl radical in which one or more carbon atoms (and any associated hydrogen atoms) are independently replaced with the same or different heteroatom. Examples of heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Examples of cycloheteroalkyl groups include, but are not limited to, groups derived from epoxides, azirines, thiiranes, imidazolidine, morpholine, piperazine, piperidine, pyrazolidine, pyrrolidine, quinuclidine, and the like.

"Dialkylamino," by itself or as part of another substituent refers to the radical —N$R^{43}R^{44}$ where $R^{43}$ and $R^{44}$ are independently chosen from alkyl, cycloalkyl, cycloheteroalkyl, arylalkyl, heteroalkyl, and heteroarylalkyl, or $R^{43}$ and $R^{44}$ together with the nitrogen to which they are bonded form a cycloheteroalkyl ring.

"1,1-Cyclopropane ring" refers to a moiety having the structural formula:

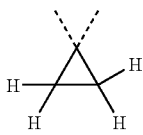

wherein the dashed bonds indicate the positions to which the 1,1-cyclopropane ring is bonded. In certain embodiments, one or more of the hydrogen atoms bonded to the 1,1-cyclopropane ring is independently substituted with a substituent group chosen from halogen, $C_{1-3}$ alkyl, —OH, —$NH_2$, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino.

"Disease" refers to a disease, disorder, condition, symptom, or indication.

"Heteroalkyl," by itself or as part of another substituent, refers to an alkyl group in which one or more of the carbon atoms (and any associated hydrogen atoms) are independently replaced with the same or different heteroatomic groups. Examples of heteroatomic groups include, but are not limited to, —O—, —S—, —O—O—, —S—S—, —O—S—, —N$R^{70}R^{71}$—, =N—N=, —N=N—, —N=N—N$R^{72}R^{73}$, —P$R^{74}$—, =P(O)$_2$—PO$R^{75}$—, —O—P(O)$_2$—SO—, —SO$_2$—, —Sn$R^{76}R^{77}$—, and the like, where $R^{70}$, $R^{71}$, $R^{72}$, $R^{73}$, $R^{74}$, $R^{75}$, $R^{76}$, and $R^{77}$ are independently chosen from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl. Where a specific level of saturation is intended, the nomenclature "heteroalkanyl," "heteroalkenyl," or "heteroalkynyl" is used.

"Heteroaryl," by itself or as part of another substituent, refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which may be aromatic or non-aromatic. Heteroaryl encompasses 5- to 7-membered aromatic, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heteroaromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is a 5- to 20-membered heteroaryl, and in certain embodiments a 5- to 10-membered heteroaryl. In certain embodiments, heteroaryl groups are those derived from thiophene, pyrrole, benzothiophene, benzofuran, indole, pyridine, quinoline, imidazole, oxazole, and pyrazine.

"Heteroarylalkyl," by itself or as part of another substituent, refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature "heteroarylalkanyl," "heteroarylalkenyl," and "heteroarylalkynyl" is used. In certain embodiments, a heteroarylalkyl group is a 6- to 30-membered heteroarylalkyl, e.g., the alkanyl, alkenyl, or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl.

"Neuropsychiatric" and/or "neurodegenerative disorders" include psychotic disorders such as schizophrenia, schizophreniform disorder, schizoaffective disorder, delusional disorder, drug-induced psychotic disorder, and illness associated with psychosis (e.g., major depression, bipolar disorder, and post-traumatic stress syndrome); cognitive disorders including dementia (e.g., associated with Alzheimer's disease, Parkinson's disease, Huntington's disease, HIV, Pick's Disease, and Creutzfeldt-Jakob disease), amnestic disorders, and age-related cognitive decline; anxiety disorders including generalized anxiety disorder, obsessive-compulsive disorder, social phobia, and panic attack; mood disorders (e.g., depression, seasonal depression, postpartum depression, premenstrual syndrome, and premenstrual dysphoric disorder); attention disorders including attention-deficit hyperactivity disorder; autism; and movement disorders (e.g., Parkinsonism, akinesias, akathisias, and dyskinesias including tardive dyskinesia, dystonia, spasticity, epilepsy, and Tourette's syndrome), the diagnosis of which can be made with reference to the fourth edition of the Diagnostic and Statistical Manual of Mental Disorders (DSM-IV-TR, Fourth Edition, Text Revision, American Psychiatric Association, Washington D.C., 2000).

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated, partially saturated, or unsaturated, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated, partially saturated, or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Patient" includes mammals, such as for example, humans.

"Pharmaceutical composition" refers to at least one compound of Formula (I) and a pharmaceutically acceptable vehicle, with which the compound is to be administered to a patient.

"Pharmaceutically acceptable" refers to approved or approvable by a regulatory agency of a federal or a state government, listed in the U.S. Pharmacopoeia or listed other generally recognized pharmacopoeia for use in mammals, including humans.

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and (2) salts formed when an acidic proton present in the parent compound is replaced by a metal ion, e.g., an alkali metal ion, an alkaline earth metal ion, or an aluminum ion; or coordinates with an organic base such as ethanolamine, diethanolamine, triethanolamine, N-methylglucamine and the like. In certain embodiments, the salt is the hydrochloride salt, and in certain embodiments the salt is the sodium salt.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound of Formula (I) may be administered to a patient and which does not destroy the pharmacological activity thereof, and which is nontoxic when administered in doses sufficient to provide a therapeutically effective amount of the compound.

Prodrug" refers to a derivative of a drug molecule that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach, or the agent may be supplied exogenously. In certain embodiments, the drug is an α-amino acid of Formula (III) and the promoiety is an acyloxyalkyloxycarbonyl group having the structure:

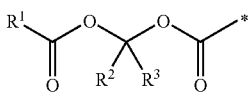

where $R^1$, $R^2$, and $R^3$ are defined herein.

"Protecting group" refers to a group of atoms, that when bonded to a reactive-functional group in a molecule, masks, reduces or prevents reactivity of the functional group. Examples of protecting groups can be found in Wuts and Greene et al., "Protective Groups in Organic Synthesis," John Wiley and Sons, 4th ed, 2006, and Harrison et al., "Compendium of Synthetic Organic Methods," Vols. 1-11, John Wiley and Sons, 1971-2003. Representative amino protecting groups include, but are not limited to, formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers, and allyl ethers.

"Solvate" refers to a molecular complex of a compound with one or more solvent molecules in a stoichiometric or non-stoichiometric amount. Such solvent molecules are those commonly used in the pharmaceutical arts, e.g., water, ethanol, and the like. A molecular complex of a compound or moiety of a compound and a solvent can be stabilized by non-covalent intra-molecular forces such as, electrostatic forces, van der Waals forces, and/or hydrogen bonds. The term "hydrate" refers to a complex in which the one or more solvent molecules are water including monohydrates and hemi-hydrates.

"Substantially one diastereomer" refers to a compound containing two or more stereogenic centers such that the diastereomeric excess (d.e.) of the compound is greater than or equal to 90%. In certain embodiments, the d.e. is, for example, greater than or equal to 91%, 92%, 93%, 94%, 95%, 96%, 97%, 98%, and 99%.

"Substantially one enantiomer" refers to a compound containing one stereogenic center such that the enantiomeric excess (e.e.) of the compound is at least 90%. In certain embodiments, the e.e. is, for example, greater than or equal to 91%, 92%, 93%, 94%, 95%, 96%, 97%, 98%, and 99%.

"Substituted" refers to a group in which one or more hydrogen atoms are independently replaced with the same or different substituent(s). Examples of substituents include, but are not limited to, —X, —$R^{60}$, —$O^-$, =O, —$OR^{60}$, —$SR^{60}$, —$S^-$, =S, —$NR^{60}R^{61}$, =$NR^{60}$, —$CX_3$, —CN, —$CF_3$, —OCN, —SCN, —NO, —$NO_2$, =$N_2$, —$N_3$, —$S(O)_2O$—, —$S(O)_2OH$, —$S(O)_2R^{61}$, —$OS(O_2)O$—, —$OS(O)_2R^{60}$, —$P(O)(O-)_2$, —$P(O)(OR^{60})(O^-)$, —$OP(O)(OR^{60})(OR^{61})$, —$C(O)R^{60}$, —$C(S)R^{61}$, —$C(O)OR^{60}$, —$C(O)NR^{60}R^{61}$, —C(O)O, (S)$OR^{60}$, —$NR^{62}C(O)NR^6R^6$, —$NR^{62}C(S)NR^{60}R^{61}$, —$NR^{62}C(NR^{63})NR^{60}R^{61}$, —$C(NR^{62})NR^6OR^{61}$, —$S(O)_2$, $NR^6OR^{61}$, —$NR^{63}S(O)_2R^{60}$, —$NR^{63}C(O)R^{60}$, and —$S(O)R^{60}$ where each X is independently a halogen; each $R^{60}$ and $R^{61}$ are independently chosen from hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl, substituted heteroaryl, arylalkyl, substituted arylalkyl, heteroarylalkyl, and substituted heteroarylalkyl, or $R^{60}$ and $R^{61}$, together with the nitrogen atom to which they are bonded, form a ring chosen from a cycloheteroalkyl, substituted cycloheteroalkyl, heteroaryl, and substituted heteroaryl ring; and each $R^{62}$ and $R^{63}$ are independently chosen from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, and substituted heteroarylalkyl, or $R^{62}$ and $R^{63}$, together with the atom to which they are bonded, form one or more rings chosen from a cycloheteroalkyl, substituted cycloheteroalkyl, heteroaryl, and substituted heteroaryl ring. In certain embodiments, a tertiary amine or aromatic nitrogen may be substituted with one or more oxygen atoms to form the corresponding nitrogen oxide.

In certain embodiments of compounds of Formula (I), each substituent group is independently chosen from halogen, $C_{1-3}$ alkyl, —OH, —$NH_2$, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino.

"Sulfonamido," by itself or as part of another substituent refers to a radical —$NR^{53}S(O)_2R^{54}$, where $R^{53}$ is chosen from alkyl, substituted alkyl, cycloalkyl, cycloheteroalkyl, aryl, substituted aryl, arylalkyl, heteroalkyl, heteroaryl, and heteroarylalkyl; and $R^{54}$ is chosen from hydrogen, alkyl, cycloalkyl, cycloheteroalkyl, aryl, arylalkyl, heteroalkyl, heteroaryl, and heteroarylalkyl, as defined herein. Examples of sulfonamido groups include, but are not limited to, methanesulfonamido, benzenesulfonamido, and p-toluenesulfonamido.

"Thioalkyl," by itself or as part of another substituent, refers to a radical —$SR^{41}$ where $R^{41}$ is alkyl, as defined herein.

"Treating" or "treatment" of a disease refers to arresting or ameliorating a disease, disorder, or at least one of the clinical symptoms of a disease or disorder. In certain embodiments, "treating" or "treatment" refers to arresting or ameliorating at least one physical parameter of the disease or disorder, which may or may not be discernible by the patient. In certain embodiments, "treating" or "treatment" refers to inhibiting or controlling the disease or disorder, either physically (e.g., stabilization of a discernible symptom), physiologically (e.g., stabilization of a physical parameter), or both. In certain embodiments, "treating" or "treatment" refers to delaying, in some cases indefinitely, the onset of a disease or disorder. In certain embodiments, "treating" or "treatment" refers to reducing the risk of acquiring a disease, disorder, or a clinical symptom of the disease or disorder.

"Therapeutically effective amount" refers to the amount of a compound that, when administered to a subject for treating a disease, or disorder, or at least one of the clinical symptoms of a disease or disorder, is sufficient to affect such treatment of the disease, disorder, or symptom. The "therapeutically effective amount" may vary depending, for example, on the compound, the disease, disorder, and/or symptoms of the disease, severity of the disease, disorder, and/or symptoms of the disease, the age, weight, and/or health of the patient to be treated, and the judgment of the prescribing physician. An appropriate amount in any given instance may be readily ascertained by those skilled in the art or capable of determination by routine experimentation.

Reference is now be made in detail to particular embodiments of compounds and methods. The disclosed embodiments are not intended to be limiting of the claims. To the contrary, the claims are intended to cover all alternatives, modifications, and equivalents.

Compounds

Certain embodiments of the present disclosure provide compounds of Formula (I):

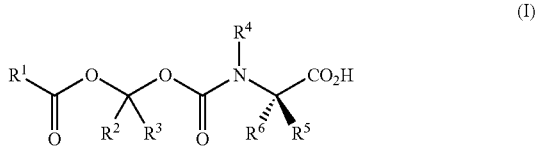

pharmaceutically acceptable salts of any of the foregoing, and a pharmaceutically acceptable solvates of any of the foregoing, wherein:

$R^1$ is chosen from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^2$ and $R^3$ are independently chosen from hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl, and substituted heteroarylalkyl, or $R^2$ and $R^3$ together with the carbon atom to which they are bonded form a ring chosen from a cycloalkyl, substituted cycloalkyl, cycloheteroalkyl, and substituted cycloheteroalkyl ring;

$R^4$ is chosen from hydrogen and methyl;

$R^5$ is chosen from hydrogen, methyl, and hydroxymethyl; and $R^6$ is hydrogen, or $R^5$ and $R^6$ together with the carbon atom to which they are bonded, form a ring chosen from a 1,1-cyclopropane ring and substituted 1,1-cyclopropane ring.

In certain embodiments of the compounds of Formula (I), each substituent group is independently chosen from halogen, $C_{1-3}$ alkyl, —OH, —$NH_2$, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino.

In certain embodiments of the compounds of Formula (I), $R^4$ is hydrogen, $R^5$ is hydroxymethyl, and $R^6$ is hydrogen. In certain embodiments of the compounds of Formula (I), $R^4$ is hydrogen, $R^5$ is methyl, and $R^6$ is hydrogen. In certain embodiments of the compounds of Formula (I), $R^4$ is hydrogen, and $R^5$ and $R^6$ together with the carbon atom to which they are bonded form a 1,1-cyclopropane ring. In certain embodiments of the compounds of Formula (I), $R^4$ is methyl, $R^5$ is hydrogen, and $R^6$ is hydrogen.

In certain embodiments of the compounds of Formula (I), $R^1$ is chosen from $C_{1-6}$ alkyl, substituted $C_{1-6}$ alkyl, $C_{6-10}$ aryl, substituted $C_{6-10}$ aryl, $C_{3-7}$ cycloalkyl, substituted $C_{3-7}$ cycloalkyl, $C_{6-10}$ arylalkyl, and $C_{6-10}$ substituted arylalkyl. In certain embodiments of the compounds of Formula (I) wherein $R^1$ is chosen from $C_{1-6}$ alkyl, substituted $C_{1-6}$ alkyl, $C_{6-10}$ aryl, substituted $C_{6-10}$ aryl, $C_{3-7}$ cycloalkyl, substituted $C_{3-7}$ cycloalkyl, $C_{6-10}$ arylalkyl, and $C_{6-10}$ substituted arylalkyl, each substituent group is independently chosen from halogen, $C_{1-3}$ alkyl, —OH, —$NH_2$, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino.

In certain embodiments of the compounds of Formula (I), $R^1$ is chosen from $C_{1-4}$ alkyl, phenyl, substituted phenyl, cyclohexyl, substituted cyclohexyl, styryl, and substituted styryl. In certain embodiments of the compounds of Formula (I) wherein $R^1$ is chosen from $C_{1-4}$ alkyl, phenyl, substituted phenyl, cyclohexyl, substituted cyclohexyl, styryl, and substituted styryl, each substituent group is independently chosen from halogen, $C_{1-3}$ alkyl, —OH, —$NH_2$, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl.

In certain embodiments of the compounds of Formula (I), $R^2$ and $R^3$ are independently chosen from hydrogen, $C_{1-6}$ alkyl, substituted $C_{1-6}$ alkyl, $C_{6-10}$ aryl, substituted $C_{6-10}$ aryl, $C_{3-7}$ cycloalkyl, and substituted $C_{3-7}$ cycloalkyl. In certain embodiments of the compounds of Formula (I) wherein $R^2$ and $R^3$ are independently chosen from hydrogen, $C_{1-6}$ alkyl, substituted $C_{1-6}$ alkyl, $C_{6-10}$ aryl, substituted $C_{6-10}$ aryl, $C_{3-7}$ cycloalkyl, and substituted $C_{3-7}$ cycloalkyl, each substituent group is independently chosen from halogen, $C_{1-3}$ alkyl, —OH, —$NH_2$, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino.

In certain embodiments of the compounds of Formula (I), $R^2$ and $R^3$ are independently chosen from hydrogen, methyl, ethyl, n-propyl, isopropyl, phenyl, and cyclohexyl.

In certain embodiments of the compounds of Formula (I), $R^2$ is hydrogen, and $R^3$ is chosen from hydrogen, methyl, ethyl, n-propyl, isopropyl, phenyl, and cyclohexyl.

In certain embodiments of the compounds of Formula (I), $R^1$ is chosen from $C_{1-6}$ alkyl, substituted $C_{1-6}$ alkyl, $C_{6-10}$ aryl, substituted $C_{6-10}$ aryl, $C_{3-7}$ cycloalkyl, substituted $C_{3-7}$ cycloalkyl, $C_{6-10}$ arylalkyl, and $C_{6-10}$ substituted arylalkyl, and $R^2$ and $R^3$ are independently chosen from hydrogen, $C_{1-6}$ alkyl, substituted $C_{1-6}$ alkyl, $C_{6-10}$ aryl, substituted $C_{6-10}$ aryl, $C_{3-7}$ cycloalkyl, and substituted $C_{3-7}$ cycloalkyl. In certain embodiments of a compound of Formula (I) wherein $R^1$ is chosen from $C_{1-6}$ alkyl, substituted $C_{1-6}$ alkyl, $C_{6-10}$ aryl, substituted $C_{6-10}$ aryl, $C_{3-7}$ cycloalkyl, substituted $C_{3-7}$ cycloalkyl, $C_{6-10}$ arylalkyl, and $C_{6-10}$ substituted arylalkyl, and $R^2$ and $R^3$ are independently chosen from hydrogen, $C_{1-6}$ alkyl, substituted $C_{1-6}$ alkyl, $C_{6-10}$ aryl, substituted $C_{6-10}$ aryl, $C_{3-7}$ cycloalkyl, and substituted $C_{3-7}$ cycloalkyl, each substituent group is independently chosen from halogen, $C_{1-3}$ alkyl, —OH, —$NH_2$, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, and $R^3$ is chosen from hydrogen, methyl, ethyl, n-propyl, isopropyl, phenyl, and cyclohexyl.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is hydrogen, $R^4$ is hydrogen, $R^5$ is hydroxymethyl, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is methyl, $R^4$ is hydrogen, $R^5$ is hydroxymethyl, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is ethyl, $R^4$ is hydrogen, $R^5$ is hydroxymethyl, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is n-propyl, $R^4$ is hydrogen, $R^5$ is hydroxymethyl, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is isopropyl, $R^4$ is hydrogen, $R^5$ is hydroxymethyl, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is phenyl, $R^4$ is hydrogen, $R^5$ is hydroxymethyl, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is cyclohexyl, $R^4$ is hydrogen, $R^5$ is hydroxymethyl, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is hydrogen, $R^4$ is hydrogen, $R^5$ is methyl, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is methyl, $R^4$ is hydrogen, $R^5$ is methyl, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is ethyl, $R^4$ is hydrogen, $R^5$ is methyl, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is n-propyl, $R^4$ is hydrogen, $R^5$ is methyl, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is isopropyl, $R^4$ is hydrogen, $R^5$ is methyl, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is phenyl, $R^4$ is hydrogen, $R^5$ is methyl, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is cyclohexyl, $R^4$ is hydrogen, $R^5$ is methyl, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is hydrogen, $R^4$ is hydrogen, and $R^5$ and $R^6$ together with the carbon atom to which they are bonded form a 1,1-cyclopropane ring.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is methyl, $R^4$ is hydrogen, and $R^5$ and $R^6$ together with the carbon atom to which they are bonded form a 1,1-cyclopropane ring.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is ethyl, $R^4$ is hydrogen, and $R^5$ and $R^6$ together with the carbon atom to which they are bonded form a 1,1-cyclopropane ring.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is n-propyl, $R^4$ is hydrogen, and $R^5$ and $R^6$ together with the carbon atom to which they are bonded form a 1,1-cyclopropane ring.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is isopropyl, $R^4$ is hydrogen, and $R^5$ and $R^6$ together with the carbon atom to which they are bonded form a 1,1-cyclopropane ring.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is phenyl, $R^4$ is hydrogen, and $R^5$ and $R^6$ together with the carbon atom to which they are bonded form a 1,1-cyclopropane ring.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, and cyclohexyl, and styryl, $R^2$ is hydrogen, $R^3$ is cyclohexyl, $R^4$ is hydrogen, and $R^5$ and $R^6$ together with the carbon atom to which they are bonded form a 1,1-cyclopropane ring.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is hydrogen, $R^4$ is methyl, $R^5$ is hydrogen, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is methyl, $R^4$ is methyl, $R^5$ is hydrogen, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is ethyl, $R^4$ is methyl, $R^5$ is hydrogen, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is n-propyl, $R^4$ is methyl, $R^5$ is hydrogen, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is isopropyl, $R^4$ is methyl, $R^5$ is hydrogen, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is phenyl, $R^4$ is methyl, $R^5$ is hydrogen, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is cyclohexyl, $R^4$ is methyl, $R^5$ is hydrogen, and $R^6$ is hydrogen.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, $R^3$ is chosen from hydrogen, methyl, ethyl, n-propyl, isopropyl, phenyl, and cyclohexyl, $R^4$ is hydrogen, $R^5$ is chosen from methyl and hydroxymethyl, and $R^6$ is hydrogen, or $R^5$ and $R^6$ together with the carbon atom to which they are bonded form a 1,1-cyclopropane ring.

In certain embodiments of the compounds of Formula (I), $R^1$ is chosen from methyl, ethyl, n-propyl, isopropyl, n-butyl, isobutyl, sec-butyl, tert-butyl, phenyl, o-tolyl, cyclohexyl, and styryl, $R^2$ is hydrogen, and $R^3$ is chosen from hydrogen, methyl, ethyl, n-propyl, isopropyl, phenyl, and cyclohexyl, $R^4$ is methyl, $R^5$ is hydrogen, and $R^6$ is hydrogen.

In certain embodiments of the compounds of Formula (I) wherein $R^4$ is hydrogen, $R^5$ is hydroxymethyl, and $R^6$ is hydrogen; $R^1$ is chosen from $C_{1-4}$ alkyl, phenyl, substituted phenyl, cyclohexyl, and substituted cyclohexyl; $R^2$ is chosen from hydrogen, and $C_{1-4}$ alkyl; and $R^3$ is hydrogen.

In certain embodiments of the compounds of Formula (I) wherein $R^4$ is hydrogen, $R^5$ is hydroxymethyl, and $R^6$ is hydrogen; the compound is chosen from:
(2R)-3-hydroxy-2-{[2-methyl-1-(2-methylpropanoyloxy)
  propoxy]carbonylamino}propanoic acid;
(2R)-3-hydroxy-2-{[(2-methylpropanoyloxy)methoxy]
  carbonylamino}propanoic acid;
(2R)-3-hydroxy-2-[(pentanoyloxyethoxy)carbonylamino]
  propanoic acid;
(2R)-2-[(butanoyloxyethoxy)carbonylamino]-3-hydroxypropanoic acid;
(2R)-3-hydroxy-2-{[(2-methylpropanoyloxy)ethoxy]
  carbonylamino}propanoic acid;
(2R)-3-hydroxy-2-[(phenylcarbonyloxyethoxy)carbonylamino]propanoic acid;
(2R)-2-[(cyclohexylcarbonyloxyethoxy)carbonylamino]-3-hydroxypropanoic acid;
(2R)-3-hydroxy-2-{[(3-methylbutanoyloxy)ethoxy]
  carbonylamino}propanoic acid;
(2R)-3-hydroxy-2-{[(2-methylphenylcarbonyloxy)ethoxy]
  carbonylamino}propanoic acid;
(2R)-2-{[(2,2-dimethylpropanoyloxy)ethoxy]carbonylamino}-3-hydroxypropanoic acid;
(2R)-2-[(1-cyclohexylcarbonyloxy-2-methylpropoxy)carbonylamino]-3-hydroxypropanoic acid;
(2R)-3-hydroxy-2-[(2-methyl-1-phenylcarbonyloxypropoxy)carbonylamino]propanoic acid;
(2R)-2-[(heptanoyloxyethoxy)carbonylamino]-3-hydroxypropanoic acid;
a pharmaceutically acceptable salt of any of the foregoing, and a pharmaceutically acceptable solvate of any of the foregoing.

In certain embodiments of the compounds of Formula (I) wherein $R^4$ is hydrogen, $R^5$ and $R^6$ together with the carbon atom to which they are bonded form a 1,1-cyclopropane ring; $R^1$ is chosen from $C_{1-6}$ alkyl, phenyl, substituted phenyl, cyclohexyl, substituted cyclohexyl, $C_{7-9}$ phenylalkyl, and adamantyl; $R^2$ is chosen from hydrogen and $C_{1-4}$ alkyl; and $R^3$ is hydrogen.

In certain embodiments of the compounds of Formula (I) wherein $R^4$ is hydrogen, $R^5$ and $R^6$ together with the carbon atom to which they are bonded form a 1,1-cyclopropane ring; the compound is chosen from:
1-(1-isobutyryloxy-ethoxycarbonylamino)-cyclopropanecarboxylic acid;
1-(1-Isobutyryloxy-2-methyl-propoxycarbonylamino)-cyclopropanecarboxylic acid;
1-{[(2-methylphenylcarbonyloxy)ethoxy]
  carbonylamino}cyclopropanecarboxylic acid;
1-[(phenylcarbonyloxyethoxy)carbonylamino]cyclopropanecarboxylic acid;
1-[1-(3-methyl-butyryloxy)-ethoxycarbonylamino]-cyclopropanecarboxylic acid;
1-[1-(2,2-dimethyl-propionyloxy)-ethoxycarbonylamino]-cyclopropanecarboxylic acid;
1-(1-butyryloxy-ethoxycarbonylamino)-cyclopropanecarboxylic acid;
(1-pentanoyloxy-ethoxycarbonylamino)-cyclopropanecarboxylic acid;
1-isobutyryloxymethoxycarbonylaminocyclopropanecarboxylic acid;
1-[(cyclohexylcarbonyloxyethoxy)carbonylamino]cyclopropanecarboxylic acid;
1-[(1-cyclohexylcarbonyloxy-2-methylpropoxy)carbonylamino]cyclopropanecarboxylic acid;
1-[(2-methyl-1-phenylcarbonyloxypropoxy)carbonylamino]
  cyclopropanecarboxylic acid;
1-[(heptanoyloxyethoxy)carbonylamino]cyclopropanecarboxylic acid;
1-{[(3,4-dimethoxyphenylcarbonyloxy)ethoxy]
  carbonylamino}cyclopropanecarboxylic acid;
1-{[(4-phenylbutanoyloxy)ethoxy]
  carbonylamino}cyclopropanecarboxylic acid;
1-{[((2E)-3-phenylprop-2-enoyloxy)ethoxy]
  carbonylamino}cyclopropanecarboxylic acid;
1-{[2-methyl-1-(2-methylpropanoyloxy)propoxy]
  carbonylamino}sodium cyclopropanoate;
1-{[(2-phenylacetyloxy)ethoxy]
  carbonylamino}cyclopropanecarboxylic acid;
1-{[(4-methylphenylcarbonyloxy)ethoxy]
  carbonylamino}cyclopropanecarboxylic acid;
1-[(adamantanecarbonyloxyethoxy)carbonylamino]cyclopropanecarboxylic acid;
1-{[(3-phenylpropanoyloxy)ethoxy]
  carbonylamino}cyclopropanecarboxylic acid;
1-{[2-methyl-1-(3-phenylpropanoyloxy)propoxy]
  carbonylamino}cyclopropanecarboxylic acid;
a pharmaceutically acceptable salt of any of the foregoing, and a pharmaceutically acceptable solvate of any of the foregoing.

In certain embodiments of the compounds of Formula (I) wherein $R^4$ is methyl, $R^5$ is hydrogen, and $R^6$ is hydrogen; $R^1$ is chosen from $C_{1-6}$ alkyl, phenyl, substituted phenyl, cyclohexyl, and substituted cyclohexyl; $R^2$ is chosen from hydrogen, $C_{1-4}$ alkyl, phenyl, substituted phenyl, cyclohexyl, and substituted cyclohexyl; and $R^3$ is hydrogen.

In certain embodiments of the compounds of Formula (I) wherein $R^4$ is methyl, $R^5$ is hydrogen, and $R^6$ is hydrogen; the compound is chosen from:
2-{N-methyl[2-methyl-1-(2-methylpropanoyloxy)propoxy]
  carbonylamino}acetic acid;
2-{N-methyl[(2-methylpropanoyloxy)ethoxy]
  carbonylamino}acetic acid;
2-{N-methyl[(2-methylphenylcarbonyloxy)ethoxy]
  carbonylamino}acetic acid;
2-[N-methyl(phenylcarbonyloxyethoxy)carbonylamino]
  acetic acid;
2-{[(2,2-dimethylpropanoyloxy)ethoxy]-N-methylcarbonylamino}acetic acid;
2-[(cyclohexylcarbonyloxyethoxy)-N-methylcarbonylamino]acetic acid;
2-[N-methyl(pentanoyloxyethoxy)carbonylamino]acetic acid;

2-[(butanoyloxyethoxy)-N-methylcarbonylamino]acetic acid;

2-{N-methyl[(3-methylbutanoyloxy)ethoxy]carbonylamino}acetic acid;

2-{N-methyl[(2-methylpropanoyloxy)methoxy]carbonylamino}acetic acid;

2-[N-methyl(phenylphenylcarbonyloxymethoxy)carbonylamino]acetic acid;

2-[(1-cyclohexylcarbonyloxy-2-methylpropoxy)-N-methylcarbonylamino]acetic acid;

2-[N-methyl(2-methyl-1-phenylcarbonyloxypropoxy)carbonylamino]acetic acid;

2-[(heptanoyloxyethoxy)-N-methylcarbonylamino]acetic acid;

a pharmaceutically acceptable salt of any of the foregoing, and a pharmaceutically acceptable solvate of any of the foregoing.

In certain embodiments, the acyloxyalkyl carbamate prodrugs of Formula (I) are acyloxylalkyl carbamate prodrugs of D-serine, D-alanine, 1-aminocyclopropanecarboxylic acid, or sarcosine.

In certain embodiments, the acyloxyalkyl carbamate prodrugs of Formula (I) are colonically absorbable, e.g., the acyloxyalkyl carbamate prodrugs of Formula (I) are colonically absorbable forms of the corresponding α-amino acids. In certain embodiments, the acyloxyalkyl carbamate prodrugs of Formula (I) are a colonically absorbable form of an α-amino acid chosen from D-serine, D-alanine, 1-aminocyclopropanecarboxylic acid, and sarcosine.

In certain embodiments, the colonically absorbable forms of the α-amino acids provide an α-amino acid plasma AUC in a patient following colonic administration that is at least two times greater than the α-amino acid plasma AUC in the patient following colonic administration of an equivalent dose of the α-amino acid itself in an equivalent dosage form.

In certain embodiments, the compounds of Formula (I), when orally administered, provide an oral bioavailability of the corresponding α-amino acids in the plasma of a patient that is at least ten times greater than the oral bioavailability of the α-amino acid following oral administration of the α-amino acids themselves in an equivalent dosage form.

Synthesis

Methods for synthesis of acyloxyalkyl carbamate derivatives of amines are known in the art (see, for example, Alexander et al., U.S. Pat. No. 4,426,391; Alexander, U.S. Pat. No. 4,760,057; Lund, U.S. Pat. No. 5,401,868; Alexander, U.S. Pat. No. 4,760,057; Saari et al., European Patent 0416689B1; Mulvihill et al., Tetrahedron Lett. 2001, 7751-7754; Sun et al., Bioorg. Med. Chem. Lett. 2001, 11, 1875-1879; Sun et al., Bioorg. Med. Chem. Lett. 2001, 11, 3055-3059; Chen et al., PCT International Publication No. WO 01/05813; Mulvihill et al., Synthesis 2002, 3, 365-370; Gallop et al., U.S. Pat. No. 6,927,036; Raillard et al., U.S. Pat. No. 7,232,924; Bhat et al., U.S. Application Publication No. 2005/0070715; and Gallop et al., U.S. Pat. No. 7,227,028).

General synthetic methods useful in the synthesis of the compounds described herein are also available in the art (e.g., Wuts and Greene, "Protective Groups in Organic Synthesis," John Wiley & Sons, 4th ed. 2006; Harrison et al., "Compendium of Organic Synthetic Methods," Vols. 1-11, John Wiley & Sons 1971-2003; Larock "Comprehensive Organic Transformations," John Wiley & Sons, 2nd ed. 2000; and Paquette, "Encyclopedia of Reagents for Organic Synthesis," John Wiley & Sons, 11th ed. 2003).

Starting materials useful for preparing compounds provided by the present disclosure and intermediates thereof, and/or practicing the methods described herein are commercially available or can be prepared by well-known synthetic methods. Other methods for synthesis of the prodrugs of the present disclosure are either described in the art or will be readily apparent to those skilled in the art in view of the references provided herein and may be used to synthesize the compounds described herein. Accordingly, the methods presented herein are illustrative rather than comprehensive.

A method of synthesizing compounds of Formula (I), illustrated in Scheme 1, involves the reaction of an α-amino acid compound of Formula (III) with a 1-(acyloxy)-alkyl N-hydroxysuccinimidyl carbonate compound of Formula (II), as described in the co-pending application Gallop et al., U.S. Pat. No. 7,227,028, which is incorporated by reference herein in its entirety:

Scheme 1

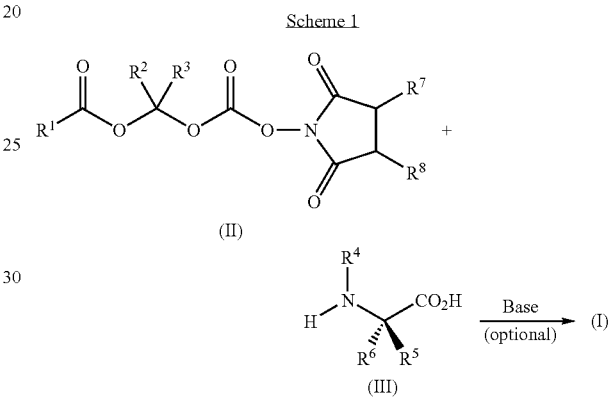

wherein, $R^1$ is chosen from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^2$ and $R^3$ are independently chosen from hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl, and substituted heteroarylalkyl; or $R^2$ and $R^3$, together with the carbon atom to which they are bonded, form a ring chosen from a cycloalkyl, substituted cycloalkyl, cycloheteroalkyl, and substituted cycloheteroalkyl ring;

$R^4$ is chosen from hydrogen and methyl;

$R^5$ is chosen from hydrogen, methyl, and hydroxymethyl;

$R^6$ is hydrogen, or $R^5$ and $R^6$, together with the carbon atom to which they are bonded, form a 1,1-cyclopropane ring; and $R^7$ and $R^8$ are independently chosen from hydrogen, acylamino, acyloxy, alkoxycarbonylamino, alkoxycarbonyloxy, alkyl, substituted alkyl, alkoxy, substituted alkoxy, aryl, substituted aryl, arylalkyl, substituted arylalkyl, carbamoyloxy, dialkylamino, heteroaryl, substituted heteroaryl, hydroxy, and sulfonamido, or $R^7$ and $R^8$, together with the atoms to which they are bonded, form a ring chosen from a substituted cycloalkyl, substituted cycloheteroalkyl, and substituted aryl ring.

In certain embodiments of the method of Scheme 1 for synthesizing a compound of Formula (I), each of $R^7$ and $R^8$ in the compound of Formula (II) is hydrogen.

In certain embodiments of the method described in Scheme 1 for synthesizing a compound of Formula (I), $R^2$ and $R^3$ in the compound of Formula (II) are different, such that the carbon atom to which these substituents are bonded is a stereogenic center.

In certain embodiments of methods of synthesizing a compound of Formula (I), $R^2$ and $R^3$ in the compound of Formula (I) are different and the compound of Formula (I) exists as substantially one enantiomer.

In certain embodiments of methods of synthesizing a compound of Formula (I), $R^2$ and $R^3$ in the compound of Formula (I) are different and the compound of Formula (I) exists as substantially one diastereomer.

In certain embodiments of the method of Scheme 1 for synthesizing a compound of Formula (I), each of $R^7$ and $R^8$ in the compound of Formula (II) is benzoyloxy, the stereochemistry at the carbon to which $R^7$ is bonded is of the R-configuration, and the stereochemistry at the carbon to which $R^8$ is bonded is of the R-configuration. In certain embodiments of the method of Scheme 1 for synthesizing a compound of Formula (I), each of $R^7$ and $R^8$ in the compound of Formula (II) is benzoyloxy, the stereochemistry at the carbon to which $R^7$ is bonded is of the S-configuration, and the stereochemistry at the carbon to which $R^8$ is bonded is of the S-configuration.

In certain embodiments, the method of Scheme 1 is carried out in a solvent. Solvents that may be used include, but are not limited to, acetone, acetonitrile, dichloromethane, dichloroethane, chloroform, toluene, tetrahydrofuran, dioxane, dimethylformamide, dimethylacetamide, N-methylpyrrolidinone, dimethyl sulfoxide, pyridine, ethyl acetate, methyl tert-butyl ether, methanol, ethanol, isopropanol, tert-butanol, water, and combinations of any of the foregoing. In certain embodiments, the solvent may be acetone, acetonitrile, dichloromethane, toluene, tetrahydrofuran, pyridine, methyl tert-butyl ether, methanol, ethanol, isopropanol, water, and combinations of any of the foregoing. In certain embodiments, the solvent may be a combination of acetonitrile and water. In certain embodiments, the solvent may be a combination of acetonitrile and water, with a volume ratio of acetonitrile to water ranging from about 1:5 to about 5:1. In certain embodiments, the solvent may be a combination of methyl tert-butyl ether and water. In certain embodiments, the solvent may be a combination of methyl tert-butyl ether and water, with a volume ratio of methyl tert-butyl ether to water ranging from about 2:1 to about 20:1. In certain embodiments, the solvent is a combination of methyl tert-butyl ether and water, wherein the methyl tert-butyl ether contains from about 10% to about 50% acetone by volume. In certain embodiments, the solvent is dichloromethane, water, or a combination thereof. In certain embodiments, the solvent is a biphasic combination of dichloromethane and water. In certain embodiments, the solvent is a biphasic combination of dichloromethane and water containing from about 0.001 equivalents to about 0.1 equivalents of a phase transfer catalyst. In certain embodiments, the phase transfer catalyst is a tetraalkylammonium salt, and in certain embodiments, the phase transfer catalyst is a tetrabutylammonium salt.

The method of Scheme 1 may be carried out a temperature ranging from about −20° C. to about 40° C. In certain embodiments, the temperature ranges from about −20° C. to about 25° C. In certain embodiments, the temperature ranges from about 0° C. to about 25° C. In certain embodiments, the temperature ranges from about 25° C. to about 40° C.

In certain embodiments of the method of Scheme 1, the reaction is performed in the absence of a base.

In certain embodiments of the method of Scheme 1, the reaction is performed in the presence of an inorganic base. In certain embodiments, the reaction is performed in the presence of an alkali metal bicarbonate or alkali metal carbonate salt. In certain embodiments, the reaction is performed in the presence of sodium bicarbonate.

In certain embodiments of the method of Scheme 1, the reaction is performed in the presence of an organic base. In certain embodiments, the reaction is performed in the presence of an organic base such as triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene, 1,5-diazabicyclo[4.3.0]undec-7-ene, and combinations of any of the foregoing. In certain embodiments, the reaction is performed in the presence of an organic base such as triethylamine, diisopropylethylamine, N-methylmorpholine, pyridine, or combinations of any of the foregoing.

In another embodiment, a compound of Formula (V), where $R^{10}$ is trialkylsilyl or aryldialkylsilyl, may be prepared directly from compound (III) by silylation (e.g., using a silyl halide or silylamide reagent) and then acylation of the resulting intermediate with compound (IV) (Scheme 2), where Z is a leaving group such as a halide, p-nitrophenolate, imidazolyl, and the like, and X is a halide, adapting methods disclosed by Gallop et al., U.S. Application Publication No. 2004/0014940, which is incorporated by reference herein in its entirety.

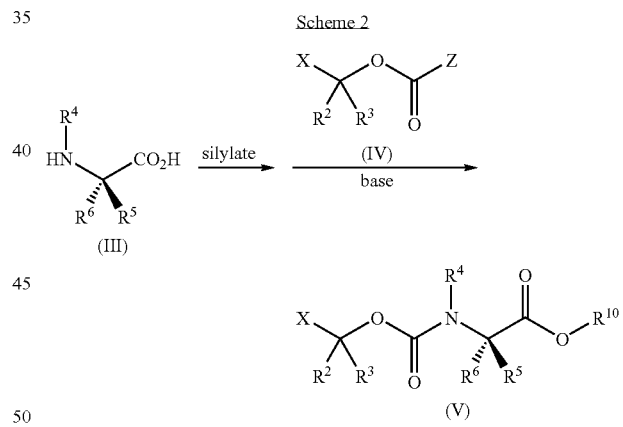

Scheme 2

Suitable solvents for performing this reaction include, for example, dichloromethane, dichloroethane, chloroform, toluene, pyridine, and acetonitrile. Suitable bases for performing this reaction include, for example, triethylamine, tributylamine, diisopropylethylamine, dimethylisopropylamine, N-methylmorpholine, N-methylpyrrolidine, N-methylpiperidine, pyridine, 2-methylpyridien, 2,6-dimethylpyridine, 4-dimethylaminopyridine, 1,4-diazabicyclo[2.2.2]octane, 1,8-diazabicyclo[5.4.0]undec-7-ene, and 1,5-diazabicyclo[4.3.0]undec-7-ene. The reaction can be performed at a temperature from about −78° C. to about 50° C., and in certain embodiments, at a temperature from about −20° C. to about 25° C.

1-Acyloxyalkylcarbamates of Formula (I) can be prepared from compounds of Formula (V) by treatment with carboxylic acids of the formula $R^1COOH$ in the presence of an organic or inorganic base, or other metal salt. Examples of useful solvents, bases and other reaction conditions are described in Gallop et al., U.S. Application Publication No. 2004/0014940. The carboxylic acid protecting group, $R^{10}$, can be removed under mild conditions to provide a compound of Formula (I) where $R^{10}$ is hydrogen. Carboxylic acid protecting groups removable via mild acidic hydrolysis, fluoride ion-promoted hydrolysis, catalytic hydrogenolysis, transfer hydrogenolysis, or other transition metal-mediated deprotection reactions. In certain embodiments, $R^{10}$ is trimethylsilyl.

Pharmaceutical Compositions

Pharmaceutical compositions provided by the present disclosure comprise a compound of Formula (I) and a pharmaceutically acceptable vehicle. The pharmaceutical compositions may comprise a therapeutically effective amount of compound of Formula (I) and at least one pharmaceutically acceptable vehicle. In certain embodiments, the pharmaceutical compositions may include more than one compound of Formula (I). Pharmaceutically acceptable vehicles include diluents, adjuvants, excipients, and carriers.

Pharmaceutical compositions may be produced using standard procedures (see, e.g., "Remington's The Science and Practice of Pharmacy," 21st edition, Lippincott, Williams & Wilcox, 2005). Pharmaceutical compositions may be manufactured by means of conventional mixing, dissolving, granulating, dragee-making, levigating, emulsifying, encapsulating, entrapping, and lyophilizing processes. Pharmaceutical compositions may be formulated in a conventional manner using one or more physiologically acceptable carriers, diluents, excipients, or auxiliaries, which facilitate processing of compounds disclosed herein into preparations, which may be used pharmaceutically. Proper formulation may depend, in part, on the route of administration.

Pharmaceutical compositions provided by the present disclosure may provide therapeutic or prophylactic levels of an α-amino acid upon administration to a patient. The promoiety of an α-amino acid prodrug may be cleaved in vivo either chemically and/or enzymatically to release the corresponding α-amino acid. One or more enzymes present in the intestinal lumen, intestinal tissue, blood, liver, brain, or any other suitable tissue of a mammal may enzymatically cleave the promoiety of the administered prodrugs. For example, the promoiety may be cleaved within the intestinal lumen and/or after absorption by the gastrointestinal tract (e.g., in intestinal tissue, blood, liver, or other suitable tissue of a mammal). In certain embodiments, the α-amino acid remains conjugated to the promoiety during transit across the intestinal mucosal barrier to provide protection from presystemic metabolism. In certain embodiments, the α-amino acid prodrug is essentially not metabolized to release the corresponding α-amino acid within enterocytes, but is metabolized to the parent drug within the systemic circulation. Cleavage of the promoiety of the α-amino acid prodrug after absorption by the gastrointestinal tract may allow the prodrug to be absorbed into the systemic circulation by active transport, passive diffusion, or by a combination of both active and passive processes.

Alpha-amino acid prodrugs may remain intact until after passage of the prodrug through a biological barrier, such as the blood-brain-barrier. In certain embodiments, α-amino acid prodrugs provided by the present disclosure can be partially cleaved, e.g., one or more, but not all, of the promoieties may be cleaved before passage through a biological barrier or prior to being taken up by a cell, tissue, or organ.

Alpha-amino acid prodrugs may remain intact in the systemic circulation and be absorbed by cells of an organ, either passively or by active transport mechanisms. In certain embodiments, the α-amino acid prodrugs are lipophilic and may passively translocate through cellular membranes. Following cellular uptake, the prodrugs may be cleaved chemically and/or enzymatically to release the corresponding α-amino acids into the cellular cytoplasm, resulting in an increase in the intracellular concentration of the α-amino acids. In certain embodiments, the prodrugs may be permeable to intracellular membranes such as the mitochondrial membrane, and thereby facilitate delivery of the prodrugs, and following cleavage of the promoiety or promoieties, an α-amino acid, to an intracellular organelle.

In certain embodiments, the pharmaceutical compositions comprise at least one compound of Formula (I) in an amount effective for the treatment of a neuropsychiatric or neurodegenerative disorder in a patient. In certain embodiments, the pharmaceutical compositions comprise at least one compound of Formula (I) in an amount effective for the treatment of a neuropsychiatric or neurodegenerative disorder associated with glutamatergic neurotransmission dysfunction. In certain embodiments; the pharmaceutical compositions comprise at least one compound of Formula (I) in an amount effective for the treatment of a neuropsychiatric or neurodegenerative disorder chosen from a psychotic disorder such as schizophrenia, schizophreniform disorder, schizoaffective disorder, delusional disorder, drug-induced psychotic disorder, or an illness associated with psychosis including major depression, bipolar disorder, and post-traumatic stress syndrome; a cognitive disorder such as dementia associated with, for example, Alzheimer's disease, Parkinson's disease, Huntington's disease, HIV, Pick's disease, and Creutzfeldt-Jakob disease, amnestic disorders, and age-related cognitive decline; an anxiety disorder such as generalized anxiety disorder, obsessive compulsive disorder, social phobia, panic attack, mood disorders including depression, seasonal depression, postpartum depression, premenstrual syndrome, and premenstrual dysphoric disorder; attention disorders including attention deficit hyperactivity disorder and autism; and movement disorders such as Parkinsonism, akinesias, akathesias, and dyskinesias including tardive dyskinesia, dystonia, spasticity, epilepsy, and Tourette's syndrome.

In certain embodiments, a pharmaceutical composition comprises at least one compound of Formula (I) in an amount effective for the treatment of a substance-related disorder or addictive behavior, including, for example, substance-induced delirium, persisting dementia, persisting amnestic disorder, psychotic disorder or anxiety disorder; or tolerance of, dependence on, or withdrawal from substances including alcohol, amphetamines, cannabis, cocaine, hallucinogens, inhalants, nicotine, opioids, phencyclidine, sedatives, hypnotics, and anxiolytics.

In certain embodiments, a pharmaceutical composition comprises at least one compound of Formula (I) in an amount effective for the treatment of obesity, bulimia nervosa, or a compulsive eating disorder.

In certain embodiments, the pharmaceutical compositions comprise at least one compound of Formula (I) in an amount effective for the treatment of a learning disorder, pervasive developmental disorder including autistic disorder, attention disorders including attention-deficit hyperactivity disorder (ADHD), or conduct disorder.

In certain embodiments, the pharmaceutical compositions comprise at least one compound of Formula (I) in an amount effective for the treatment of NMDA receptor-related disorders such as autism, depression, benign forgetfulness, childhood learning disorder, or closed head injury.

In certain embodiments, the pharmaceutical compositions comprise at least one compound of Formula (I) in an amount effective for the treatment of urinary incontinence, neuronal damage including ocular damage, retinopathy or macular degeneration of the eye, tinnitus, hearing impairment or loss, brain edema, emesis, or a sleep disorder including insomnia and narcolepsy.

In certain embodiments, the pharmaceutical compositions include an adjuvant that facilitates absorption of the at least one compound of Formula (I) through the gastrointestinal epithelia. Such enhancers can, for example, open the tight-junctions in the gastrointestinal tract or modify the effect of cellular components, such as p-glycoprotein and the like. Suitable enhancers include alkali metal salts of salicylic acid, such as sodium salicylate, caprylic or capric acid, such as sodium caprylate or sodium caprate, and the like. Suitable enhancers also include, for example, bile salts, such as sodium deoxycholate. Various p-glycoprotein modulators are described in Fukazawa et al., U.S. Pat. No. 5,112,817 and Pfister et al., U.S. Pat. No. 5,643,909. Various absorption enhancing compounds and materials are described in Burnside et al., U.S. Pat. No. 5,824,638, and Meezam et al., U.S. Application Publication No. 2006/0046962. Other adjuvants that enhance permeability of cellular membranes include resorcinol, surfactants, polyethylene glycol, and bile acids.

In certain embodiments, the pharmaceutical compositions include an adjuvant that reduces enzymatic degradation of the at least one compound of Formula (I). Microencapsulation using protenoid microspheres, liposomes, or polysaccharides may also be effective in reducing enzymatic degradation of administered compounds.

The pharmaceutical compositions may also include one or more pharmaceutically acceptable vehicles, including excipients, adjuvants, carriers, diluents, binders, lubricants, disintegrants, colorants, stabilizers, surfactants, fillers, buffers, thickeners, emulsifiers, wetting agents, and the like. Vehicles can be selected to alter the porosity and permeability of a pharmaceutical composition, alter hydration and disintegration properties, control hydration, enhance manufacturability, etc.

In certain embodiments, the pharmaceutical compositions are formulated for oral administration. Pharmaceutical compositions formulated for oral administration can provide for uptake of a compound of Formula (I) throughout the gastrointestinal tract, or even in a particular region or regions of the gastrointestinal tract. In certain embodiments, the pharmaceutical compositions may be formulated to enhance uptake a compound of Formula (I) from the upper gastrointestinal tract, and in certain embodiments, from the small intestine. Such compositions may be prepared in a manner known in the pharmaceutical arts and may further comprise, in addition to a compound of Formula (I), one or more pharmaceutically acceptable vehicles, permeability enhancers, and/or a second therapeutic agent.

In certain embodiments, the pharmaceutical compositions further comprise a substance to enhance, modulate and/or control release, bioavailability, therapeutic efficacy, therapeutic potency, stability, etc., of a compound of Formula (I). For example, to enhance therapeutic efficacy a compound of Formula (I) may be co-administered with one or more active agents to increase the absorption or diffusion of the drug from the gastrointestinal tract, or to inhibit degradation of the drug in the systemic circulation. In certain embodiments, the compound of Formula (I) is co-administered with active agents having pharmacological effects that enhance the therapeutic efficacy of the compound of Formula (I).

Pharmaceutical compositions may take the form of solutions, suspensions, emulsions, tablets, pills, pellets, capsules, capsules containing liquids, powders, sustained-release formulations, suppositories, emulsions, aerosols, sprays, suspensions, or any other form suitable for use.

Pharmaceutical compositions comprising a compound of Formula (I) may be formulated for oral administration. Pharmaceutical compositions for oral delivery may be in the form of tablets, lozenges, aqueous or oily suspensions, granules, powders, emulsions, capsules, syrups, or elixirs, for example. Orally administered compositions may comprise one or more optional agents, for example, sweetening agents such as fructose, aspartame, and saccharin; flavoring agents such as peppermint, oil of wintergreen, and cherry; coloring agents; and preserving agents, to provide a pharmaceutically palatable preparation. Moreover, when in tablet or pill form, the compositions may be coated to delay disintegration and absorption in the gastrointestinal tract, thereby providing a sustained action over an extended period of time. Oral compositions may include standard vehicles such as mannitol, lactose, starch, magnesium stearate, sodium saccharine, cellulose, magnesium carbonate, etc. Such vehicles may be of pharmaceutical grade.

For oral liquid preparations such as, for example, suspensions, elixirs, and solutions, suitable carriers, excipients or diluents include water, saline, alkyleneglycols (e.g., propylene glycol), polyalkylene glycols (e.g., polyethylene glycol), oils, alcohols, slightly acidic buffers having a pH ranging from about pH 4 to about pH 6 (e.g., acetate, citrate, ascorbate at between about 5 mM to about 50 mM), etc. Additionally, flavoring agents, preservatives, coloring agents, bile salts, acylcarnitines, and the like may be added.

When compounds of Formula (I) are acidic, they may be included in any of the above-described formulations as free acids, pharmaceutically acceptable salts, solvates, or hydrates. Pharmaceutically acceptable salts substantially retaining the activity of the free acid forms may be prepared by reaction with bases, and tend to be more soluble in aqueous and other protic solvents than the corresponding free acid forms. In some embodiments, sodium salts of a compound of Formula (I) are used in the above-described formulations.

Pharmaceutical compositions provided by the present disclosure may be formulated for parenteral administration including administration by injection, for example, into a vein (intravenously), an artery (intraarterially), a muscle (intramuscularly), under the skin (subcutaneously or in a depot formulation), to the pericardium, to the coronary arteries, or used as a solution for delivery to a tissue or organ, for example, use in a cardiopulmonary bypass machine or to bathe transplant tissues or organs. Injectable compositions may be pharmaceutical compositions for any route of injectable administration including, but not limited to, intravenous, intraarterial, intracoronary, pericardial, perivascular, intramuscular, subcutaneous, intradermal, intraperitoneal, and intraarticular. In certain embodiments, the injectable pharmaceutical compositions are pharmaceutically appropriate compositions for administration directly into the heart, pericardium or coronary arteries.

Pharmaceutical compositions provided by the present disclosure suitable for parenteral administration may comprise one or more compounds of Formula (I) in combination with one or more pharmaceutically acceptable sterile isotonic aqueous, water-miscible, or non-aqueous vehicles. Pharmaceutical compositions for parenteral use may include substances that increase and maintain drug solubility such as complexing agents and surface acting agents, compounds that make the solution isotonic or near physiological pH such as sodium chloride, dextrose, and glycerin, substances that enhance the chemical stability of solutions such as antioxidants, inert gases, chelating agents, and buffers, substances that enhance chemical and physical stability, substances that minimize self-aggregation or interfacial induced aggregation, substances that minimize protein interaction with interfaces, preservatives including antimicrobial agents, suspending agents, emulsifying agents, and combinations of any of the foregoing. Pharmaceutical compositions for parenteral administration may be formulated as solutions, suspensions, emulsions, liposomes, microspheres, nanosystems, and powder to be reconstituted as solutions. Parenteral preparations are described in "Remington, The Science and Practice of Pharmacy," 21 st edition, Lippincott, Williams & Wilkins, Chapter 41-42, pages 802-849, 2005.

For prolonged delivery, pharmaceutical compositions may be provided as depot preparations, for administration by implantation, e.g., subcutaneous, intradermal, or intramuscular injection. Thus, in certain embodiments, the pharmaceutical compositions are formulated with suitable polymeric or hydrophobic materials, e.g., as an emulsion in a pharmaceutically acceptable oil, ion exchange resins, or as a sparingly soluble derivative, e.g., as a sparingly soluble salt form of a compound of Formula (I).

Pharmaceutical compositions provided by the present disclosure may be formulated so as to provide immediate, sustained, or delayed release of a compound of Formula (I) after administration to the patient by employing procedures known in the art (see, e.g., Allen et al., "Ansel's Pharmaceutical Dosage Forms and Drug Delivery Systems," 8th ed., Lippincott, Williams & Wilkins, August 2004). In certain embodiments, pharmaceutical compositions comprising a compound of Formula (I) are formulated for sustained release, and in certain embodiments, for oral sustained release.

Dosage Forms

Pharmaceutical compositions provided by the present disclosure may be formulated in a unit dosage form. Unit dosage form refers to a physically discrete unit suitable as a unitary dose for patients undergoing treatment, with each unit containing a predetermined quantity of at least one compound of Formula (I) calculated to produce the intended therapeutic effect. A unit dosage form may be for a single daily dose, once or twice per day, or one of multiple daily doses, e.g., 2, 3, or 4 times per day. When multiple daily doses are used, the unit dosage may be the same or different for each dose. One or more dosage forms may comprise a dose, which can be administered to a patient at a single point in time or during a time interval.

Pharmaceutical compositions provided by the present disclosure may be used in dosage forms that provide immediate release and/or controlled release of the at least one compound of Formula (I). The appropriate type of dosage form will depend on the disease, disorder, or condition being treated, and on the method of administration. For example, for the treatment of an acute neuropsychiatric or neurodegenerative disorder an immediate release pharmaceutical composition or dosage form administered parenterally may be used. For treatment of chronic neuropsychiatric or neurodegenerative disorders, a controlled release pharmaceutical composition and/or dosage form administered orally may be used.

In certain embodiments, the dosage forms are adapted to be administered to a patient no more than twice per day, and in certain embodiments, only once per day. Dosing may be provided alone or in combination with other drugs, and may continue as long as required for effective treatment of the neuropsychiatric or neurodegenerative disorder.

Pharmaceutical compositions comprising the at least one compound of Formula (I) may be formulated for immediate release for parenteral administration, oral administration, or by any other appropriate route of administration.

Controlled drug delivery systems may be designed to deliver a drug in such a way that the drug level is maintained within the therapeutic windows and effective and safe blood levels are maintained for a period as long as the system continues to deliver the drug at a particular rate. Controlled drug delivery may produce substantially constant blood levels of a drug as compared to fluctuations observed with immediate release dosage forms. For some drugs, maintaining a constant bloodstream and tissue concentration throughout the course of therapy is the most desirable mode of treatment. Immediate release of these drugs may cause blood levels to peak above the level required to elicit the desired response, which wastes the drug and may cause or exacerbate toxic side effects. Controlled drug delivery can result in optimum therapy, and may reduce the frequency of dosing as well as reduce the severity of side effects. Examples of controlled release dosage forms include dissolution controlled systems, diffusion controlled systems, ion exchange resins, osmotically controlled systems, erodable matrix systems, pH independent formulations, gastric retention systems, and the like.

In certain embodiments, the oral dosage forms of the present disclosure may be controlled release dosage forms. Controlled delivery technologies may improve the absorption of the drug in a particular region or regions of the gastrointestinal tract.

The appropriate oral dosage form for a particular pharmaceutical composition may depend, at least in part, on the gastrointestinal absorption properties of the compound of Formula (I), the stability of the compound of Formula (I) in the gastrointestinal tract, the pharmacokinetics of the compound of Formula (I), and the intended therapeutic profile. An appropriate controlled release oral dosage form may be selected for particular compounds of Formula (I). For example, gastric retention oral dosage forms may be appropriate for compounds absorbed primarily from the upper gastrointestinal tract, and sustained release oral dosage forms may be appropriate for compounds absorbed primarily from the lower gastrointestinal tract.

Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide the desired therapeutic effect.

Gastric retention dosage forms, i.e., dosage forms that are designed to be retained in the stomach for a prolonged period of time, may increase the bioavailability of drugs that are most readily absorbed by the upper gastrointestinal tract. The residence time of a conventional dosage form in the stomach ranges from 1 to 3 hours. After transiting the stomach, there is approximately a 3 to 5 hour window of bioavailability before the dosage form reaches the colon. However, if the dosage form is retained in the stomach, the drug may be released before it reaches the small intestine and will enter the intestine in solution in a state in which it can be more readily absorbed. Another use of gastric retention dosage forms is to improve the bioavailability of drugs that are unstable to the basic conditions of the intestine (see, e.g., Hwang et al., *Critical Reviews in Therapeutic Drug Carrier Systems*, 1998, 15, 243-284).

To enhance drug absorption from the upper gastrointestinal tract, several gastric retention dosage forms have been developed. Examples include, hydrogels (see, e.g., Gutierrez-Rocca et al., U.S. Application Publication No. 2003/0008007), buoyant matrices (see, e.g., Lohray et al., Application Publication No. 2006/0013876), polymer sheets (see, e.g., Mohammad, Application Publication No. 2005/0249798), microcellular foams (see, e.g., Clarke et al., Application Publication No. 2005/0202090), and swellable dosage forms (see, e.g., Edgren et al., U.S. Application Publication No. 2005/0019409; Edgren et al., U.S. Pat. No. 6,797,283; Jacob et al., U.S. Application Publication No. 2006/0045865; Ayres, U.S. Application Publication No. 2004/0219186; Gusler et al., U.S. Pat. No. 6,723,340; Flashner-Barak et al., U.S. Pat. No. 6,476,006; Wong et al., U.S. Pat. Nos. 6,120,803 and 6,548,083; Shell et al., U.S. Pat. No. 6,635,280; and Conte et al., U.S. Pat. No. 5,780,057).

In a swelling and expanding system, dosage forms that swell and change density in relation to the surrounding gastric content can be retained in the stomach for longer than a conventional dosage form. A dosage form can absorb water and swell to form a gelatinous outside surface and float on the surface of gastric content surface while maintaining integrity before releasing a drug. Fatty materials may be added to impede wetting and enhance flotation, for example, when hydration and swelling alone are insufficient. Materials that release gases may also be incorporated to reduce the density of the gastric retention dosage forms. Swelling also can significantly increase the size of a dosage form and thereby impede discharge of the non-disintegrated swollen solid dosage form through the pylorus into the small intestine. Swellable dosage forms may be formed by encapsulating a core containing drug and a swelling agent, or by combining a drug, swelling agent, and one or more erodible polymers.

Gastric retention dosage forms may also be in the form of a folded thin sheet containing a drug and water-insoluble diffusible polymer that opens in the stomach to its original size and shape, which is sufficiently large to prevent or inhibit passage of the expanded dosage from through the pyloric sphincter.

Floating and buoyancy gastric retention dosage forms may be designed to trap gases within sealed encapsulated cores that can float on the gastric contents, and thereby be retained in the stomach for a longer time, e.g., from about 9 to about 12 hours. Due to the buoyancy effect, these systems can provide a protective layer preventing the reflux of gastric content into the esophageal region and can also be used for controlled release devices. A floating system may, for example, contain hollow cores containing drug coated with a protective membrane. The trapped air in the cores floats the dosage from on the gastric content until the soluble ingredients are released and the system collapses. In other floating systems, cores comprise drug and chemical substances capable of generating gases when activated. For example, coated cores, comprising carbonate and/or bicarbonate can generate carbon dioxide from a reaction with hydrochloric acid in the stomach or incorporated organic acid in the system. The gas generated by the reaction is retained to float the dosage form. The inflated dosage form later collapses and clears form the stomach when the generated gas permeates slowly through the protective coating.

Bioadhesive polymers may also be used to provide a vehicle for controlled delivery of drugs to a number of mucosal surfaces in addition to the gastric mucosa (see, e.g., Mathiowitz et al., U.S. Pat. No. 6,235,313; and Illum et al., U.S. Pat. No. 6,207,197). A bioadhesive system can be designed by incorporation of a drug and other excipients within a bioadhesive polymer. On ingestion, the polymer hydrates and adheres to the mucus membrane of the gastrointestinal tract. Bioadhesive polymers can be selected that adhere to a desired region or regions of the gastrointestinal tract. Bioadhesive polymers can be selected to optimized delivery to targeted regions of the gastrointestinal tract including the stomach and small intestine. The mechanism of the adhesion is thought to be through the formation of electrostatic and hydrogen bonding at the polymer-mucus boundary. Jacob et al., U.S. Application Publication Nos. 2006/0045865 and 2005/0064027, disclose bioadhesive delivery systems which are useful for drug delivery to both the upper and lower gastrointestinal tract.

Ion exchange resins have also been shown to prolong gastric retention, potentially by adhesion.

Gastric retention oral dosage forms may be appropriately used for delivery of drugs that are absorbed mainly from the upper gastrointestinal tract. For example, certain compounds of Formula (I) may exhibit limited colonic absorption, and be absorbed primarily from the upper gastrointestinal tract. Thus, dosage forms that release the compound of Formula (I) in the upper gastrointestinal tract and/or retard transit of the dosage form through the upper gastrointestinal tract will tend to enhance the oral bioavailability of the compound of Formula (I). Other forms of $\alpha$-amino acids disclosed herein may be appropriately used with gastric retention dosage forms.

Polymer matrices have also been used to achieve controlled release of drugs over a prolonged period of time. Such sustained or controlled release may be achieved by limiting the rate by which the surrounding gastric fluid can diffuse through the matrix and reach the drug, dissolve the drug and diffuse out again with the dissolved drug, or by using a matrix that slowly erodes, continuously exposing fresh drug to the surrounding fluid. Disclosures of polymer matrices that function by these methods are found, for example, in Skinner, U.S. Pat. Nos. 6,210,710 and 6,217,903; Rencher et al., U.S. Pat. No. 5,451,409; Kim, U.S. Pat. No. 5,945,125; Kim, PCT International Publication No. WO 96/26718; Ayer et al., U.S. Pat. No. 4,915,952; Akhtar et al., U.S. Pat. No. 5,328,942; Fassihi et al., U.S. Pat. No. 5,783,212; Wong et al., U.S. Pat. No. 6,120,803; and Pillay et al., U.S. Pat. No. 6,090,411.

Other drug delivery devices that remain in the stomach for extended periods of time include, for example, hydrogel reservoirs comprising particles (Edgren et al., U.S. Pat. No. 4,871,548); swellable hydroxypropylmethylcellulose polymers (Edgren et al., U.S. Pat. No. 4,871,548); planar bioerodible polymers (Caldwell et al., U.S. Pat. No. 4,767,627); plurality of compressible retention arms (Curatolo et al., U.S. Pat. No. 5,443,843); hydrophilic water-swellable, cross-linked polymer particles (Shell, U.S. Pat. No. 5,007,790); and albumin-cross-linked polyvinylpyrrolidone hydrogels (Park et al., *J. Controlled Release* 1992, 19, 131-134).

In certain embodiments, pharmaceutical compositions of the present disclosure are formulated into a number of different dosage forms, which may be adapted to provide sustained release of the compound of Formula (I) upon oral administration. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms may be used to release drugs over a prolonged time period and are useful when it is desired that a drug or drug form be delivered to the lower gastrointestinal tract. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art (see, for example, "Remington's Pharmaceutical Sciences," Lippincott, Williams & Wilkins, 21st edition, 2005, Chapters 46 and 47; Langer, Science 1990, 249, 1527-1533; and Rosoff, "Controlled Release of Drugs," 1989, Chapter 2).

In diffusion-controlled systems, a water-insoluble polymer controls the flow of fluid and the subsequent egress of dissolved drug from the dosage form. Both diffusional and dissolution processes are involved in release of drug from the dosage form. In reservoir devices, a core comprising a drug is coated with the polymer, and in matrix systems, the drug is dispersed throughout the matrix. Cellulose polymers such as ethylcellulose and cellulose acetate may be used in reservoir devices. Examples of materials useful in matrix systems include, but are not limited to, methacrylates, acrylates, polyethylene, acrylic acid copolymers, polyvinylchloride, high molecular weight polyvinylalcohols, cellulose derivates, and fatty compounds such as fatty acids, glycerides, and carnauba wax.

In dissolution-controlled systems, the rate of dissolution of the drug is controlled by slowly soluble polymers or by microencapsulation. Once the coating is dissolved, the drug becomes available for dissolution. By varying the thickness and/or the composition of the coating or coatings, the rate of drug release may be controlled. In some dissolution-controlled systems, a fraction of the total dose may comprise an immediate-release component. Dissolution-controlled systems include encapsulated/reservoir dissolution systems and matrix dissolution systems. Encapsulated dissolution systems may be prepared by coating particles or granules of drug with slowly soluble polymers of different thickness or by microencapsulation. Examples of coating materials useful in dissolution-controlled systems include, but are not limited to, gelatin, carnauba wax, shellac, cellulose acetate phthalate, and cellulose acetate butyrate. Matrix dissolution devices may be prepared, for example, by compressing a drug with a slowly soluble polymer carrier into a tablet form.

The rate of release of drug from osmotic pump systems is determined by the inflow of fluid across a semipermeable membrane into a reservoir, which contains an osmotic agent. The drug may be mixed with the agent or may be located in a reservoir. The dosage form contains one or more small orifices from which dissolved drug is pumped at a rate determined by the rate of entrance of water due to osmotic pressure. As osmotic pressure within the dosage form increases, the drug is released through the orifice(s). The rate of release is constant and may be controlled within tight limits yielding relatively constant plasma and/or blood concentrations of the drug. Osmotic pump systems may provide a constant release of drug independent of the environment of the gastrointestinal tract. The rate of drug release may be modified by altering the osmotic agent and the sizes of the one or more orifices.

The release of drug from erosion-controlled systems is determined by the erosion rate of a carrier matrix. Drug is dispersed throughout the polymer and the rate of drug release depends on the erosion rate of the polymer. The drug-containing polymer may degrade from the bulk and/or from the surface of the dosage form.

Sustained release oral dosage forms may be in any appropriate form for oral administration, such as, for example, in the form of tablets, pills, or granules. Granules may be filled into capsules, compressed into tablets, or included in a liquid suspension. Sustained release oral dosage forms may additionally include an exterior coating to provide, for example, acid protection, ease of swallowing, flavor, identification, etc.

In certain embodiments, sustained release oral dosage forms comprise a therapeutically effective amount of a compound of Formula (I) and a pharmaceutically acceptable vehicle. In certain embodiments, sustained release oral dosage forms comprise less than a therapeutically effective amount of a compound of Formula (I) and a pharmaceutically effective vehicle. Multiple sustained release oral dosage forms, each dosage form comprising less than a therapeutically effective amount of a compound of Formula (I), may be administered at a single time or over a period of time to provide a therapeutically effective dose or regimen for treating a neuropsychiatric or neurodegenerative disorder.

Sustained release oral dosage forms provided by the present disclosure can release the compound of Formula (I) from the dosage form to facilitate the ability of the compound of Formula (I) to be absorbed from an appropriate region of the gastrointestinal tract, for example, in the small intestine, or in the colon. In certain embodiments, the sustained release oral dosage form releases the compound of Formula (I) from the dosage form over a period of at least about 4 hours, for example, over at least about 8 hours, at least about 12 hours, at least about 16 hours, at least about 20 hours, and in certain embodiments, at least about 24 hours. In certain embodiments, a sustained release oral dosage form releases a compound of Formula (I) in a delivery pattern ranging from about 0 wt % to about 20 wt % in from about 0 to about 4 hours; from about 20 wt % to about 50 wt % in from about 0 to about 8 hours; from about 55 wt % to about 85 wt % in from about 0 to about 14 hours; and about 80 wt % to about 100 wt % in from about 0 to about 24 hours. In certain embodiments, a sustained release oral dosage form releases a compound of Formula (I) in a delivery pattern ranging from about 0 wt % to about 20 wt % in from about 0 to about 4 hours; from about 20 wt % to about 50 wt % in from about 0 to about 8 hours; from about 55 wt % to about 85 wt % in about from 0 to about 14 hours; and from about 80 wt % to about 100 wt % in from about 0 to about 20 hours. In certain embodiments, a sustained release oral dosage form releases a compound of Formula (I) from the dosage form in a delivery pattern of from about 0 wt % to about 20 wt % in from about 0 to about 2 hours; from about 20 wt % to about 50 wt % in from about 0 to about 4 hours; from about 55 wt % to about 85 wt % in from about 0 to about 7 hours; and from about 80 wt % to about 100 wt % in from about 0 to about 8 hours.

Sustained release oral dosage forms comprising a compound of Formula (I) may provide a concentration of the corresponding α-amino acid in the plasma, blood, or tissue of a patient over time, following oral administration to the patient. The concentration profile of an α-amino acid can exhibit an AUC that is proportional to the dose of the corresponding compound of Formula (I).

Regardless of the specific type of controlled release oral dosage form used, a compound of Formula (I) may be released from an orally administered dosage form over a sufficient period of time to provide prolonged therapeutic concentrations of a compound of Formula (I) in the plasma and/or blood of a patient. Following oral administration, a dosage form comprising a compound of Formula (I) may provide a therapeutically effective concentration of the corresponding an α-amino acid in the plasma and/or blood of a patient for a continuous time period for at least about 4 hours, for example, for at least about 8 hours, for at least about 12 hours, for at least about 16 hours, and in certain embodiments, for at least about 20 hours, following oral administration of the dosage form to the patient. The continuous time periods during which a therapeutically effective concentration of an α-amino acid is maintained may be the same or different. The continuous period of time during which a therapeutically effective plasma concentration of an α-amino acid is maintained may begin shortly after oral administration or after a time interval.

In certain embodiments, an oral dosage for treating a disease, disorder, or condition in a patient comprises a compound of Formula (I) wherein the oral dosage form is adapted to provide, after a single administration of the oral dosage form to the patient, a therapeutically effective concentration of the corresponding α-amino acid in the plasma of the patient for a first continuous time period chosen from at least about 4 hours, for example, at least about 8 hours, at least about 12 hours, and at least about 16 hours, and at least about 20 hours.

Regardless of the specific type of sustained release oral dosage form used, compounds may be released from the dosage form over a period of at least about 4 hours, for example, over a period of at least about 8 hours, or over a period of at least about 12 hours. Further, in certain embodiments, a dosage form can release from about 0 to about 30% of the prodrug in from about 0 to about 2 hours, from about 20 to about 50% of the prodrug in from about 2 to about 12 hours, from about 50 to about 85% of the prodrug in from about 3 to about 20 hours and greater than about 75% of the prodrug in from about 5 to about 18 hours. In certain embodiments, the sustained release oral dosage form provides a concentration of α-amino acid in the blood plasma of a patient over time, which curve has an AUC proportional to the dose of the prodrug of α-amino acid administered, and a maximum concentration $C_{max}$. In certain embodiments, the $C_{max}$ is less than about 75%, and in certain embodiments, is less than about 60%, of the $C_{max}$ obtained from administering an equivalent dose of the compound from an immediate release oral dosage form, and the AUC is substantially the same as the AUC obtained from administering an equivalent dose of the prodrug from an immediate release oral dosage form.

In certain embodiments, a dosage form is administered once or twice per day, and in certain embodiments, once per day.

Uses of Compounds, Compositions, and Dosage Forms

Compounds of Formula (I) and pharmaceutical compositions comprising compounds of Formula (I) have utility in treating neurological and psychiatric disorders associated with glutamatergic neurotransmission dysfunction, including one or more of the following conditions and diseases: schizophrenia or psychosis including schizophrenia (e.g., paranoid, disorganized, catatonic, or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid and schizotypal personality disorders, illness associated with psychosis (such as major depression, manic depressive (bipolar) disorder, Alzheimer's disease, and post-traumatic stress syndrome), including the positive, negative, and cognitive symptoms of schizophrenia and other psychoses; cognitive disorders including dementia (associated with Alzheimer's disease, ischemia, multi-infarct dementia, trauma, vascular problems and stroke, HIV disease, Parkinson's disease, Huntington's disease, Pick's disease, Creutzfeldt-Jakob disease, perinatal hypoxia, other general medical conditions or substance abuse); delirium; amnestic disorders and age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder, and anxiety due to a general medical condition; substance-related disorders and addictive behaviors (including substance-induced delirium, persisting dementia, persisting amnestic disorder, psychotic disorder or anxiety disorder; tolerance of, dependence on, or withdrawal from substances including alcohol, amphetamines, cannabis, cocaine, hallucinogens, inhalants, nicotine, opioids, phencyclidine, sedatives, hypnotics, and anxiolytics); obesity, bulimia nervosa, and compulsive eating disorders; bipolar disorders; mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention disorders including attention-deficit hyperactivity disorder (ADHD) and conduct disorder; NMDA receptor-related disorders such as autism, depression, benign forgetfulness, childhood learning disorders and closed head injury; movement disorders, including akinesias and akinetic-rigid syndromes (including Parkinson's disease, drug-induced Parkinsonism, postencephalitic Parkinsonism, progressive supranuclear palsy, multiple system atrophy, corticobasal degeneration, Parkinsonism-ALS dementia complex and basal ganglia calcification), medication-induced Parkinsonism (such as neuroleptic-induced Parkinsonism, neuroleptic malignant syndrome, neuroleptic-induced acute dystonia, neuroleptic-induced acute akathisia, neuroleptic-induced tardive dyskinesia, and medication-induced postural tremor), Tourette's syndrome, epilepsy, muscular spasms, and disorders associated with muscular spasticity or weakness including tremors; dyskinesias (including tremor such as rest tremor, postural tremor, and intention tremor), chorea (such as Sydenham's chorea, Huntington's disease, benign hereditary chorea, neuroacanthocytosis, symptomatic chorea, drug-induced chorea, and hemiballism), myoclonus (including generalized myoclonus and focal myoclonus), tics (including simple tics, complex tics and symptomatic tics), and dystonia (including generalized dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp, and hemiplegic dystonia); urinary incontinence; neuronal damage including ocular damage, retinopathy or macular degeneration of the eye, tinnitus, hearing impairment or loss, and brain edema; emesis; and sleep disorders including insomnia and narcolepsy.

In certain embodiments, the treatable disorders are chosen from at least one of schizophrenia; bipolar disorder; depression including unipolar depression, seasonal depression and post-partum depression, premenstrual syndrome (PMS) and premenstrual dysphoric disorder (PDD); learning disorders, pervasive developmental disorder including autistic disorder; attention disorders including attention-deficit/hyperactivity disorder; autism; tic disorders including Tourette's syndrome; anxiety disorders including phobia and post-traumatic stress disorder; cognitive disorders associated with dementia, AIDS dementia, Alzheimer's disease, Parkinson's disease, and Huntington's disease; spasticity; myoclonus; muscle spasm; and tinnitus and hearing impairment and loss.

For example, the use of NMDA receptor agonists has been shown effective in treating the positive and cognitive or negative symptoms of schizophrenia (Tuomien et al., *Schizophrenia Research* 2005, 72, 225-234; Tsai et al., *Biol. Psychiatry* 2006, 59, 230-234; Lane et al., *Arch. Gen. Psychiatry* 2005, 62, 1196-1204; Tsai et al., *Biol. Psychiatry* 2004, 55, 452-456; van Berckel et al., *Biol. Psychiatry* 1996, 40, 1298-1300; Javitt, *Curr Opin Investig Drugs* 2002, 3(7), 1067-72; Millan, *Psychopharmacology (Berl.)* 2005, 179(1), 30-53; Javitt, *Curr Psychiatry Rep* 2001, 3(5), 413-417; Lane et al., *Arch. Gen. Psychiatry* 2005, 62, 1196-1204; and Bennett and Gronier, *Eur J Pharmacology* 2005, 527, 52-59), enhancing memory deficits (Andersen et al., *Neuropsychopharmacology* 2004, 29, 1080-1090), relieving anxiety (Richardson et al., *Learn. Mem.* 2004, 11, 510-516), reversing effects of alcohol (Rabe and Tabakoff, *Molecular Pharmacology* 1990, 38, 752-757), and treating ataxia (Ogawa, *Cerebellum* 2004, 3(2), 107-11; Ogawa et al., *J Neur Sci* 2003, 210, 53-56).

In certain embodiments, the present disclosure provides methods for treating cognitive disorders in a patient comprising administering to a patient in need of such treatment a therapeutically effective amount of a compound of Formula (I) or pharmaceutical composition thereof. Examples of cognitive disorders include dementia, delirium, amnestic disorders, and age-related cognitive decline. The text revision of the fourth edition of the Diagnostic and Statistical Manual of Mental Disorders (DSM-IV-TR, American Psychiatric Association, Washington D.C., 2000) provides a diagnostic tool that includes cognitive disorders including dementia, delirium, amnestic disorders and age-related cognitive decline. As used herein, the term "cognitive disorders" includes treatment of those mental disorders as described in DSM-IV-TR. The skilled artisan will recognize that there are alternative nomenclatures and classification systems for mental disorders, and that these systems evolve with medical and scientific progress. Thus, the term "cognitive disorders" is intended to include like disorders that are described in other diagnostic sources as well.

In certain embodiments, the present disclosure provides methods for treating anxiety disorders in a patient comprising administering to a patient in need of such treatment a therapeutically effective amount of a compound of Formula (I) or pharmaceutical composition thereof. Examples of anxiety disorders are generalized anxiety disorder, obsessive-compulsive disorder, and panic attack. The text revision of the fourth edition of the Diagnostic and Statistical Manual of Mental Disorders (DSM-IV-TR, American Psychiatric Association, Washington D.C., 2000) provides a diagnostic tool that includes anxiety disorders, generalized anxiety disorder, obsessive-compulsive disorder and panic attack. As used herein, the term "anxiety disorders" includes treatment of those mental disorders as described in DSM-IV-TR. The skilled artisan will recognize that there are alternative nomenclatures and classification systems for mental disorders, and that these systems evolve with medical and scientific progress. Thus, the term "anxiety disorders" is intended to include like disorders that are described in other diagnostic sources as well.

In certain embodiments, the present disclosure provides methods for treating schizophrenia or psychosis in a patient comprising administering to a patient in need of such treatment a therapeutically effective amount of a compound of Formula (I) or pharmaceutical composition thereof. Examples of schizophrenia or psychosis pathologies are paranoid, disorganized, catatonic or undifferentiated schizophrenia, and substance-induced psychotic disorder. The text revision of the fourth edition of the Diagnostic and Statistical Manual of Mental Disorders (DSM-IV-TR, American Psychiatric Association, Washington D.C., 2000) provides a diagnostic tool that includes paranoid, disorganized, catatonic, or undifferentiated schizophrenia, and substance-induced psychotic disorder. As used herein, the term "schizophrenia or psychosis" includes treatment of those mental disorders as described in DSM-IV-TR. The skilled artisan will recognize that there are alternative nomenclatures and classification systems for mental disorders, and that these systems evolve with medical and scientific progress. Thus, the term "schizophrenia or psychosis" is intended to include like disorders that are described in other diagnostic sources as well.

In certain embodiments, the present disclosure provides methods for treating substance-related disorders and addictive behaviors in a patient comprising administering to a patient in need of such treatment a therapeutically effective amount of a compound of Formula (I) or pharmaceutical composition thereof. Examples of substance-related disorders and addictive behaviors include persisting dementia, persisting amnestic disorder, psychotic disorder or anxiety disorder induced by substance abuse; and tolerance of, dependence on or withdrawal from substances of abuse. The text revision of the fourth edition of the Diagnostic and Statistical Manual of Mental Disorders (DSM-IV-TR, American Psychiatric Association, Washington D.C., 2000) provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes treatment of those mental disorders as described in DSM-IV-TR. The skilled artisan will recognize that there are alternative nomenclatures and classification systems for mental disorders, and that these systems evolve with medical and scientific progress. Thus, the term "substance-related disorders and addictive behaviors" is intended to include like disorders that are described in other diagnostic sources as well.

In certain embodiments, the present disclosure provides methods for treating pain in a patient comprising administering to a patient in need of such treatment a therapeutically effective amount of a compound of Formula (I) or a pharmaceutical composition thereof. Examples of pain include bone and joint pain such as osteoarthritis, repetitive motion pain, dental pain, cancer pain, myofascial pain such as muscular injury and fibromyalgia, perioperative pain such as general surgery and gynecological, chronic pain, and neuropathic pain.

In certain embodiments, the present disclosure provides methods for treating obesity and eating disorders associated with excessive food intake and complications associated therewith in a patient comprising administering to a patient in need of such treatment a therapeutically effective amount of a compound of Formula (I) or pharmaceutical composition thereof. Obesity is included in the tenth edition of the International Classification of Diseases and Related Health Problems (ICD-IO) (1992 World Health Organization) as a general medical condition. The text revision of the fourth edition of the Diagnostic and Statistical Manual of Mental Disorders (DSM-IV-TR, American Psychiatric Association, Washington D.C., 2000) provides a diagnostic tool that includes obesity in the presence of psychological factors affecting medical condition. As used herein, the term "obesity or eating disorders associated with excessive food intake" includes treatment of those medical conditions and disorders described in ICD-10 and DSM-IV-TR. The skilled artisan will recognize that there are alternative nomenclatures and classification systems for general medical conditions, and that these systems evolve with medical and scientific progress. Thus, the term "obesity or eating disorders associated with excessive food intake" is intended to include similar conditions and disorders that are described in other diagnostic sources as well.

In certain embodiments, methods provided by the present disclosure for treating neuropsychiatric and neurodegenerative disorders in a patient comprise administering to a patient in need of such treatment a therapeutically effective amount of a compound of Formula (I) or a pharmaceutical composition comprising a therapeutically effective amount of a compound of Formula (I). In certain embodiments, methods of the present disclosure comprise administering to a patient a therapeutically effective amount of a compound of Formula (I) or a pharmaceutical composition comprising a therapeutically effective amount of a compound of Formula (I) for treating neuropsychiatric and/or neurodegenerative disorder chosen from a psychotic disorder such as schizophrenia, schizophreniform disorder, schizoaffective disorder, delusional disorder, drug-induced psychotic disorder, or an illness associated with psychosis including major depression, bipolar disorder, and post-traumatic stress syndrome; a cognitive disorder such as dementia associated with, for example, Alzheimer's disease, Parkinson's disease, Huntington's disease, HIV, Pick's disease, and Creutzfeldt-Jakob disease, amnestic disorders, and age-related cognitive decline; an anxiety disorder such as generalized anxiety disorder, obsessive compulsive disorder, social phobia, panic attack, mood disorders including depression, seasonal depression, postpartum depression, premenstrual syndrome, and premenstrual dysphoric disorder, attention disorders including attention deficit hyperactivity disorder, and autism; or a movement disorder such as Parkinsonism, akinesias, akathesias, and dyskinesias including tardive dyskinesia, dystonia, spasticity, epilepsy, and Tourette's syndrome.

In certain embodiments, the present disclosure provides methods for treating a dyskinesia in a patient comprising administering to a patient in need of such treatment a therapeutically effective amount of a compound of Formula (I) or a pharmaceutical composition thereof. Examples of dyskinesia include (including tremor such as rest tremor, postural tremor, and intention tremor), chorea (such as Sydenham's chorea, Huntington's disease, benign hereditary chorea, neuroacanthocytosis, symptomatic chorea, drug-induced chorea, and hemiballism), myoclonus (including generalized myoclonus and focal myoclonus), tics (including simple tics, complex tics and symptomatic tics), and dystonia (including generalized dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp, and hemiplegic dystonia).

In certain embodiments, the present disclosure provides methods for treating urinary incontinence in a patient comprising administering to a patient in need of such treatment a therapeutically effective amount of a compound of Formula (I) or a pharmaceutical composition thereof.

In certain embodiments, the present disclosure provides methods for treating neuronal damage in a patient comprising administering to a patient in need of such treatment a therapeutically effective amount of a compound of Formula (I) or a pharmaceutical composition thereof. Examples of neuronal damage include ocular damage, retinopathy, macular degeneration of the eye, tinnitus, hearing impairment or loss, and brain edema.

In certain embodiments, the present disclosure provides methods for treating emesis in a patient comprising administering to a patient in need of such treatment a therapeutically effective amount of a compound of Formula (I) or a pharmaceutical composition thereof.

In certain embodiments, the present disclosure provides methods for treating sleep disorders in a patient comprising administering to a patient in need of such treatment a therapeutically effective amount of a compound of Formula (I) or a pharmaceutical composition thereof. Sleep disorders are included in the tenth edition of the International Classification of Diseases and Related Health Problems (ICD-IO) (1992 World Health Organization) as a general medical condition. The text revision of the fourth edition of the Diagnostic and Statistical Manual of Mental Disorders (DSM-IV-TR, American Psychiatric Association, Washington D.C., 2000) provides a diagnostic tool that includes sleep disorder in the presence of psychological factors affecting medical condition and medical disorders. Examples of sleep disorders include primary insomnia, primary hypersomnia, narcolepsy, breathing-related sleep disorder, circadian rhythm sleep disorder, and other dyssomnias and parasomnias. The skilled artisan will recognize that there are alternative nomenclatures and classification systems for general medical conditions, and that these systems evolve with medical and scientific progress. Thus, the term "sleep disorder" is intended to include like conditions and disorders that are described in other diagnostic sources as well.

In certain embodiments, the present disclosure provides methods for treating a disease in a patient comprising administering to a patient in need of such treatment a therapeutically effective amount of a compound of Formula (I) or a pharmaceutical composition thereof, wherein the disease is chosen from post-partum depression, premenstrual syndrome, premenstrual dysphoric disorder, a learning disorder, autistic disorder, attention-deficit hyperactivity disorder, Tourette's syndrome, phobia, post-traumatic stress disorder, dementia, AIDS dementia, Alzheimer's disease, Parkinson's disease, Huntington's disease, spasticity, myoclonus, muscle spasm, tinnitus, hearing impairment, hearing loss, depression, anxiety, bipolar disorder, a substance abuse disorder, and urinary incontinence.

In certain embodiments, the present disclosure provides methods for treating a disease in a patient comprising administering to a patient in need of such treatment a therapeutically effective amount of a compound of Formula (I) or a pharmaceutical composition thereof, wherein the disease is schizophrenia.

The efficacy of the pharmaceutical compositions, dosage forms, and methods provided by the present disclosure for treating a disease disclosed herein may be determined by methods known to those skilled in the art. For example, one or more symptoms of a disease being treated can be measured before and after treatment of the patient. A reduction in such symptom(s) indicates that the patient's condition has improved. Improvement in the symptoms of the disease may be assessed using measures generally recognized in the art. The efficacy of pharmaceutical compositions, dosage forms and methods provided by the present disclosure may also be evaluated using animal models using methods recognized in the art.

For example, the efficacy of compounds of Formula (I) and pharmaceutical compositions of any of the foregoing for treating schizophrenia may be determined by methods known to those skilled in the art. For example, negative, positive, and/or cognitive symptom(s) of schizophrenia may be measured before, during, and/or after treating the patient. Reduction in such symptom(s) indicates that a patient's condition has improved. Improvement in the symptoms of schizophrenia may be assessed using, for example, the Scale for Assessment of Negative Symptoms (SANS), Positive and Negative Symptoms Scale (PANSS) (see, e.g., Andreasen, 1983, *Scales for the Assessment of Negative Symptoms* (SANS), Iowa City, Iowa; and Kay et al., *Schizophrenia Bulletin* 1987, 13, 261-276), and using Cognitive Deficits tests such as the Wisconsin Card Sorting Test (WCST) and other measures of cognitive function (see, e.g., Keshavan et al., *Schizophr Res* 2004, 70(2-3), 187-194; Rush, *Handbook of Psychiatric Measures*, American Psychiatric Publishing, 2000; Sajatovic and Ramirez, *Rating Scales in Mental Health*, 2nd ed, Lexi-Comp, 2003, Keefe, et al., *Schizophr Res.* 2004, 68(2-3), 283-97; and Keefe et al., *Neuropsychopharmacology*, 19 Apr. 2006).

The efficacy of Formula (I) and pharmaceutical compositions of any of the foregoing may be evaluated using animal models of schizophrenic disorders (see e.g., Geyer and Moghaddam, in "Neuropsychopharmacology," Davis et al., Ed., Chapter 50, 689-701, American College of Neuropsychopharmacology, 2002). For example, conditioned avoidance response behavior (CAR) and catalepsy tests in rats are shown to be useful in predicting antipsychotic activity and EPS effect liability, respectively (Wadenberg et al., *Neuropsychopharmacology*, 2001, 25, 633-641). Other and animal models of schizophrenia are disclosed, for example, in Sams-Dodd, *Rev Neurosci* 1999, 10(1), 59-90; Siuciak et al., *Neuropharmacology* 2007, 52, 279-290; Levkovitz et al., *Brain Res* 2007, 1154, 154-162; and Wang et al., *Neuropharmacology* 2007, 52, 1179-1187. Another useful animal model of schizophrenia is the PCP-induced hyperactivity model as described by Williams et al., *Progress Neuro-Pharmacology & Biological Psychiatry* 2006, 30, 239-243.

The efficacy of administering a compound of Formula (I) for treating Parkinson's disease may be assessed using animal and human models of Parkinson's disease and clinical studies. Animal and human models of Parkinson's disease are known (see, e.g., O'Neil et al., *CNS Drug Rev.* 2005, 11(1), 77-96; Faulkner et al., *Ann. Pharmacother.* 2003, 37(2), 282-6; Olson et al., *Am. J. Med.* 1997, 102(1), 60-6; Van Blercom et al., *Clin Neuropharmacol.* 2004, 27(3), 124-8; Cho et al., *Biochem. Biophys. Res. Commun.* 2006, 341, 6-12; Emborg, *J. Neuro. Meth.* 2004, 139, 121-143; Tolwani et al., *Lab Anim Sci* 1999, 49(4), 363-71; Hirsch et al., *J Neural Transin Suppl* 2003, 65, 89-100; Orth and Tabrizi, *Mov Disord* 2003, 18(7), 729-37; Betarbet et al., *Bioessays* 2002, 24(4), 308-18; and McGeer and McGeer, *Neurobiol Aging* 2007, 28(5), 639-647).

The efficacy of administering a compound of Formula (I) for treating Alzheimer's disease may be assessed using animal and human models of Alzheimer's disease and clinical studies. Useful animal models for assessing the efficacy of compounds for treating Alzheimer's disease are disclosed, for example, in Van Dam and De Dyn, Nature Revs Drug Disc 2006, 5, 956-970; Simpkins et al., *Ann N Y Acad Sci,* 2005, 1052, 233-242; Higgins and Jacobsen, *Behav Pharmacol* 2003, 14(5-6), 419-38; Janus and Westaway, *Physiol Behav* 2001, 73(5), 873-86; Bardgett et al., *Brain Res Bull* 2003, 60, 131-142; and Conn, ed., "Handbook of Models in Human Aging," 2006, Elsevier Science & Technology.

The efficacy of administering a compound of Formula (I) for treating Huntington's disease may be assessed using animal and human models of Huntington's disease and clinical studies. Animal models of Huntington's disease are disclosed, for example, in Riess and Hoersten, U.S. Application Publication No. 2007/0044162; Rubinsztein, *Trends in Genetics*, 2002, 18(4), 202-209; Matthews et al., *J. Neuroscience* 1998, 18(1), 156-63; Tadros et al., *Pharmacol Biochem Behav* 2005, 82(3), 574-82, and in Kaddurah-Daouk et al., U.S. Pat. No. 6,706,764 and U.S. Application Publication Nos. 2002/0161049, 2004/0106680, and 2007/0044162. An example of a placebo-controlled clinical trial evaluating the efficacy of creatine supplementation to treat Huntington's disease is disclosed in Verbessem et al., *Neurology* 2003, 61, 925-230.

Treatment of bipolar disorder can be assessed in clinical trials using rating scales such as the Montgomery-Asberg Depression Rating Scale, the Hamilton Depression Scale, the Raskin Depression Scale, Feighner criteria, and/or Clinical Global Impression Scale Score (Gijsman et al., *Am J Psychiatry* 2004, 161, 1537-1547; and Post et al., *J Clin Psychiatry* 2005, 66(3), 370-374).

Useful animal models for assessing treatment of anxiety include fear-potentiated startle (Brown et al., *J Experimental Psychol* 1951, 41, 317-327); elevated plus-maze (Pellow et al., *J Neurosci. Methods* 1985, 14, 149-167; and Hogg, *Pharmacol Biochem Behavior* 1996, 54(1), 21-20); fear-potentiated behavior in the elevated plus-maze test (Korte and De Boer, *Eur J Pharmacol* 2003, 463, 163-175); X-maze test of anxiety (Handley and Mithani, *Arch Pharmacol* 1984, 327, 1-5); and rat social interaction test (File, *J Neurosci Methods* 1980, 2, 219-238). Genetic animal models of anxiety are known (Toh, *Eur J Pharmacol* 2003, 463, 177-184) as are other animal models sensitive to anti-anxiety agents (Martin, *Acta Psychiatr Scand* 1998, Suppl 393, 74-80).

In clinical trials, efficacy can be evaluated using psychological procedures for inducing experimental anxiety applied to healthy volunteers and patients with anxiety disorders (see e.g., Graeff, et al., *Brazilian J Medical Biological Res* 2003, 36, 421-32) or by selecting patients based on the Structured Clinical interview for DSM-IV Axis I Disorders as described by First et al., Structured Clinical Interview for DSM-IV Axis I Disorders, Patient Edition (SCIDIP), Version 2. Biometrics Research, New York State Psychiatric Institute, New York, 1995. One or more scales can be used to evaluate anxiety and the efficacy of treatment including, for example, the Penn State Worry Questionnaire (Behar et al., *J Behav Ther Exp Psychiatry* 2003, 34, 25-43), the Hamilton Anxiety and Depression Scales, the Spielberger State-Trait Anxiety Inventory, and the Liebowitz Social Anxiety Scale (Hamilton, *J Clin Psychiatry* 1980, 41, 21-24; Spielberger and Vagg, *J Personality Assess* 1984, 48, 95-97; and Liebowitz, *J Clin Psychiatry* 1993, 51, 31-35 (Suppl)).

The efficacy of compounds provided by the present disclosure for treating depression can be evaluated in animal models of depression such as the forced swim test (Porsolt et al., *Nature* 1977, 266, 525-532; and Porsolt et al., *Arch Int Pharmacodyn* 1997, 229, 327-336), the tail suspension test (Cryan et al., *Trends Pharmacol Sci* 2002, 23, 238-245; and Cryan and Mombereau, *Mol Psychiatr* 2004, 9, 1050-1062), and well as other (Porsolt, *Rev. Neurosci* 2000, 11, 53-58).

Efficacy of tardive dyskinesia treatment can be assessed using animal models (Takeuchi et al., *Prog Neuro-Psychopharmacol & Biol Psychiat* 1998, 22, 679-691; Abilio et al., *Psychopharmacology* 2002, 161, 340-347; Queiroz and Frussa-Filho, *Prog Neuro-Psychopharmacol & Biol Psychiat* 1999, 23, 1405-1418; Andreassen et al., *Br J Pharmacol* 1996, 119(4), 751-7; Dutra et al., *Prog Neuro-Psychophar-*

*macology & Biol Psychiatry* 2002, 26, 487-495; and Shoham, *Brain Res* 2004, 1004, 142-147).

The efficacy of a compound of Formula (I) for the treatment of spasticity can be assessed using animal models of spasticity and in clinically relevant studies of spasticity of different etiologies. The therapeutic activity may be determined without determining a specific mechanism of action. Animal of spasticity are known (see e.g., Eaton, *J Rehab Res Dev* 2003, 40(4), 41-54; Kakinohana et al., *Neuroscience* 2006, 141, 1569-1583; Ligresti et al., *British J Pharm* 2006, 147, 83-91; Zhang et al., *Chinese J Clin Rehab,* 2006, 10(38), 150-151; Hefferan et al., *Neuroscience Letters* 2006, 403, 195-200; and Li et al., *J Neurophysiol* 2004, 92, 2694-2703). For example, animal models of spasticity include (a) the mutant spastic mouse (Chai et al., *Proc. Soc. Exptl. Biol. Med.* 1962, 109, 491); (b) the acute/chronic spinally transected rat and the acute decerebrate rat (see e.g., Wright and Rang, *Clin Orthop Relat Res* 1990, 253, 12-19; Shimizu et al., *J Pharmacol Sci* 2004, 96, 444-449; and Li et al., *J Neurophysiol* 2004, 92, 2694-2703); (c) primary observation Irwin Test in the rat (Irwin, *Psychopharmacologia* 1968, 13, 222-57); and d) Rotarod Test in the rat and mouse (Dunham et al., *J. Am. Pharm. Assoc.* 1957, 46, 208-09). Other animal models include spasticity induced in rats following transient spinal cord ischemia (Kakinohana et al., *Neuroscience* 2006, 141, 1569-1583; and Hefferan et al., *Neuroscience Letters* 2006, 403, 195-200), spasticity in mouse models of multiple sclerosis (Ligresti et al., *British J Pharmacol* 2006, 147, 83-91); and spasticity in rat models of cerebral palsy (Zhang et al., *Chinese J Clin Rehabilitation* 2006, 10(38), 150-151). The maximal electroshock seizure (MES) threshold test in rodents is sensitive for detecting potential anticonvulsant properties (Losher and Schmidt, *Epilepsy Res* 1988, 145-181). In this model, anticonvulsant agents elevate the threshold to electrically-induced seizures while proconvulsants lower the seizure threshold.

Methods of Administration and Doses

Methods for the treatment of diseases disclosed herein comprise administering at least one compound of Formula (I), or a pharmaceutically acceptable salt thereof, or a pharmaceutically acceptable solvate of any of the foregoing, or a pharmaceutical composition comprising any of the foregoing, to a patient in need of such treatment.

A compound of Formula (I), a pharmaceutically acceptable salt thereof, or a pharmaceutically acceptable solvate of any of the foregoing, or a pharmaceutical composition comprising any of the foregoing may be administered by any appropriate route. Examples of suitable routes of administration include, but are not limited to, intradermal, intramuscular, intraperitoneal, intravenous, subcutaneous, intranasal, epidural, oral, sublingual, intranasal, intracerebral, intravaginal, transdermal, rectally, inhalation, and topically. Administration may be systemic or local. Administration may be by bolus injection, continuous infusion, or by absorption through epithelial or mucocutaneous linings, e.g., oral mucosa, rectal, and intestinal mucosa, etc. Administration may be systemic or local. In certain embodiments, a compound of Formula (I), or pharmaceutical composition thereof, is administered orally.

In certain embodiments, compounds of Formula (I) or pharmaceutical compositions thereof, are delivered to patients via sustained release dosage forms, for example, via oral sustained release dosage forms, and in certain embodiments, are administered to a patient once or twice per day. When used to treat the diseases disclosed herein, a therapeutically effective amount of one or more compounds of Formula (I) may be administered or applied singly or in combination with other agents. A therapeutically effective amount of one or more compounds of Formula (I) may also deliver a corresponding α-amino acid in combination with another pharmaceutically active agent, including another compound of Formula (I). For example, in the treatment of a patient suffering from a neuropsychiatric or neurodegenerative disorder, a dosage form comprising a compound of Formula (I) may be administered in conjunction with a therapeutic agent known or believed to be capable of treating a neuropsychiatric or neurodegenerative disorder, at least one symptom of a neuropsychiatric or neurodegenerative disorder, or at least one condition associated with a neuropsychiatric or neurodegenerative disorder.

The amount of a compound of Formula (I) that will be effective in the treatment of a disease disclosed herein in a patient will depend, in part, on the nature of the condition and may be determined by standard clinical techniques known in the art. In addition, in vitro and in vivo assays may be employed to help identify optimal dosage ranges. A therapeutically effective amount of prodrug of Formula (I) to be administered may also depend on, among other factors, the subject being treated, the weight of the subject, the severity of the disease disclosed herein, the manner of administration, and the judgment of the prescribing physician.

For systemic administration, a therapeutically effective dose may be estimated initially from in vitro assays. For example, a dose can be formulated in animal models to achieve a beneficial circulating composition concentration range. Initial doses may also be estimated from in vivo data, e.g., animal models, using techniques that are known in the art. Such information can be used to more accurately determine useful doses in humans. One having ordinary skill in the art can optimize administration doses to humans based on animal data.

In some embodiments, oral sustained release dosage forms are adapted to be administered to a patient 1-3 times per day. In some embodiments, an oral sustained release dosage forms are adapted to be administered to a patient 1-2 times per day. In some embodiments, an oral sustained release dosage form is adapted to be administered once per day. Dosing may be provided alone or in combination with other drugs and may continue as long as required for effective treatment of a disease disclosed herein.

Suitable dosage ranges for oral administration are dependent on the potency of the particular α-amino acid (once cleaved from the promoiety) but may range from about 0.1 mg to about 200 mg of drug per kilogram body weight per day, for example, from about 1 to about 100 mg/kg-body wt per day. In certain embodiments, a compound of Formula (I) is administered to a patient in an amount ranging from about 10 mg-equivalents to about 3600 mg-equivalents of the corresponding α-amino acid per day, in certain embodiments, ranging from about 200 mg-equivalents to about 2400 mg-equivalents of the corresponding α-amino acid per day, and in certain embodiments, ranging from about 400 mg-equivalents to about 1600 mg-equivalents of the corresponding α-amino acid per day, to treat a disease disclosed herein. Dosage amounts and ranges may be readily determined by methods known to those skilled in the art.

A dose may be administered in a single dosage form or in multiple dosage forms. When multiple dosage forms are used, the amount of compound contained within each dosage form may be the same or different. The amount of a compound of Formula (I) contained in a dose may depend on the route of administration and whether the disease to be treated in a patient is effectively treated by acute, chronic, or a combination of acute and chronic administration.

In certain embodiments, an administered dose is less than a toxic dose. Toxicity of the compositions described herein may be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In certain embodiments, the pharmaceutical compositions exhibit a high therapeutic index. The data obtained from these cell culture assays and animal studies may be used in formulating a dosage range that is not toxic for use in humans. Doses of a pharmaceutical composition comprising a compound of Formula (I) may be within a range of circulating concentrations in, for example, the blood, plasma, and central nervous system, that include the effective dose and that exhibit little or no toxicity. A dose may vary within this range depending upon the dosage form employed and the route of administration utilized. In certain embodiments, an escalating dose is administered.

The efficacy of administering a compound of Formula (I) for treating a disease disclosed herein may be assessed using animal and human models of the diseases disclosed herein and with clinical results.

During treatment, a dose and dosing schedule may provide sufficient or steady state levels of an effective amount of an α-amino acid to treat a disease. In certain embodiments, an escalating dose is administered.

In certain embodiments, oral administration of an oral sustained release dosage form comprising a compound of Formula (I) provides a therapeutically effective concentration of an α-amino acid in the blood plasma of a patient for a time period of at least about 4 hours after administration of the dosage form, in certain embodiments, for a time period of at least about 8 hours, and in certain embodiments, for a time period of at least about 12 hours.

Combination Therapy

Compounds of Formula (I) may be used in combination with one or more other therapeutic agents in the treatment of diseases or disorders for which compounds of Formula (I) or the other therapeutic agents have utility, where the combination of the drugs together are safer or more effective than either drug alone. Such other drug(s) may be administered, by a route and in an amount commonly used therefore, contemporaneously or sequentially with a compound of Formula (I). When a compound of Formula (I) is used contemporaneously with one or more other drugs, a pharmaceutical composition in unit dosage form containing such other drugs and the compound of Formula (I) may be used. However, the combination therapy may also include therapies in which the compound of Formula (I) and one or more other drugs are administered on different overlapping schedules. It is also contemplated that when used in combination with one or more other active agents, compounds of Formula (I) and the other active agents may be used in lower doses than when each is used singly. Accordingly, pharmaceutical compositions provided by the present disclosure include those that comprise one or more other active therapeutic agents, in addition to a compound of Formula (I).

The above combinations may include combinations of a compound of Formula (I) not only with one other active compound, but also with two or more other active compounds. Likewise, compounds of Formula (I) may be used in combination with other drugs that are used in the treatment of the diseases or conditions for which compounds of Formula (I) are useful. Such other drugs may be administered, by a route and in an amount commonly used therefore, contemporaneously or sequentially with a compound of Formula (I). When a compound of Formula (I) is used contemporaneously with one or more other drugs, a pharmaceutical composition containing such other drugs in addition to the compound of Formula (I) may be used. Accordingly, the pharmaceutical compositions of the present disclosure include those that also contain one or more other active agents, in addition to a compound of Formula (I).

In certain embodiments, a compound of Formula (I), or pharmaceutically acceptable salt, or pharmaceutically acceptable solvate of any of the foregoing, may be used in combination therapy with at least one other therapeutic agent. A compound of Formula (I) and other therapeutic agent(s) may act additively or, and in certain embodiments, synergistically. In some embodiments, a compound of Formula (I) may be administered concurrently with the administration of another therapeutic agent. In some embodiments, the compound of Formula (I), a pharmaceutically acceptable salt, or a pharmaceutically acceptable solvate of any of the foregoing is administered prior or subsequent to administration of another therapeutic agent. Pharmaceutical compositions provided by the present disclosure may include, in addition to one or more compounds of Formula (I), one or more therapeutic agents effective for treating the same or different disease, disorder, or condition. Methods provided by the present disclosure include administration of one or more compounds of Formula (I) or pharmaceutical compositions comprising a compound of Formula (I) and one or more other therapeutic agents provided that the combined administration does not inhibit the therapeutic efficacy of the one or more compounds of Formula (I) and/or does not produce adverse combination effects.

In certain embodiments, compositions comprising a compound of Formula (I) are administered concurrently with the administration of another therapeutic agent, which may be part of the same pharmaceutical composition or dosage form as, or may be in a different composition or dosage form from, that containing the compounds of Formula (I). In certain embodiments, compounds of Formula (I) are administered prior or subsequent to administration of another therapeutic agent. In certain embodiments of combination therapy, the combination therapy comprises alternating between administering a composition comprising a compound of Formula (I) of the present disclosure and a composition comprising another therapeutic agent, e.g., to minimize adverse side effects associated with a particular drug. When a compound of Formula (I) is administered concurrently with another therapeutic agent that potentially may produce adverse side effects including, but not limited to, toxicity, the therapeutic agent may be administered at a dose that falls below the threshold at which the adverse side effect is elicited.

The weight ratio of a compound of Formula (I) to the second therapeutic agent may vary and depends upon the effective dose of each agent. Generally, a therapeutically effective dose of each compound will be used. Thus, for example, when a compound of Formula (I) is combined with another therapeutic agent, the weight ratio of the compound of Formula (I) to the second therapeutic agent may range from about 1000:1 to about 1:1000, and in certain embodiments, from about 200:1 to about 1:200.

Combinations of a compound of Formula (I) and a second therapeutic agent may also be within the aforementioned range, but in each case, an effective dose of each active compound may be used. In such combinations the compound of Formula (I) and the second therapeutic agent may be administered separately or in conjunction. In addition, the administration of one compound may be prior to, concurrent with, or subsequent to the administration of another therapeutic agent(s). Accordingly, compounds of Formula (I) may be used alone or in combination with other therapeutic agents that are known to be beneficial in the subject indications or other therapeutic agents that affect receptors or enzymes that either increase the efficacy, safety, convenience, or reduce unwanted side effects or toxicity of the compounds of Formula (I). A compound of Formula (I) and the other therapeutic agent may be co-administered, either in concomitant therapy or in a fixed combination. In certain embodiments, the compound of Formula (I) may be employed in combination with anti-Alzheimer's agents, beta-secretase inhibitors, gamma-secretase inhibitors, HMG-CoA reductase inhibitors, NSAIDs including ibuprofen, vitamin E, and anti-amyloid antibodies, and combinations thereof.

In certain embodiments, a compound of Formula (I) is administered in combination with an antipsychotic, an anti-depressant, an anxiolytic, an anti-anxiety agent, sedatives, or a hypnotic.

In certain embodiments, a compound of Formula (I) may be administered in combination with sedatives, hypnotics, anxiolytics, antipsychotics, anti-anxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as, for example, adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, salts of any of the foregoing, or combinations of any of the foregoing, or a compound of Formula (I) may be administered in conjunction with the use of physical methods such as with light therapy or electrical stimulation.

In certain embodiments, a compound of Formula (I) is administered in combination with levodopa (with or without a selective decarboxylase inhibitor such as carbidopa or benserazide), an anti-cholinergic such as biperiden and trihexyphenidyl (benzhexyl)hydrochloride, catechol-O-methyltransferase (COMT) inhibitors such as entacapone, monoamine oxidase-B (MOA-B) inhibitors, antioxidants, A2a adenosine receptor antagonists, cholinergic agonists, serotonin receptor antagonists, or dopamine receptor agonists such as alentemol, bromocriptine, fenoldopam, lisuride, naxagolide, pergolide, pramipexole, ropinirole, and rotigotine, pharmaceutically acceptable salts of any of the foregoing, or combinations of any of the foregoing.

In certain embodiments, a compound of Formula (I) is administered in combination with a compound chosen from a phenothiazine, thioxanthene, heterocyclic dibenzazepine, butyrophenone, diphenylbutylpiperidine, and indolone classes of neuroleptic agents. Examples of useful phenothiazines include chlorpromazine, mesoridazine, thioridazine, acetophenazine, fluphenazine, perphenazine, and trifluoperazine. Examples of useful thioxanthenes include chlorprothixene and thiothixene. An example of a useful dibenzazepine is clozapine. An example of a useful butyrophenone is haloperidol. An example of a useful diphenylbutylpiperidine is pimozide. An example of a useful indolone is molindolone. Other neuroleptic agents include loxapine, sulpiride, and risperidone. It will be appreciated that the neuroleptic agents when used in combination with a compound of Formula (I) may be in the form of a pharmaceutically acceptable salt. In certain embodiments, a compound of Formula (I) is administered in combination with acetophenazine, alentemol, aripiprazole, amisulpride, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine, ziprasidone, pharmaceutically acceptable salts of any of the foregoing, or combinations of any of the foregoing.

In certain embodiments, a compound of Formula (I) is administered in combination with an antipsychotic drug chosen from haloperidol, chlorpromazine, mesoridazine, thioridazine, acetophenazine, fluphenazine, trifluoperazine, clozapine, risperidone, olanzapine, quetiapine, ziprasidone, aripiprazole, and sertindole.

In certain embodiments, a compound of Formula (I) is administered in combination with an anti-depressant or anti-anxiety agent, including norepinephrine reuptake inhibitors such as tertiary amine tricyclics, and secondary amine tricyclics, selective serotonin reuptake inhibitors (SSRIs), monoamine oxidase inhibitors (MAOIs), reversible inhibitors of monoamine oxidase, serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, or 5-HT-IA agonists or antagonists, especially 5-HT-IA partial agonists, and corticotropin releasing factor (CRF) antagonists. Examples of anti-depressant and/or anti-anxiety agents include amitriptyline, clomipramine, doxepin, imipramine, trimipramine, amoxapine, desipramine, maprotiline, nortriptyline, protriptyline, fluoxetine, fluvoxamine, paroxetine, sertraline, isocarboxazid, phenelzine, tranylcypromine, selegiline, moclobemide, venlafaxine, duloxetine, aprepitant, bupropion, lithium, nefazodone, trazodone, viloxazine, alprazolam, chlordiazepoxide, clonazepam, chlorazepate, diazepam, halazepam, lorazepam, oxazepam, prazepam, buspirone, flesinoxan, gepirone, ipsapirone, pharmaceutically acceptable salts of any of the foregoing, or combinations of any of the foregoing.

In certain embodiments, a compound of Formula (I) is administered in combination with a compound useful for treating at least one of schizophrenia, bipolar disorder, depression including unipolar depression, seasonal depression and post-partum depression, premenstrual syndrome (PMS) and premenstrual dysphoric disorder (PDD), a learning disorder, pervasive developmental disorder including autistic disorder, an attention disorder including Attention-Deficit/Hyperactivity Disorder, autism, a tic disorder including Tourette's disorder, an anxiety disorder including phobia and post-traumatic stress disorder, cognitive disorders associated with dementia, AIDS dementia, Alzheimer's disease, Parkinson's disease, Huntington's disease, spasticity, myoclonus, muscle spasm, tinnitus, and hearing impairment or loss.

Examples of drugs useful for treating psychotic disorders include chlorpromazine, clozapine, fluphenazine, haloperidol, olanzapine, perphenazine, prochlorperazine, risperidone, and thiothixene. Examples of drugs useful for treating schizophrenia include apriprazole, loxapine, mesoridazine, quetiapine, reserpine, thioridazine, trifluoperazine, and ziprasidone. Examples of drugs useful for treating bipolar disorder include carbamazepine, clonazepam, clonidine, valproic acid, and verapamil. Examples of drugs useful for treating depression include alprazolam, amitriptyline, amoxapine, bupropion, citalopram, clomipramine, desipramine, doxepin, escitalopram, fluoxetine, fluvoxamine, imipramine, maprotiline, methylphenidate, mirtazapine, nefazodone, nortriptyline, paroxetine, protriptyline, sertraline, trazodone, and venlafaxine. Examples of drugs useful for treating premenstrual dysphoric disorder include fluoxetine, paroxetine, and sertraline. Examples of drugs useful for treating attention deficit disorder include amphetamine-dextroamphetamine, atomoxetine, bupropion, dexmethylphenidate, dextroamphetamine, methamphetamine, methylphenidate, and pemoline. Examples of drugs useful for treating Tourette's syndrome include haloperidol, pergolide, and pimozide. Examples of drugs useful for treating anxiety disorders include alprazolam, atenolol, gusiprone, chlordiazepoxide, clonidine, clorazepate, diazepam, doxepin, escitalopram, halazepam, hydroxyzine, lorazepam, nadolol, oxazepam, paroxetine, prochlorperazine, trifuoperazine, and venlafaxine. Examples of drugs useful for treating post-traumatic stress disorder include amitriptyline and sertraline. Examples of drugs useful for treating dementia include haloperidol. Examples of drugs useful for treating Alzheimer's disease include donepezil, galantamine, memantine, rivastigmine, and tacrine. Examples of drugs useful for treating Parkinson's disease include amantadine, benztropine, bromocriptine, carbidopa and levodopa, pergolide, pramipexole, ropinirole, selegiline, and trihexyphenidyl.

EXAMPLES

The following examples describe in detail preparation of compounds of Formula (I), methods of assessing compounds of Formula (I). It will be apparent to those skilled in the art that many modifications, both to materials and methods, may be practiced without departing from the scope of the disclosure.

In the examples below, the following abbreviations have the following meanings. If an abbreviation is not defined, it has its generally accepted meaning.

| DMSO = | dimethylsulfoxide |
| HPLC = | high pressure liquid chromatography |
| LC/MS = | liquid chromatography/mass spectroscopy |
| M = | molar |
| mL = | milliliter |
| mM = | millimolar |
| mmol = | millimoles |
| µg = | microgram |
| µL = | microliter |

-continued

| µM = | micromolar |
| v/v = | volume to volume |

General Experimental Protocols

O-(1-Acyloxyalkyl) S-alkylthiocarbonates are synthesized according to the procedures disclosed in Gallop et al., U.S. Application Publication No. 2005/0222431 (which is incorporated herein by reference in its entirety) and converted to the corresponding acyloxyalkyl N-hydroxysuccinimide carbonic acid esters as described therein, or according to the general procedure given below. All other reagents and solvents are purchased from commercial suppliers and used without further purification or manipulation.

Proton NMR spectra (400 MHz) are recorded on a Varian AS 400 NMR spectrometer equipped with an autosampler and data processing computation. DMSO-$d^6$ (99.9% D) or CDCl$_3$ (99.8% D) are used as solvents unless otherwise noted. The DMSO or chloroform solvent signal is used for calibration of the individual spectra (H. E. Gottlieb et al., J. Org. Chem., 1997, 62, 7512). Analytical LC/MS is performed on a Waters 2790 separation module equipped with a Waters Micromass QZ mass spectrometer, a Waters 996 photodiode detector, and a Merck Chromolith UM2072-027 or Phenomenex Luna C-18 analytical column. Mass-guided preparative HPLC purification of final compounds is performed on an instrument equipped with a Waters 600 controller, ZMD Micromass spectrometer, a Waters 2996 photodiode array detector, and a Waters 2700 Sample Manager. Acetonitrile/water gradients containing 0.05% formic acid are used as eluents in both analytical and preparative HPLC experiments.

General Procedure for the Synthesis of Acyloxyalkyl N-hydroxysuccinimide Carbonic Acid Esters A 250 mL round-bottomed flask equipped with a magnetic stir bar and a pressure-equilibrating dropping funnel was charged with 1-acyloxyalkyl alkylthiocarbonate (10 mmol) and N-hydroxysuccinimide (20-40 mmol). Dichloromethane (20-40 mL) was added and the reaction mixture cooled to ca. 0° C. in an ice bath. Peracetic acid (32 wt.-%) in a 40-45% aqueous acetic acid solution (30 mmol) was added drop wise to the cooled solution while stirring over a period of ca. one hour. After the addition was complete, the mixture is stirred for an additional three to five hours, and the reaction monitored using $^1$H NMR spectroscopy. After the starting material was completely, the reaction mixture was diluted with additional dichloromethane, and the organic solution washed successively with water (three times) and once with a 10% aqueous solution of sodium metabisulfite or sodium thiosulfate to quench any remaining oxidant. The combined organic extracts were dried over MgSO$_4$, filtered, and the solvent removed under reduced pressure with a rotary evaporator. Compound identity, integrity, and purity were determined using $^1$H NMR spectroscopy. The crude material was used directly in the next step, or was further purified using methods well known to those skilled in the art.

General Procedure for Synthesis of Acyloxyalkyl Carbamates of α-Amino Acids

A screw-capped 40 mL glass vial equipped with a magnetic stir bar was charged with an aqueous solution (5 mL) of an appropriate α-amino acid (2 mmol). The appropriate acyloxyalkyl N-hydroxysuccinimide carbonic acid ester (2 mmol) was added either as a solid or dissolved in a small volume of solvent (for oily materials). A mixture of acetonitrile and water (v/v=1:1) (15-20 mL) was added, and the reaction mixture stirred for ca. 12 hours at room temperature. Upon completion of the reaction, the mixture was diluted with ethyl acetate and 1N aqueous hydrochloric acid (ca. 10 mL). After vigorous mixing followed by phase separation, the aqueous layer was extracted once more with EtOAc, and the combined organic extracts were washed with brine. The solvents were evaporated under reduced pressure, the dry residue dissolved in a mixture of 60% (v/v) acetonitrile/water, and the solution filtered through a 0.2 μm nylon syringe filter. Final purification was done using mass-guided preparative HPLC. After lyophilization of the solvents, the pure compounds were obtained as a white powder or colorless wax.

General Procedure for One Pot Synthesis of Acyloxyalkyl Carbamates of α-Amino Acids Under an atmosphere of nitrogen, a dry 100 mL round-bottomed flask equipped with a magnetic stir bar and a rubber septum was charged with 1-aminocyclopropane-1-carboxylic acid (ACPC) (11.2 mmol). Anhydrous chloroform (10-15 mL) was added, and the reaction mixture cooled to ca. 0° C. in an ice bath. Neat chlorotrimethylsilane (22.4 mmol) was added at this temperature, followed by the slow addition of diisopropylethylamine (DIEA) (22.4 mmol). The reaction mixture was stirred at this temperature for ca. 30 min, at which time an appropriately substituted chloroalkylchloroformate (13.44 mmol) was added drop wise and in neat form. After the addition, the reaction mixture was warmed to ca. room temperature and stirred at this temperature for an additional 1 hour. A premixed mixture of DIEA (22.4 mmol) and an appropriately substituted carboxylic acid (22.4 mmol) was added at ca. room temperature. The reaction mixture was stirred overnight at 50° C. The chloroform was removed in vacuo using a rotary evaporator. The crude reaction product was diluted with methyl tert-butyl ether (MTBE), and the solution washed three times with water. The organic layer was dried over $MgSO_4$, and the filtrate evaporated in vacuo using a rotary evaporator. The crude dry residue was dissolved in a small amount of a mixture of 60% (v/v) acetonitrile/water (ca. 5 mL) and the solution filtered through a 0.2 μm nylon syringe filter. Final purification was done using mass-guided preparative HPLC. After lyophilization of the solvents, the pure compounds were generally obtained as solids or waxy materials.

Many of the chloroformates were commercially available and others chloroformates were synthesized following the procedure according to Coghlan and Caley, *Tetrahedron Letters* 1989, 30(16), 2033-2036.

Example 1

1-(1-Isobutyryloxy-ethoxycarbonylamino)-cyclopropanecarboxylic Acid (1)

Following the general procedure for the synthesis of acyloxyalkyl carbamates, ACPC (121 mg, 1.2 mmol) and (2,5-dioxoazolidinyloxycarbonyloxy)ethyl 2-methylpropanoate (273 mg, 1.0 mmol) were reacted to provide 123 mg (47% yield) of the title compound (1) as a white powder after work-up and mass-guided preparative HPLC purification. M.p.: 127.0-129.5° C. $^1$H NMR ($CDCl_3$, 400 MHz): δ=6.79 (q, 1H), 6.05 (br s, 0.2H), 5.41 (s, 0.8H), 2.52 (m, 1H), 1.61 (m, 2H), 1.48 (d, 3H), 1.28 (m, 2H), 1.18 (d, 6H). MS (ESI) m/z 277.17 $(M+NH_4)^+$; 282.12 $(M+Na)^+$; 258.13 $(M-H)^-$.

Example 2

1-(1-Isobutyryloxy-2-methyl-propoxycarbonylamino)-cyclopropanecarboxylic Acid (2)

Following the general procedure for the synthesis of acyloxyalkyl carbamates, ACPC (121 mg, 1.2 mmol) and 1-(2,5-dioxoazolidinyloxycarbonyloxy)-2-methylpropyl 2-methylpropanoate (301 mg, 1.0 mmol) were reacted to provide 148 mg (51% yield) of the title compound (2) as a white powder after work-up and mass-guided preparative HPLC purification. M.p.: 127.4-129.0° C. $^1$H NMR ($CDCl_3$, 400 MHz): δ=6.59 (d, 1H), 5.68 (br s, 0.3H), 5.39 (s, 0.7H), 2.58 (m, 1H), 2.01 (m, 1H), 1.61 (m, 2H), 1.30 (m, 2H), 1.19 (d, 3H), 1.18 (d, 3H), 0.99 (d, 6H). MS (ESI) m/z 305.20 $(M+NH_4)^+$; 310.15 $(M+Na)^+$; 286.21 $(M-H)^-$.

Example 3

1-{[(2-Methylphenylcarbonyloxy)ethoxy]carbonylamino}cyclopropanecarboxylic Acid (3)

Following the general procedure for the synthesis of acyloxyalkyl carbamates, ACPC (121 mg, 1.2 mmol) and (2,5-dioxoazolidinyloxycarbonyloxy)ethyl 2-methylbenzoate (321 mg, 1.0 mmol) were reacted to provide 133 mg (43% yield) of the title compound (3) as a white powder after work-up and mass-guided preparative HPLC purification. $^1$H NMR ($CDCl_3$, 400 MHz): δ=7.85 (d, 1H), 7.40 (t, 1H), 7.21 (t, 2H), 7.01 (q, 1H), 5.79 (br s, 0.3H), 5.41 (s, 0.7H), 2.58 (s, 3H), 1.60 (m, 5H), 1.30 (m, 2H). MS (ESI) m/z 325.17 $(M+NH_4)^+$; 330.12 $(M+Na)^+$; 306.15 $(M-H)^-$.

Example 4

1-[(Phenylcarbonyloxyethoxy)carbonylamino]cyclopropanecarboxylic Acid (4)

Following the general procedure for the synthesis of acyloxyalkyl carbamates, ACPC (121 mg, 1.1 mmol) and (2,5-dioxoazolidinyloxycarbonyloxy)ethyl benzoate (341 mg, 1.0 mmol) were reacted to provide 113 mg (35% yield) of the title compound (4) as a white powder after work-up and mass-guided preparative HPLC purification. M.p.: 173.8-175.8° C. $^1$H NMR ($CD_3CN$, 400 MHz): δ=8.00 (d, 2H), 7.61 (t, 1H), 7.50 (t, 2H), 6.99 (q, 1H), 6.31 (s, 0.8H), 6.01 (br s, 0.2H), 1.60 (d, 3H), 1.42 (m, 2H), 1.09 (m, 2H). MS (ESI) m/z 294.10 $(M+H)^+$; 311.12 $(M+NH_4)^+$; 316.11 $(M+Na)^+$; 292.12 $(M-H)^-$.

Example 5

1-[1-(3-Methyl-butyryloxy)-ethoxycarbonylamino]-cyclopropanecarboxylic Acid (5)

Following the general procedure for the synthesis of acyloxyalkyl carbamates, ACPC (121 mg, 1.2 mmol) and (2,5-dioxoazolidinyloxycarbonyloxy)ethyl 3-methylbutanoate (287 mg, 1.0 mmol) were reacted to provide 78 mg (28% yield) of the title compound (5) as a white powder after work-up and mass-guided preparative HPLC purification. M.p.: 116.6-119.1° C. $^1$H NMR ($CDCl_3$, 400 MHz): δ=6.80 (q, 1H), 6.05 (br s, 0.2H), 5.42 (s, 0.8H), 2.01-2.22 (m, 3H), 1.61 (m, 2H), 1.48 (d, 3H), 1.25 (m, 2H), 0.98 (d, 6H). MS (ESI) m/z 291.18 (M+NH$_4$)$^+$; 296.13 (M+Na)$^+$; 272.14 (M–H)$^-$.

Example 6

1-[1-(2,2-Dimethyl-propionyloxy)-ethoxycarbonylamino]-cyclopropanecarboxylic Acid (6)

Following the general procedure for the synthesis of acyloxyalkyl carbamates, ACPC (364 mg, 3.6 mmol) and (2,5-dioxoazolidinyloxycarbonyloxy)ethyl 2,2-dimethylpropanoate (862 mg, 3.0 mmol) were reacted to provide 472 mg (58% yield) of the title compound (6) as a white powder after work-up and mass-guided preparative HPLC purification. $^1$H NMR (CDCl$_3$, 400 MHz): δ=10.29 (br s, 1H), 6.68 (q, 1H), 6.41 (br s, 0.3H), 5.60 (s, 0.7H), 1.60 (m, 2H), 1.42 (m, 3H), 1.19 (s, 9H). MS (ESI) m/z 291.10 (M+NH$_4$)$^+$; 296.08 (M+Na)$^+$; 272.08 (M–H)$^-$.

Example 7

1-(1-Butyryloxy-ethoxycarbonylamino)-cyclopropanecarboxylic Acid (7)

Following the general procedure for the synthesis of acyloxyalkyl carbamates, ACPC (121 mg, 1.2 mmol) and (2,5-dioxoazolidinyloxycarbonyloxy)ethyl butanoate (273 mg, 1.0 mmol) were reacted to provide 61 mg (24% yield) of the title compound (7) as a white powder after work-up and mass-guided preparative HPLC purification. M.p.: 90.4-93.4° C. $^1$H NMR (CDCl$_3$, 400 MHz): δ=9.31 (br s, 1H), 6.80 (q, 1H), 6.20 (br s, 0.2H), 5.47 (s, 0.8H), 2.28 (m, 2H), 1.51-1.70 (m, 4H), 1.48 (d, 3H), 1.25 (m, 2H), 0.98 (t, 3H). MS (ESI) m/z 277.17 (M+NH$_4$)$^+$; 282.12 (M+Na)$^+$.

Example 8

1-(1-Pentanoyloxy-ethoxycarbonylamino)-cyclopropanecarboxylic Acid (8)

Following the general procedure for the synthesis of acyloxyalkyl carbamates, ACPC (121 mg, 1.2 mmol) and (2,5-dioxoazolidinyloxycarbonyloxy)ethyl pentanoate (287 mg, 1.0 mmol) were reacted to provide 153 mg (56% yield) of the title compound (8) as a white powder after work-up and mass-guided preparative HPLC purification. M.p.: 148.0-151.1° C. $^1$H NMR (CDCl$_3$, 400 MHz): δ=6.80 (q, 1H), 5.80 (br s, 0.2H), 5.40 (s, 0.8H), 2.31 (m, 2H), 1.52-1.70 (m, 4H), 1.47 (d, 3H), 1.20-1.40 (m, 4H), 0.91 (t, 3H). MS (ESI) m/z 291.15 (M+NH$_4$)$^+$; 296.12 (M+Na)$^+$; 272.12 (M–H)$^-$.

Example 9

1-Isobutyryloxymethoxycarbonylaminocyclopropanecarboxylic Acid (9)

Following the general procedure for the synthesis of acyloxyalkyl carbamates, ACPC (121 mg, 1.2 mmol) and (2,5-dioxoazolidinyloxycarbonyloxy)methyl 2-methylpropanoate (259 mg, 1.0 mmol) were reacted to provide 107 mg (44% yield) of the title compound (9) as a white powder after work-up and mass-guided preparative HPLC purification. $^1$H NMR (CDCl$_3$, 400 MHz): δ=5.99 (br s, 0.2H), 5.78 (br s, 0.4H), 5.73 (s, 1.6H), 5.59 (s, 0.8H), 2.59 (m, 1H), 1.62 (m, 2H), 1.31 (m, 2H), 1.19 (d, 6H). MS (ESI) m/z 246.10 (M+H)$^+$; 263.11 (M+NH$_4$)$^+$; 268.09 (M+Na)$^+$; 244.11 (M–H)$^-$.

Example 10

1-[(Cyclohexylcarbonyloxyethoxy)carbonylamino]cyclopropanecarboxylic Acid (10)

Following the general procedure for the synthesis of acyloxyalkyl carbamates, ACPC (426 mg, 4.2 mmol) and (2,5-dioxoazolidinyloxycarbonyloxy)ethyl cyclohexanecarboxylate (1.1 g, 3.5 mmol) were reacted to provide 172 mg (16% yield) of the title compound (10) as a white powder after work-up and mass-guided preparative HPLC purification. M.p.: 123.6-125.3° C. $^1$H NMR (CDCl$_3$, 400 MHz): δ=9.92 (br s, 1H), 6.76 (q, 1H), 6.34 (br s, 0.3H), 5.59 (s, 0.7H), 2.27 (m, 1H), 1.10-1.95 (m, 17H). MS (ESI) m/z 317.15 (M+NH$_4$)$^+$; 322.13 (M+Na)$^+$; 298.15 (M–H)$^-$.

Example 11

1-[(1-Cyclohexylcarbonyloxy-2-methylpropoxy)carbonylamino]cyclopropanecarboxylic Acid (II)

Following the general procedure for the synthesis of acyloxyalkyl carbamates, ACPC (0.533 g, 5.27 mmol) and 1-(2,5-dioxoazolidinyloxycarbonyloxy)-2-methylpropyl cyclohexanecarboxylate (1.5 g, 4.39 mmol) were reacted in the acetonitrile/water mixture to provide 0.368 g (27% yield) of the title compound (11) as a white powder after work-up and mass-guided preparative HPLC purification. M.p.: 156-158.5° C. $^1$H NMR (CDCl$_3$, 400 MHz): δ=6.59 (d, 1H), 6.05 (br s, 0.3H), 5.41 (s, 0.7H), 2.38 (m, 1H), 2.13 (m, 1H), 1.96 (d. 2H), 1.78 (m, 2H), 1.6 (m, 3H), 1.44 (m, 2H), 1.23 (m, 5H), 0.99 (m, 6H). MS (ESI) m/z 350.05 (M+Na)$^+$.

Example 12

1-[(2-Methyl-1-phenylcarbonyloxypropoxy)carbonylamino]cyclopropanecarboxylic Acid (12)

Following the general procedure for the synthesis of acyloxyalkyl carbamates, ACPC (0.726 g, 7.15 mmol) and 1-(2,5-dioxoazolidinyloxycarbonyloxy)-2-methylpropyl benzoate (2 g, 5.96 mmol) were reacted in the acetonitrile/water mixture to provide 0.445 g (25% yield) of the title compound (12) as a white powder after work-up and mass-guided preparative HPLC purification. $^1$H NMR (CDCl$_3$, 400 MHz): δ=8.02 (d, 2H), 7.59 (t, 1H), 7.42 (t, 2H), 6.82 (d, 1H), 5.56 (br s. 0.3H), 5.44 (s, 0.7H), 2.21 (m, 1H), 1.61 (m, 2H), 1.39 (m, 2H), 1.02 (dd, 6H). MS (ESI) m/z 344.19 (M+Na)$^+$.

Example 13

1-[(Heptanoyloxyethoxy)carbonylamino]cyclopropanecarboxylic Acid (13)

Following the general procedure for the synthesis of acyloxyalkyl carbamates, ACPC (0.530 g, 5.2 mmol) and (2,5-dioxoazolidinyloxycarbonyloxy)ethyl heptanoate (1 g, 4.03 mmol) were reacted to provide 0.148 g (15.4% yield) of the title compound (13) as a white powder after work-up and mass-guided preparative HPLC purification. M.p.: 112.6-113.2° C. $^1$H NMR (CDCl$_3$, 400 MHz): δ=6.79 (q, 1H), 5.81

(s, 0.2H), 5.4 (s, 0.8H), 2.3 (m, 2H), 1.64 (m, 4H), 1.51 (d, 3H), 1.32 (m, 8H), 0.98 (t, 3H). MS (ESI) m/z 324.05 (M+Na)⁺; 300.04 (M−H)⁻.

Example 14

1-{[(3,4-Dimethoxyphenylcarbonyloxy)ethoxy]carbonylamino}cyclopropanecarboxylic Acid (14)

Following the general procedure for the synthesis of acyloxyalkyl carbamates, ACPC (0.122 g, 1.21 mmol) and (2,5-dioxoazolidinyloxycarbonyloxy)ethyl 3,4-dimethoxybeanzoate (0.4 g, 1.01 mmol) were reacted to provide 0.260 g (68% yield) of the title compound (14) as a white powder after work-up and mass-guided preparative HPLC purification. M.p.: 171.8-173.6° C. ¹H NMR (CDCl₃, 400 MHz): δ=7.69 (d, 1H), 7.47 (s, 1H), 7.13 (d, 1H), 6.83 (d, 1H), 5.52 (s, 0.3H), 5.43 (s, 0.7H), 3.98 (d, 6H), 1.62 (m, 5H), 1.31 (br s, 2H). MS (ESI) m/z 375.99 (M+Na)⁺; 352.02 (M−H)⁻.

Example 15

1-{[(4-Phenylbutanoyloxy)ethoxy]carbonylamino}cyclopropanecarboxylic Acid (15)

Following the general procedure for the synthesis of acyloxyalkyl carbamates, ACPC (0.218 g, 2.08 mmol) and (2,5-dioxoazolidinyloxycarbonyloxy)ethyl 4-phenylbutyrate (0.607 g, 1.73 mmol) were reacted to provide 0.264 g (46% yield) of the title compound (15) as a white semi-solid after work-up and mass-guided preparative HPLC purification. ¹H NMR (CDCl₃, 400 MHz): δ=7.32 (t, 2H), 7.19 (m, 3H), 6.81 (q, 1H), 6.22 (s, 0.3H), 5.43 (s, 0.7H), 2.62 (t, 2H), 2.31 (m, 2H), 1.98 (q, 2H), 1.61 (m, 2H), 1.42 (dd, 3H), 1.23 (m, 2H). MS (ESI) m/z 358.05 (M+Na)⁺.

Example 16

1-{[((2E)-3-Phenylprop-2-enoyloxy)ethoxy]carbonylamino}cyclopropanecarboxylic Acid (16)

Following the general procedure for the one pot synthesis, ACPC (0.4 g, 3.9 mmol) was reacted with chlorotrimethylsilane (0.99 mL, 7.88 mmol) in anhydrous chloroform (10 mL) in the presence of DIEA (1.45 mL, 7.8 mmol). Subsequent reaction of the intermediate with 1-chloroethylchloroformate (0.83 mL, 5.85 mmol) followed by a mixture of DIEA (1.45 mL, 7.8 mmol) and trans-cinnamic acid (1.16 g, 7.88 mmol) provided 0.200 g (16.6% yield) of the title compound (16) as a buff-colored solid after aqueous work-up and mass-guided preparative HPLC purification. M.p: 169.3-172.2° C. ¹H NMR (CDCl₃, 400 MHz): δ=7.71-7.67 (d, 1H, J=15.6), 7.50 (d, 2H), 7.38 (m, 3H), 6.95 (q, 1H), 6.40 (d, 1H, J=16), 5.58 (s, 0.3H), 5.34 (s, 0.7H), 1.60-1.54 (m, 5H), 1.27-1.24 (m, 2H). MS (ESI) m/z 342.00 (M+Na)⁺; 318.02 (M−H)⁻.

Example 17

1-{[(3-Phenylpropanoyloxy)ethoxy]carbonylamino}cyclopropanecarboxylic Acid (17)

A dry 100 mL round-bottomed flask equipped with a magnetic stir bar and a rubber septum was charged with 1-{[((2E)-3-phenylprop-2-enoyloxy)ethoxy]carbonylamino}cyclopropanecarboxylic acid (16) (0.8 g, 2.5 mmols) and 10% palladium on carbon in 1:1 mixture of ethylacetate and ethanol. The reaction was done at 1 atm pressure under a hydrogen balloon at room temperature. After the reaction was complete, the solution was filtered through Celite and the solvents removed in vacuo using a rotary evaporator. The dry, crude residue was dissolved in a small amount of a mixture of 60% (v/v) acetonitrile/water (ca. 10 mL), and the solution filtered through a 0.2 μm nylon syringe filter. Final purification was achieved by mass-guided preparative HPLC. After lyophilization of the solvents, 0.646 g (80% yield) of the title compound (17) was obtained as a white solid. M.p: 132.9-134.4° C. ¹H NMR (CDCl₃, 400 MHz): δ=7.31 (t, 2H), 7.19 (t, 3H), 6.82 (q, 1H), 6.38 (s, 0.3H), 5.50 (s, 0.7H), 2.99 (t, 2H), 2.72 (m, 2H), 1.71 (m, 2H), 1.42 (d, 3H), 1.30 (m, 2H). MS (ESI) m/z 343.93 (M+Na)⁺, 319.96 (M−H)⁻.

Example 18

1-{[1-((2E)-3-Phenylprop-2-enoyloxy)-2-methylpropoxy]carbonylamino}cyclopropanecarboxylic Acid (18)

Following the general procedure for the one pot synthesis, ACPC (2.5 g, 24.6 mmol) was reacted with chlorotrimethylsilane (6.25 mL, 49.2 mmol) in anhydrous chloroform (25 mL) in the presence of DIEA (9.1 mL, 49.4 mmol). Subsequent reaction of the intermediate with 1-chloro-2-methylpropyl chloroformate (5.0 mL, 37 mmol) followed by a mixture of DIEA (9.1 mL, 49.4 mmol) and trans-cinnamic acid (7.1 g, 48 mmol) provided 0.406 g (12.2% yield) of the title compound (18) as a light-yellow solid after aqueous work-up and mass-guided preparative HPLC purification. M.p: 147.8-150.2° C. ¹H NMR (CDCl₃, 400 MHz): δ=7.72-7.68 (d, 1H, J=15.6), 7.51 (br s, 2H), 7.37 (m, 3H), 6.71 (d, 1H), 6.42 (d, 1H, J=16), 5.51 (s, 0.3H), 5.31 (s, 0.7H), 2.11 (m, 1H), 1.58 (m, 2H), 1.24 (m, 2H), 1.02 (d, 6H). MS (ESI) m/z 345.98 (M−H)⁻.

Example 19

1-{[2-Methyl-1-(3-phenylpropanoyloxy)propoxy]carbonylamino}cyclopropanecarboxylic Acid (19)

A dry 100 mL round-bottomed flask equipped with a magnetic stir bar and a rubber septum was charged with 1-{[1-((2E)-3-phenylprop-2-enoyloxy)-2-methylpropoxy]carbonylamino}cyclopropanecarboxylic acid (18) (0.62 g, 1.8 mmols) and 10% palladium on carbon in a 1:1 mixture of ethylacetate and ethanol. The reaction was done at 1 atm pressure under a hydrogen balloon at ca. room temperature. After the reaction was complete, the solution was filtered through Celite and the solvents removed in vacuo using a rotary evaporator. The dry, crude residue was dissolved in a small amount of a mixture of 60% (v/v) acetonitrile/water (ca. 10 mL), and the solution filtered through a 0.2 μm nylon syringe filter. Final purification was achieved by mass-guided preparative HPLC. After lyophilization of the solvents, the title compound (19) was obtained as a yellow semisolid (70% yield). ¹H NMR (CDCl₃, 400 MHz): δ=7.33 (t, 2H), 7.20 (m, 3H), 6.61 (d, 1H), 6.05 (s, 0.35H), 5.35 (s, 0.65H), 2.98 (t, 2H), 2.71 (m, 2H), 2.01 (m, 1H), 1.65 (m, 2H), 1.36 (m, 2H), 0.98 (d, 6H). MS (ESI) m/z 371.92 (M+Na)⁺; 348.01 (M−H)⁻.

Example 20

1-{[(2-Phenylacetyloxy)ethoxy]carbonylamino}cyclopropanecarboxylic Acid (20)

Following the general procedure for the one pot synthesis, ACPC (1.02 g, 9.8 mmol) was reacted with chlorotrimethylsilane (2.48 mL, 19.7 mmol) in anhydrous chloroform in the presence of DIEA (3.64 mL, 19.7 mmol). Subsequent reaction of the intermediate with 1-chloro-2-methylpropyl chloroformate (1.6 mL, 14.8 mmol) followed by a mixture of DIEA (3.64 mL, 19.7 mmol) and phenylacetic acid (2.6 g, 19.7 mmol) provided 0.560 g (14.4% yield) the title compound (20) as a yellow solid after aqueous work-up and mass-guided preparative HPLC purification. M.p: 142.1-145.6° C. $^1$H NMR (CDCl$_3$, 400 MHz): δ=7.33 (m, 5H), 6.81 (q, 1H), 5.31 (s, 1H), 3.61 (s, 2H), 1.63 (m, 2H), 1.47 (d, 3H), 1.28 (m, 2H). MS (ESI) m/z 330.08 (M+Na)$^+$.

Example 21

1-{[(4-Methylphenylcarbonyloxy)ethoxy]carbonylamino}cyclopropanecarboxylic Acid (21)

Following the general procedure for the one pot synthesis, ACPC (1.02 g, 9.8 mmol) was reacted with chlorotrimethylsilane (2.48 mL, 19.7 mmol) in anhydrous chloroform in the presence of DIEA (3.64 mL, 19.7 mmol). Subsequent reaction of the intermediate with 1-chloro-2-methylpropyl chloroformate (1.6 mL, 14.8 mmol) followed by a mixture of DIEA (3.64 mL, 19.7 mmol) and p-toluic acid (2.6 g, 19.7 mmol) provided 0.436 g (14.3% yield) the title compound (21) as a white solid after aqueous work-up and mass-guided preparative HPLC purification. M.p: 177.7-182.5° C. $^1$H NMR (CDCl$_3$, 400 MHz): δ=7.91 (d, 2H), 7.22 (m, 4H), 7.02 (q, 1H), 5.38 (s, 1H), 2.43 (s, 3H), 1.63 (m, 5H) 1.36 (m, 2H). MS (ESI) m/z 329.93 (M+H)$^+$; 305.97 (M−H)$^-$.

Example 22

1-[(Adamantanecarbonyloxyethoxy)carbonylamino]cyclopropanecarboxylic Acid (22)

Following the general procedure for the one pot synthesis, ACPC (1.02 g, 9.8 mmol) was reacted with chlorotrimethylsilane (2.48 mL, 19.7 mmol) in anhydrous chloroform in the presence of DIEA (3.64 mL, 19.7 mmol). Subsequent reaction of the intermediate with 1-chloro-2-methylpropyl chloroformate (1.6 mL, 14.8 mmol) followed by a mixture of DIEA (3.64 mL, 19.7 mmol) and admantane carboxylic acid (3.5 g, 19.7 mmol) provided 0.220 g (6.4% yield) of the title compound (22) as a white solid after aqueous work-up and mass-guided preparative HPLC purification. $^1$H NMR (CDCl$_3$, 400 MHz): δ=6.81 (q, 1H), 5.62 (s, 0.2H), 5.38 (s, 0.8H), 2.09 (m, 4H), 1.93 (m, 6H), 1.72 (m, 6H), 1.61 (s, 2H), 1.52 (d, 3H), 1.37 (br s, 2H). MS (ESI) m/z 374.01 (M+H)$^+$, M−H=350.04 (M−H)$^-$.

Example 23

1-{[2-Methyl-1-(2-methylpropanoyloxy)propoxy]carbonylamino}Sodium Cyclopropanoate (23)

A screw-capped 40 mL glass vial equipped with a magnetic stir bar was charged with 1-(1-isobutyryloxy-2-methyl-propoxycarbonylamino)-cyclopropanecarboxylic acid (2) (0.3 g, 1.04 mmol) in 4 mL of acetonitrile. An aqueous solution of sodium bicarbonate (0.0873 g, 1.044 mmol) in 4 mL water was added to the stirred solution and the mixture stirred for ca. 1 h at room temperature. The clear solution was frozen at −78° C. and the solution lyophilized to provide 0.325 g (99.4% yield) of the title compound (23) as a transparent solid. $^1$H NMR (D$_2$O, 400 MHz): δ=6.37 (d, 1H), 2.58 (m, 1H), 1.98 (m, 1H), 1.26 (m, 2H), 1.02 (m, 6H), 0.92 (m, 2H), 0.88 (m, 6H). MS (ESI) m/z 310.24 (M+H)$^+$.

Example 24

(2R)-2-{[(2,2-Dimethylpropanoyloxy)ethoxy]carbonylamino}-3-hydroxypropanoic Acid (24)

Following the general procedure for the synthesis of acyloxyalkyl carbamates, D-serine (504 mg, 4.8 mmol) and (2,5-dioxoazolidinyloxycarbonyloxy)ethyl 2,2-dimethylpropanoate (1.1 g, 4.0 mmol) were reacted to provide 305 mg (28% yield) of the title compound (24) as a white powder after work-up and mass-guided preparative HPLC purification. $^1$H NMR (CDCl$_3$, 400 MHz): δ=6.78 (m, 1H), 6.40 (br s, 1H), 6.11 (t, 1H), 4.41 (m, 1H), 4.04 (m, 1H), 3.93 (m, 1H), 1.44 (2d, 3H), 1.20 (s, 9H). MS (ESI) m/z 278.05 (M+H)$^+$; 295.06 (M+NH$_4$)$^+$; 300.04 (M+Na)$^+$; 276.04 (M−H)$^-$.

Example 25

(2R)-3-Hydroxy-2-{[(2-methylphenylcarbonyloxy)ethoxy]carbonylamino}propanoic Acid (25)

Following the general procedure for the synthesis of acyloxyalkyl carbamates, D-serine (252 mg, 2.4 mmol) and (2,5-dioxoazolidinyloxycarbonyloxy)ethyl 2-methylbenzoate (642 mg, 2.0 mmol) were reacted to provide 203 mg (33% yield) of the title compound (25) as a white powder after work-up and mass-guided preparative HPLC purification. $^1$H NMR (CDCl$_3$, 400 MHz): δ=7.85 (br d, 1H), 7.39 (m, 1H), 7.20 (m, 2H), 7.01 (m, 1H), 6.61 (br s, 1H), 6.08 (t, 1H), 4.40 (m, 1H), 4.02 (m, 1H), 3.94 (m, 1H), 2.58 (s, 3H), 1.58 (2d, 3H). MS (ESI) m/z 312.01 (M+H)$^+$; 329.08 (M+NH$_4$)$^+$; 334.06 (M+Na)$^+$.

Example 26

(2R)-3-Hydroxy-2-{[(3-methylbutanoyloxy)ethoxy]carbonylamino}propanoic Acid (26)

Following the general procedure for the synthesis of acyloxyalkyl carbamates, D-serine (252 mg, 2.4 mmol) and (2,5-dioxoazolidinyloxycarbonyloxy)ethyl 3-methylbutanoate (574 mg, 2.0 mmol) were reacted to provide 326 mg (59% yield) of the title compound (26) as a white powder after work-up and mass-guided preparative HPLC purification. $^1$H NMR (CDCl$_3$, 400 MHz): δ=6.80 (m, 1H), 6.11 (m, 1H), 5.78 (br s, 1H), 4.41 (m, 1H), 4.04 (m, 1H), 3.94 (m, 1H), 2.01-2.24 (m, 3H), 1.48 (2d, 3H), 0.99 (2d, 6H). MS (ESI) m/z 278.04 (M+H)$^+$; 295.09 (M+NH$_4$)$^+$; 300.04 (M+Na)$^+$; 276.10 (M−H)$^-$.

Example 27

(2R)-2-[(Cyclohexylcarbonyloxyethoxy)carbonylamino]-3-hydroxypropanoic Acid (27)

Following the general procedure for the synthesis of acyloxyalkyl carbamates, D-serine (252 mg, 2.4 mmol) and (2,5-dioxoazolidinyloxycarbonyloxy)ethyl cyclohexanecarboxylate (626 mg, 2.0 mmol) were reacted to provide 350 mg (58% yield) of the title compound (27) as a white powder after work-up and mass-guided preparative HPLC purification. $^1$H NMR (CDCl$_3$, 400 MHz): δ=6.79 (m, 1H), 6.05 (t, 1H), 5.45 (br s, 1H), 4.41 (m, 1H), 4.04 (m, 1H), 3.92 (m, 1H), 2.30 (m, 1H), 1.09-1.95 (m, 13H). MS (ESI) m/z 321.13 (M+NH$_4$)$^+$; 326.09 (M+Na)$^+$; 302.06 (M−H)$^-$.

Example 28

(2R)-3-Hydroxy-2-[(phenylcarbonyloxyethoxy)carbonylamino]propanoic Acid (28)

Following the general procedure for the synthesis of acyloxyalkyl carbamates, D-serine (252 mg, 2.4 mmol) and (2,5-dioxoazolidinyloxycarbonyloxy)ethyl benzoate (614 mg, 2.0 mmol) were reacted to provide 410 mg (69% yield) the title compound (28) as a white powder after work-up and mass-guided preparative HPLC purification. $^1$H NMR (CDCl$_3$, 400 MHz): δ=8.00 (m, 2H), 7.55 (m, 1H), 7.40 (m, 2H), 7.01 (m, 1H), 6.59 (br s, 1H), 6.21 (m, 1H), 4.39 (m, 1H), 4.02 (m, 1H), 3.86 (m, 1H), 1.60 (2d, 3H). MS (ESI) m/z 298.10 (M+H)$^+$; 315.11 (M+NH$_4$)$^+$, 320.07 (M+Na)$^+$.

Example 29

(2R)-3-Hydroxy-2-{[(2-methylpropanoyloxy)ethoxy]carbonylamino}propanoic Acid (29)

Following the general procedure for the synthesis of acyloxyalkyl carbamates, D-serine (252 mg, 2.4 mmol) and (2,5-dioxoazolidinyloxycarbonyloxy)ethyl 2-methylpropanoate (546 mg, 2.0 mmol) were reacted to provide 212 mg (40% yield) of the title compound (29) as a white powder after work-up and mass-guided preparative HPLC purification. $^1$H NMR (CDCl$_3$, 400 MHz): δ=6.79 (m, 1H), 6.03 (t, 0.2H), 5.58 (br s, 1H), 4.41 (m, 1H), 4.05 (m, 1H), 3.94 (m, 1H), 2.57 (m, 1H), 1.48 (2d, 3H), 1.19 (2d, 6H). MS (ESI) nm/z 281.11 (M+NH$_4$)$^+$; 286.11 (M+Na)$^+$; 262.12 (M−H)$^-$.

Example 30

(2R)-2-[(Butanoyloxyethoxy)carbonylamino]-3-hydroxypropanoic Acid (30)

Following the general procedure for the synthesis of acyloxyalkyl carbamates, D-serine (252 mg, 2.4 mmol) and (2,5-dioxoazolidinyloxycarbonyloxy)ethyl butanoate (546 mg, 2.0 mmol) were reacted to provide 255 mg (40% yield) the title compound (30) as a white powder after work-up and mass-guided preparative HPLC purification. $^1$H NMR (CDCl$_3$, 400 MHz): δ=6.80 (m, 1H), 6.09 (t, 1H), 5.81 (br s, 1H), 4.41 (m, 1H), 4.07 (m, 1H), 3.92 (m, 1H), 2.31 (m, 2H), 1.65 (m, 2H), 1.50 (d, 3H), 0.99 (m, 3H). MS (ESI) m/z 286.07 (M+Na)$^+$; 262.06 (M−H)$^-$.

Example 31

(2R)-3-Hydroxy-2-[(pentanoyloxyethoxy)carbonylamino]propanoic Acid (31)

Following the general procedure for the synthesis of acyloxyalkyl carbamates, D-serine (504 mg, 4.8 mmol) and (2,5-dioxoazolidinyloxycarbonyloxy)ethyl pentanoate (1.1 g, 4.0 mmol) were reacted to provide 809 mg (73% yield) of the title compound (31) as a white powder after work-up and mass-guided preparative HPLC purification. $^1$H NMR (CDCl$_3$, 400 MHz): δ=6.80 (m, 1H), 6.26 (br s, 1H), 5.50 (br s, 1H), 4.40 (m, 1H), 4.02 (m, 1H), 3.85 (m, 1H), 2.36 (m, 2H), 1.60 (m, 2H), 1.47 (d, 3H), 1.37 (m, 2H), 0.91 (t, 3H). MS (ESI) m/z 295.19 (M+NH$_4$)$^+$; 300.08 (M+Na)$^+$; 272.12 (M−H)$^-$.

Example 32

(2R)-3-Hydroxy-2-{[(2-methylpropanoyloxy)methoxy]carbonylamino}propanoic Acid (32)

Following the general procedure for the synthesis of acyloxyalkyl carbamates, D-serine (161 mg, 1.5 mmol) and (2,5-dioxoazolidinyloxycarbonyloxy)methyl 2-methylpropanoate (330 mg, 1.3 mmol) were reacted to provide 110 mg (35% yield) of the title compound (32) as a white powder after work-up and mass-guided preparative HPLC purification. $^1$H NMR (CDCl$_3$, 400 MHz): δ=6.61 (br s, 1H), 6.51 (d, 1H), 5.65 (m, 2H), 4.41 (m, 1H), 4.02 (m, 1H), 3.84 (m, 1H), 2.59 (m, 1H), 1.09 (d, 6H). MS (ESI) m/z 250.15 (M+H)$^+$; 267.17 (M+NH$_4$)$^+$; 272.13 (M+Na)$^+$; 248.12 (M−H)$^-$.

Example 33

(2R)-3-Hydroxy-2-{[2-methyl-1-(2-ethylpropanoyloxy)propoxy]carbonylamino}propanoic Acid (33)

Following the general procedure for the synthesis of acyloxyalkyl carbamates, D-serine (252 mg, 2.4 mmol) and 1-(2,5-dioxoazolidinyloxycarbonyloxy)-2-methylpropyl 2-methylpropanoate (600 mg, 2.0 mmol) were reacted to provide 0.290 mg (50% yield) of the title compound (33) as a white powder after work-up and mass-guided preparative HPLC purification. $^1$H NMR (CDCl$_3$, 400 MHz): δ=6.58 (2d, 1H), 6.45 (br s, 1H), 6.50 (2d, 1H), 4.41 (m, 1H), 4.04 (m, 1H), 3.90 (m, 1H), 2.59 (m, 1H), 2.02 (m, 1H), 1.19 (m, 6H), 0.99 (d, 6H). MS (ESI) m/z 309.24 (M+NH$_4$)$^+$; 314.22 (M+Na)$^+$; 290.21 (M−H)$^-$.

Example 34

2-[(1-Cyclohexylcarbonyloxy-2-methylpropoxy)carbonylamino]-3-hydroxypropanoic Acid (34)

Following the general procedure for the synthesis of acyloxyalkyl carbamates, D-serine (0.40 g, 3.80 mmol) and 1-(2,5-dioxoazolidinyloxycarbonyloxy)-2-methylpropyl cyclohexanecarboxylate (1.0 g, 2.93 mmol) were reacted in the acetonitrile/water mixture to provide 0.091 g (10% yield) of the title compound (34) as a white wax after work-up and mass-guided preparative HPLC purification. $^1$H NMR (CDCl$_3$, 400 MHz): δ=6.58 (dd, 1H), 6.11 (dd, 1H), 4.42-4.31 (m, 1H), 4.11-3.92 (br dd, 2H), 2.38 (m, 1H), 2.11 (m, 1H), 1.97 (br d, 2H), 1.77 (br d, 2H), 1.6 (br d, 1H), 1.4 (q, 2H), 1.2 (br m, 3H), 0.99 (dd, 6H). MS (ESI) m/z 354.22 (M+Na)$^+$; 330.21 (M−H).

Example 35

3-Hydroxy-2-[(2-methyl-1-phenylcarbonyloxypropoxy)carbonylamino] (35)

Following the general procedure for the synthesis of acyloxyalkyl carbamates, D-serine (0.40 g, 3.8 mmol) and 1-(2,5-dioxoazolidinyloxycarbonyloxy)-2-methylpropyl benzoate (1 g, 2.98 mmol) were reacted in the acetonitrile/water mixture to provide 0.121 g (13% yield) of the title compound (35) as a colorless, waxy material after work-up and mass-guided preparative HPLC purification. $^1$H NMR (CDCl$_3$, 400 MHz): δ=8.01 (d, 2H), 7.4 (q, 1H), 7.43 (m, 2H), 6.8 (dd, 1H), 5.99 (dd, 1H), 4.40 (m, 1H), 4.2-3.8 (m, 2H), 2.18 (m, 1H), 1.01 (m, 6H). MS (ESI) m/z 348.15 (M+Na)$^+$; 324.15 (M–H)$^-$.

Example 36

(2R)-2-[(Heptanoyloxyethoxy)carbonylamino]-3-hydroxypropanoic Acid (36)

Following the general procedure for the synthesis of acyloxyalkyl carbamates, D-serine (0.509 g, 4.8 mmol) and (2,5-dioxoazolidinyloxycarbonyloxy)ethyl heptanoate (1 g, 4.03 mmol) were reacted to provide 0.683 g (70% yield) of the title compound (36) as a colorless liquid after work-up and mass-guided preparative HPLC purification. $^1$H NMR (CDCl$_3$, 400 MHz): δ=6.81 (q, 1H), 5.9 (t, 1H), 4.4 (br s, 1H), 4.14-3.98 (m, 2H), 2.36 (t, 2H), 1.63 (t, 2H), 1.5 (d, 3H), 1.3 (m, 6H), 0.85 (t, 3H). MS (ESI) m/z 327.97 (M+Na)$^+$; 304.00 (M–H)$^-$.

Example 37

2-{N-Methyl[2-methyl-1-(2-methylpropanoyloxy)propoxy]carbonylamino}acetic Acid (37)

Following the general procedure for the synthesis of acyloxyalkyl carbamates, sarcosine (0.108 g, 1.19 mmol) and 1-(2,5-dioxoazolidinyloxycarbonyloxy)-2-methylpropyl 2-methylpropanoate (0.3 g, 0.99 mmol) were reacted to provide 0.152 g (55% yield) of the title compound (37) as a colorless liquid after work-up and mass-guided preparative HPLC purification. $^1$H NMR (CD$_3$OD, 400 MHz): δ=6.57 (dd, 1H), 4.19 (m, 2H), 3.03 (2s, 3H), 2.6 (m, 1H), 2.01 (br m, 1H), 1.18 (m, 6H), 1.0-0.98 (2m, 6H). MS (ESI) m/z 298.14 (M+Na)$^+$, 274.13 (M–H)$^-$.

Example 38

2-{N-Methyl[(2-methylpropanoyloxy)ethoxy]carbonylamino}acetic Acid (38)

Following the general procedure for the synthesis of acyloxyalkyl carbamates, sarcosine (0.23 g, 2.63 mmol) and (2,5-dioxoazolidinyloxycarbonyloxy)ethyl 2-methylpropanoate (0.6 g, 2.1 mmol) were reacted to provide 0.459 g (85% yield) of the title compound (38) as a colorless liquid after work-up and mass-guided preparative HPLC purification. $^1$H NMR (CD$_3$OD, 400 MHz): δ=6.88 (q, 1H), 4.12 (m, 2H), 2.9 (2s, 3H), 2.59 (m, 1H), 1.5-1.4 (2d, 3H), 1.1 (m, 6H). MS (ESI) m/z 270.06 (M+Na)$^+$; 246.12 (M–H)$^-$.

Example 39

2-{N-Methyl[(2-methylphenylcarbonyloxy)ethoxy]carbonylamino}acetic Acid (39)

Following the general procedure for the synthesis of acyloxyalkyl carbamates, sarcosine (0.2 g, 2.24 mmol) and (2,5-dioxoazolidinyloxycarbonyloxy)ethyl 2-methylbenzoate (0.6 g, 1.86 mmol) were reacted to provide 0.293 g (53.1% yield) of the title compound (39) as a white wax after work-up and mass-guided preparative HPLC purification. $^1$H NMR (CD$_3$OD, 400 MHz): δ=7.81 (d, 1H), 7.40 (t, 1H), 7.22 (d, 2H), 7.01 (q, 1H), 4.1 (m, 2H), 3.0 (2s, 3H), 2.58 (s, 3H), 1.61-1.59 (2d, 3H). MS (ESI) m/z 318.07 (M+Na)$^+$, 294.10 (M–H)$^-$.

Example 40

2-[N-Methyl(phenylcarbonyloxyethoxy)carbonylamino]acetic Acid (40)

Following the general procedure for the synthesis of acyloxyalkyl carbamates, sarcosine (0.104 g, 1.17 mmol) and (2,5-dioxoazolidinyloxycarbonyloxy)ethyl benzoate (0.3 g, 0.976 mmol) were reacted to provide 122 mg (44% yield) of the title compound (40) as a colorless semi-solid after work-up and mass-guided preparative HPLC purification. $^1$H NMR (CD$_3$OD, 400 MHz): δ=8.01 (d, 2H), 7.61 (t, 1H), 7.44 (t, 2H), 7.01 (q, 1H), 4.12 (m, 2H), 3.01 (2s, 3H), 1.62-1.58 (dd, 3H). MS (ESI) m/z 304.05 (M+Na)$^+$; 280.11 (M–H)$^-$.

Example 41

2-{[(2,2-Dimethylpropanoyloxy)ethoxy]-N-methylcarbonylamino}acetic Acid (41)

Following the general procedure for the synthesis of acyloxyalkyl carbamates, sarcosine (0.104 g, 1.17 mmol) and (2,5-dioxoazolidinyloxycarbonyloxy)ethyl 2,2-dimethylpropanoate (0.280 g, 0.975 mmol) were reacted to provide 0.224 g (88% yield) of the title compound (41) as a colorless semi-solid after work-up and mass-guided preparative HPLC purification. $^1$H NMR (CD$_3$OD, 400 MHz): δ=6.72 (q, 1H), 4.08 (m, 2H), 3.02 (2s, 3H), 1.52-1.40 (dd, 3H), 1.19 (s, 9H). MS (ESI) m/z 284.08 (M+Na)$^+$; 260.11 (M–H)$^-$.

Example 42

2-[(Cyclohexylcarbonyloxyethoxy)-N-methylcarbonylamino]acetic Acid (42)

Following the general procedure for the synthesis of acyloxyalkyl carbamates, sarcosine (0.104 g, 1.1 mmol) and (2,5-dioxoazolidinyloxycarbonyloxy)ethyl cyclohexanecarboxylate (0.292 g, 0.93 mmol) were reacted to provide 0.213 g (79.7% yield) of the title compound (42) as a white waxy solid after work-up and mass-guided preparative HPLC purification. $^1$H NMR (CD$_3$OD, 400 MHz): δ=6.75 (q, 1H), 4.1 (m, 2H), 3.01 (2s, 3H), 2.3 (m, 1H), 1.90 (br m, 2H)), 1.75 (m, 2H), 1.65, (m, 1H), 1.5-1.39 (2d, 5H), 1.4 (m, 3H). MS (ESI) m/z 310.19 (M+Na)$^+$, 289 (M–H)$^-$.

Example 43

2-[N-Methyl(pentanoyloxyethoxy)carbonylamino] acetic Acid (43)

Following the general procedure for the synthesis of acyloxyalkyl carbamates, sarcosine (0.104 g, 1.1 mmol) and (2,5-dioxoazolidinyloxycarbonyloxy)ethyl pentanoate (0.268 g, 0.93 mmol) were reacted to provide 0.130 g (53.3% yield) of the title compound (43) as a white powder after work-up and mass-guided preparative HPLC purification. $^1$H NMR (CD$_3$OD, 400 MHz): δ=6.79 (q, 1H), 4.12 (m, 2H), 3.0 (2s, 2H), 2.36 (m, 2H), 1.62 (q, 2H), 1.56 (2d, 3H), 1.39 (q, 2H), 0.97 (t, 3H). MS (ESI) m/z 284.09 (M+Na)$^+$; 260.05 (M–H)$^-$.

Example 44

2-[(Butanoyloxyethoxy)-N-methylcarbonylamino] acetic Acid (44)

Following the general procedure for the synthesis of acyloxyalkyl carbamates, sarcosine (0.117 g, 1.3 mmol) and (2,5-dioxoazolidinyloxycarbonyloxy)ethyl butanoate (0.303 g, 1.09 mmol) were reacted to provide 0.147 g (53.6% yield) the title compound (44) as a colorless, sticky material after work-up and mass-guided preparative HPLC purification. $^1$H NMR (CD$_3$OD, 400 MHz): δ=6.78 (q, 1H), 4.12 (m, 2H), 3.01 (2s, 3H), 2.33 (m, 2H), 1.62 (q, 2H), 1.51 (2d, 3H), 0.98 (t, 3H). MS (ESI) m/z 270.08 (M+Na)$^+$; 246.09 (M−H)$^−$.

Example 45

2-{N-Methyl[(3-methylbutanoyloxy)ethoxy] carbonylamino}acetic Acid (45)

Following the general procedure for the synthesis of acyloxyalkyl carbamates, sarcosine (0.104 g, 1.1 mmol) and (2,5-dioxoazolidinyloxycarbonyloxy)ethyl 3-methylbutanoate (0.28 g, 0.97 mmol) were reacted to provide 0.070 g (27.5% yield) of the title compound (45) as a colorless, waxy material after work-up and mass-guided preparative HPLC purification. $^1$H NMR (CD$_3$OD, 400 MHz): δ=6.78 (q, 1H), 4.12 (m, 2H), 2.99 (2s, 3H), 2.23 (m, 2H), 2.12 (m, 1H), 1.52 (2d, 3H), 0.99 (t, 3H). MS (ESI) m/z 284.08 (M+Na)$^+$, 260.13 (M−H)$^−$.

Example 46

2-{N-Methyl[(2-methylpropanoyloxy)methoxy] carbonylamino}acetic Acid (46)

Following the general procedure for the synthesis of acyloxyalkyl carbamates, sarcosine (0.123 g, 1.3 mmol) and (2,5-dioxoazolidinyloxycarbonyloxy)methyl 2-methylpropanoate (0.300 g, 1.1 mmol) were reacted to provide 0.138 g (5.1.3% yield) of the title compound (46) as a colorless semisolid material after work-up and mass-guided preparative HPLC purification. $^1$H NMR (CD$_3$OD, 400 MHz): δ=5.78 (d, 2H), 4.12 (d, 3H), 3.02 (d, 3H), 2.62 (m, 1H), 1.2 (t, 6H). MS (ESI) m/z 256.05 (M+Na)$^+$.

Example 47

2-[(1-Cyclohexylcarbonyloxy-2-methylpropoxy)-N-methylcarbonylamino]acetic Acid (47)

Following the general procedure for the synthesis of acyloxycarbamates, sarcosine (0.31 g, 3.50 mmol) and 1-(2,5-dioxoazolidinyloxycarbonyloxy)-2-methylpropyl cyclohexanecarboxylate (1.0 g, 2.92 mmol) were reacted in an acetonitrile/water mixture (20 mL) to provide 0.146 g (16% yield) of the title compound (47) as a white, waxy material after work-up and mass-guided preparative HPLC purification. $^1$H NMR (CDCl$_3$, 400 MHz): δ=6.60 (t, 1H), 4.20-3.82 (m, 2H), 3.01 (d, 3H), 2.39 (m, 1H), 2.15 (m, 1H), 1.98 (br d, 2H), 1.80 (br d, 2H), 1.71 (br s, 1H), 1.53 (m, 2H), 1.32 (m, 3H), 1.01 (2d, 6H). MS (ESI) 1 m/z 337.99 (M+Na)$^+$; 314.02 (M−H)$^−$.

Example 48

2-[N-Methyl(2-methyl-1-phenylcarbonyloxypropoxy)carbonylamino]acetic Acid (48)

Following the general procedure for the synthesis of acyloxyalkylcarbamates, sarcosine (0.345 g, 3.8 mmols) and 1-(2,5-dioxoazolidinyloxycarbonyloxy)-2-methylpropyl benzoate (1 g, 2.98 mmol) were reacted in an acetonitrile/water mixture (20 mL) to provide 0.364 g (39.5% yield) of the title compound (48) as a colorless, waxy material after work-up and mass-guided preparative HPLC purification. $^1$H NMR (CDCl$_3$, 400 MHz): δ=8.05 (t, 2H), 7.59 (t, 1H), 7.43 (t, 2H), 6.84 (m, 1H), 4.21-3.88 (br m, 2H), 3.0 (d, 3H), 2.25 (m, 1H), 1.15 (dd, 6H). MS (ESI) m/z 332.20 (M+Na)$^+$; 308.21 (M−H)$^−$.

Example 49

2-[(Heptanoyloxyethoxy)-N-methylcarbonylamino] acetic Acid (49)

Following the general procedure for the synthesis of acyloxyalkyl carbamates, sarcosine (0.430 g, 4.8 mmol) and (2,5-dioxoazolidinyloxycarbonyloxy)ethyl heptanoate (1 g, 4.02 mmol) were reacted together to provide 0.135 g (14.7% yield) of the title compound (49) as a colorless liquid after work-up and mass-guided preparative HPLC purification. $^1$H NMR (CDCl$_3$, 400 MHz): δ=6.80 (q, 1H), 4.21-3.88 (m, 1H), 3.98 (m, 1H), 3.01 (s, 3H), 2.31 (m, 2H), 1.64 (m, 2H), 1.5 (2d, 3H), 1.32 (m, 6H), 0.98 (t, 3H). MS (ESI) m/z 312.13 (M+Na)$^+$; 288.15 (M−H)$^−$.

Example 50

2-[N-Methyl(phenylphenylcarbonyloxymethoxy) carbonylamino]acetic Acid (50)

Step A: Chlorophenylchloroformate

A solution of benzaldehyde (5 g, 47.1 mmol), and pyridine (0.53 mL, 4.71 mmol) in CCl$_4$ was stirred under a nitrogen atmosphere at −20° C. Trichloromethyl carbonate (6.90 g, 23.5 mmol) was added in portions for 5 min such that the reaction temperature was maintained at −20° C. The resulting viscous solution was warmed at ca. room temperature over 90 min followed by heating to 40° C. for one hour. The reaction mixture was cooled and stirred overnight at ca. room temperature. Filtration of pyridinum salts followed by removal of solvent in vacuo gave crude chlorophenylchloroformate, which was used without further purification.

Step B: 2-[N-methyl(phenylphenylcarbonyloxymethoxy)carbonylamino]acetic Acid

Following the general procedure for the one pot synthesis, sarcosine (1.0 g, 11.2 mmol) was reacted with chlorotrimethylsilane (2.8 mL, 22.4 mmol) in anhydrous chloroform (25 mL) in the presence of DIEA (4.1 mL, 22.4 mmol). Subsequent reaction of the intermediate with 1-chloro-2-methylpropyl chloroformate (4.59 g, 22.4 mmol) followed by a mixture of DIEA (4.1 mL, 22.4 mmol) and benzoic acid (2.8 g, 22.4 mmol) provided 0.622 g (16.3% yield) of the title compound (50) as a buff-colored solid after aqueous work-up and mass-guided preparative HPLC purification. $^1$H NMR (CD$_3$OD, 400 MHz): δ=8.13 (d, 2H), 7.81 (d, 1H), 7.61 (m, 3H), 7.57 (m, 5H), 4.10 (br m, 2H), 3.01 (2s, 3H). MS (ESI) m/z 366.14 (M+Na)$^+$.

Example 51

Methods for Determination of Enzymatic Cleavage of Prodrugs In Vitro

For a prodrug, it may be desirable that the prodrug remains intact (i.e., uncleaved) while in the systemic circulation and be cleaved (i.e., to release the parent drug) in the target tissue. Alternatively, it may be desirable that the prodrug remains intact (i.e., uncleaved) while in the gastrointestinal tract and be cleaved (i.e., to release the parent drug) after being absorbed or taken up from the gastrointestinal lumen, e.g., in either the enterocytes lining the gastrointestinal lumen or in the blood. A useful level of stability may at least in part be determined by the mechanism and pharmacokinetics of the prodrug. A useful level of liability may at least in part also be determined by the pharmacokinetics of the prodrug and parent drug in the systemic circulation and/or in the gastrointestinal tract, if orally administered. In general, prodrugs that are more stable in pancreatin or colonic wash assay and are more labile in a rat plasma, human plasma, rat liver S9, and/or human liver S9 preparations may be useful as an orally administered prodrug. In general, prodrugs that are more stable in rat plasma, human plasma, rat liver S9, and/or human liver S9 preparations and which are more labile in cell homogenate preparations, such Caco-2 S9 preparations, may be useful as systemically administered prodrugs and/or may be more effective in delivering a prodrug to a target tissue. In general, prodrugs that are more stable in different pH physiological buffers (e.g., ranging from about pH 6.0 to pH 8.5) may be more useful as prodrugs. In general, prodrugs that are more labile in cell homogenate preparations, such Caco-2 S9 preparations, may be intracellularly cleaved to release the parent drug to a target tissue. The results of tests, such as those described in this example, for determining the enzymatic or chemical cleavage of prodrugs in vitro may be used to select prodrugs for in vivo testing.

The stabilities of prodrugs may be evaluated in one or more in vitro systems using a variety of preparations following methods known in the art. Tissues and preparations are obtained from commercial sources (e.g., Pel-Freez Biologicals, Rogers, Ark., or GenTest Corporation, Woburn, Mass.). Experimental conditions useful for the in vitro studies are described in Table 1. The prodrug is added to each preparation in triplicate.

For preparations that contain alkaline phosphatases, the prodrug is tested in the presence and absence of a phosphatase inhibitor cocktail (Sigma). Samples are incubated at 37° C. for times ranging from 30 minutes to 24 hours. At each time point, samples are quenched with 50% ethanol. Baseline concentrations of the prodrug are determined by adding the compound directly to the 50% ethanol/preparation mixture (t=0). Samples are centrifuged at 14,000 rpm for 15 minutes, and concentrations of intact prodrug and released parent drug are determined using LC/MS/MS. This stability of prodrugs towards specific enzymes (e.g., peptidases, etc.) is also assessed in vitro by incubation with the purified enzyme.

Pancreatin stability studies are conducted by incubating the prodrug (5 µM) with 1% (w/v) pancreatin (Sigma, P-1625, from porcine pancreas) in 0.025 M Tris buffer containing 0.5 M NaCl (pH 7.5) at 37° C. The reaction is stopped by addition of 3 volumes of 50% ethanol. After centrifugation at 14,000 rpm for 15 min, the supernatant is removed and analyzed by LC/MS/MS.

To determine stability in Caco-2 homogenate S9, Caco-2 cells are grown for 21 days prior to harvesting. Culture medium is removed and cell monolayers are rinsed and scraped off into ice cold 10 mM sodium phosphate/0.15 M potassium chloride, pH 7.4. Cells are lysed by sonication at 4° C. using a probe sonicator. Lysed cells are then transferred into 1.5 mL centrifuge vials and centrifuged at 9,000 g for 20 min at 4° C. The resulting supernatant (Caco-2 cell homogenate S9 fraction) is aliquoted into 0.5 mL vials and stored at −80° C. until used.

For stability studies, prodrug (5 µM) is incubated in Caco-2 homogenate S9 fraction (0.5 mg/mL in 0.1M Tris buffer, pH 7.4) at 37° C. Triplicate samples are quenched at each time point with 50% ethanol. The initial (t=0) concentration of prodrug is determined by adding 5 µM prodrug directly to a 50% ethanol/Caco-2 homogenate mixture. Samples are subjected to LC/MS/MS analysis to determine concentrations of the prodrug and the parent drug.

To determine prodrug stability in rat plasma, the prodrug (5 µM) is incubated in undiluted rat plasma. Triplicate samples are quenched at each time point with 50% ethanol. The initial (t=0) concentration of prodrug is determined by adding 5 µM prodrug directly to a 50% ethanol/rat plasma mixture. Samples are subjected to LC/MS/MS analysis to determine concentrations of prodrug and parent drug.

For rat S9 stability studies, prodrug (5 µM) is incubated in rat liver S9 homogenate (0.5 mg/mL in 0.1 M potassium phosphate buffer, pH 7.4, 1 mM NADPH) at 37° C. Triplicate samples are quenched at each time point with 50% ethanol. The initial (t=0) concentration of prodrug is determined by adding 5 µM prodrug directly to a 50% ethanol/S9 homogenate mixture. Samples are subjected to LC/MS/MS analysis to determine concentrations of prodrug and parent drug.

Three buffers are used to determine the chemical stability of prodrug: (1) 0.1M potassium phosphate, 0.5 M NaCl, pH 2.0, (2) 0.1M Tris-HCl, 0.5M NaCl, pH 7.4, and (3) 0.1 M Tris-HCl, 0.5 M NaCl, pH 8.0. The prodrug (5 µM) is added to each buffer in triplicate. Samples are quenched at each time point with 50% ethanol. The initial (t=0) concentration of prodrug is determined by adding 5 µM prodrug directly to a 50% ethanol/pH Buffer mixture. Samples are subjected to LC/MS/MS analysis to determine concentrations of prodrug and parent drug.

TABLE 1

Standard Conditions for Prodrug In Vitro Metabolism Studies

| Preparation | Prodrug Concentration | Cofactors |
| --- | --- | --- |
| Rat Plasma | 2.0 µM | None |
| Human Plasma | 2.0 µM | None |
| Rat Liver S9 (0.5 mg/mL) | 2.0 µM | NADPH* |
| Human Liver S9 (0.5 mg/mL) | 2.0 µM | NADPH* |
| Human Intestine S9 (0.5 mg/mL) | 2.0 µM | NADPH* |
| Caco-2 Homogenate | 5.0 µM | None |
| Pancreatin | 5.0 µM | None |

*NADPH generating system, e.g., 1.3 mM NADP$^+$, 3.3 mM glucose-6-phosphate, 0.4 U/mL glucose-6-phosphate dehydrogenase, 3.3 mM magnesium chloride, and 0.95 mg/mL potassium phosphate, pH 7.4.

Example 52

In Vitro Determination of Caco-2 Cellular Permeability of Prodrugs

The passive permeability of a prodrug provided by the present disclosure may be assessed in vitro using standard methods well known in the art (see, e.g., Stewart, et al., Pharm. Res., 1995, 12, 693). For example, passive permeability may be evaluated by examining the flux of a prodrug across a cultured polarized cell monolayer (e.g., Caco-2 cells). Caco-2 cells obtained from continuous culture (passage less than 28) are seeded at high density onto Transwell polycarbonate filters. Cells are maintained with DMEM/10% fetal calf serum+0.1 mM nonessential amino acids+2 mM L-Gln, 5% $CO_2$/95% $O_2$, 37° C. until the day of the experiment. Permeability studies are conducted at pH 6.5 apically (in 50 mM MES buffer containing 1 mM $CaCl_2$, 1 mM $MgCl_2$, 150 mM NaCl, 3 mM KCl, 1 mM $NaH_2PO_4$, 5 mM glucose) and pH 7.4 basolaterally (in Hanks' balanced salt solution containing 10 mM HEPES) in the presence of efflux pump inhibitors (250 µM MK-571, 250 µM verapamil, 1 mM ofloxacin). Inserts are placed in 12 or 24 well plates containing buffer and incubated for 30 min at 37° C. The prodrug (200 µM) is added to the apical or basolateral compartment (donor) and concentrations of the prodrug and/or released parent drug in the opposite compartment (receiver) are determined at intervals over 1 hour using LC/MS/MS. Values of apparent permeability ($P_{app}$) are calculated using the equation:

$$P_{app}=V_r(dC/dt)/(AC_o)$$

where $V_r$ is the volume of the receiver compartment in mL; dC/dt is the total flux of prodrug and parent drug (µM/s), determined from the slope of the plot of concentration in the receiver compartment versus time; $C_o$ is the initial concentration of prodrug in µM; and A is the surface area of the membrane in $cm^2$. Prodrugs with significant transcellular permeability generally demonstrate a value of $P_{app}$ of $\geq 1 \times 10^{-6}$ cm/s, for example, a value of $P_{app}$ of $\geq 1 \times 10^{-5}$ cm/s, and a value of $P_{app}$ of $\geq 5 \times 10^{-5}$ cm/s.

Example 53

Bioavailability of α-Amino Acid Prodrugs and Metabolites Thereof Following Intracolonic Administration in Rats and Monkeys Rats are obtained commercially and were pre-cannulated in the both the ascending colon and the jugular vein. Animals were conscious at the time of the experiment. All animals were fasted overnight and until 4 hours after dosing of an α-amino acid prodrug. An α-amino acid or the corresponding prodrug was administered as a solution (in water) directly into the colon via the cannula at a dose equivalent to about 75 mg or other appropriate dose of an α-amino acid per kg body weight. Blood samples (0.3 mL) were obtained from the jugular cannula at intervals over 8 hours and were quenched immediately by addition of sodium metabisulfite to prevent oxidation of the α-amino acid. Blood was then further quenched with methanol/perchloric acid to prevent hydrolysis of the prodrug. Blood samples were analyzed as described.

For studies using monkeys, test compounds were administered by intracolonic bolus injection to groups of four adult male Cynomologous (Macaca fascicularis) monkeys (weight approx 3 kg) as solutions in water or sodium phosphate buffer, pH 7.4, at a dose of 20 mg-equivalents of 1-aminocyclopropanecarboxylic acid per kg body weight. Animals were fasted overnight before the study and for 4 hours post-dosing. Blood samples (1.0 mL) were obtained via the femoral vein at intervals over 24 hours after oral dosing. Blood was quenched immediately using methanol and then frozen at −80° C. until analyzed. Test compounds were administered in the monkeys with a minimum of 7-day wash out period between dosing sessions.

300 µL of methanol was added to 1.5 mL tubes. Rat or monkey blood (100 µL) was collected at different times into the tubes and vortexed to mix. 90 µL of blood was quenched with 300 µL methanol. 10 µL of a standard stock solution containing an α-amino acid (0.04, 0.2, 1, 5, 25, and 100 µg/mL) and 20 µL of p-chlorophenylalanine eas added to 90 µL of blood to make up a final calibration standard (0.004, 0.02, 0.1, 0.5, 2.5, and 10 µg/mL). Samples were vortexed and centrifuged at 3400 rpm for 20 min. The supernatant was analyzed by LC/MS/MS.

An API 4000 LC/MS/MS spectrometer equipped with Agilent 1100 binary pumps and a CTC HTS-PAL autosampler and an Agilent Zorbax Eclipse XBD-C8, 4.6×150 mm, 3.5 µM column was used for the analysis. The mobile phase was 0.02% heptafluorobutyric acid in water (A) and 0.02% heptafluorobutyric acid in acetonitrile (B). The flow rate was 1.0 mL/min. The gradient condition was: 5% B for 2 min, then to 10% B for 1 min. Then the mobile phase was returned to 5% B for 1.1 min. A TurboIonSpray source was used in the API 4000. The analysis was done in either negative ion mode or positive ion mode as appropriate and the MRM transition for each analyte was optimized using a standard solution. 20 µL of the samples were injected. Non-compartmental analysis was performed using WinNonlin software (v.3.1 Professional Version, Pharsight Corporation, Mountain View, Calif.) on individual animal profiles. Summary statistics on major parameter estimates was performed for $C_{max}$ (peak observed concentration following dosing), $T_{max}$ (time to maximum concentration is the time at which the peak concentration was observed), $AUC_{(0-t)}$ (area under the plasma concentration-time curve from time zero to last collection time, estimated using the log-linear trapezoidal method), $AUC_{(0-\infty)}$, (area under the plasma concentration time curve from time zero to infinity, estimated using the log-linear trapezoidal method to the last collection time with extrapolation to infinity), and $t_{1/2,z}$ (terminal half-life).

Prodrugs that provide a bioavailability of the corresponding α-amino acid that is greater than the bioavailability provided by an equimolar dose of the α-amino acid administered to a patient by the same route (e.g., oral administration) may be useful as therapeutic agents, and more particularly, as sustained release therapeutic agents.

The oral or intracolonic bioavailability (F) of an α-amino acid was determined by comparing the area under the α-amino acid concentration vs. time curve (AUC) following oral or intracolonic administration of α-amino acid or prodrug thereof with the AUC of the α-amino acid concentration vs. time curve following intravenous administration of the α-amino acid on a dose normalized basis (e.g., % $F_{ic}$=AUC (following intracolonic administration of an α-amino acid prodrug)/AUC (following intravenous administration of an equivalent dose of the corresponding α-amino acid)). An $AUC_{inf}$ of 85.9 µg·hr/mL for the intravenously administered α-amino acid, 1-aminocyclopropanecarboxylic acid (dosed at 20 mg-eq/kg) was used for the calculations of the bioavailability of 1-aminocyclopropanecarboxylic acid released from the corresponding prodrugs post absorption in rats. Compounds 2, 3, 4, 11, 12, 16, 18, and 23 showed substantial colonic bioavailability of 1-aminocyclopropanecarboxylic acid in rats. In monkeys, following, colonic administration of α-amino acid prodrug 2, the bioavailability of 1-aminocyclopropanecarboxylic acid was determined to be about 4-fold greater than after colonic administration of 1-aminocyclopropanecarboxylic acid itself (at 20 mg-eq/kg).

Example 54

PCP-Induced Hyperactivity Animal Model of Schizophrenia

Male C57Bl/6J mice from Jackson Laboratories (Bar Harbor, Me.) are used. Mice are received at 6-weeks of age. Upon receipt, mice are assigned unique identification numbers (tail marked) and are group housed with 4 mice/cage in OPTI mouse ventilated cages. All animals remain housed in groups of four during the study. All mice are acclimated to the colony room for at least two weeks prior to testing and are subsequently tested at an average age of 8 weeks of age. During the period of acclimation, mice and rats are examined on a regular basis, handled, and weighed to assure adequate health and suitability. Animals are maintained on a 12/12 light/dark cycle. The room temperature is maintained between 20° C. and 23° C. with a relative humidity maintained between 30% and 70%. Chow and water are provided ad libitum for the duration of the study. In each test, animals are randomly assigned across treatment groups. All animals are euthanized at the end of the study.

Test compounds are prepared and administered according to the following procedures. An α-amino acid prodrug is dissolved in sterile injectable water and administered i.p. at a dose volume of 10 mL/kg at 60 min prior to PCP injection. The amount of α-amino acid prodrug administered can range, for example, from 0.01 mg/kg to 100 mg/kg. As a positive control, clozapine (1 mg/kg) is dissolved in 10% DMSO and administered i.p. at a dose volume of 10 mL/kg at 30 min prior to PCP injection. PCP (5 mg/kg) is dissolved in sterile injectable water and administered i.p. at a dose volume of 10 mL/kg.

The Open Field (OF) test is used to assess both anxiety and locomotor behavior. The open field chambers are Plexiglas square chambers (27.3×27.3×20.3 cm; Med Associates Inc., St Albans, Vt.) surrounded by infrared photobeams (16×16×16) to measure horizontal and vertical activity. The analysis is configured to divide the open field into a center and periphery zone. Distance traveled is measured from horizontal beam breaks as a mouse moves, and rearing activity is measured from vertical beam breaks.

Mice are acclimated to the activity experimental room for at least 1 hr to prior to testing. Eight animals are tested in each run. Mice are injected with water or α-amino acid prodrug, placed in holding cages for 30 min, and then in the OF chamber for 30 min, removed from the OF chamber and injected with either water or PCP and returned to the OF chambers for a 60-minute session. A different group of mice are injected with either 10% DMSO or clozapine and placed in the OF chamber for 30 min, removed from the OF chamber and injected with PCP (5 mg/kg), and returned to the OF chambers for a 60-minute session.

Data is analyzed by analysis of variance (ANOVA) followed by post-hoc comparisons with Fisher Tests when appropriate. Baseline activity is measured during the first 30 min of the test prior to PCP injection. PCP-induced activity is measured during the 60 min following PCP injection. Statistical outliers that fall above or below 2 standard deviations from the mean are removed from the final analysis. An effect is considered significant if $p<0.05$.

Example 55

Auditory Startle and Prepulse Inhibition of Startle (PPI) Animal Model of Schizophrenia Young, adult male C57Bl/6J mice from Jackson Laboratories (Bar Harbor, Me.) are used in this study. Mice are received at 6-weeks of age. Upon receipt, mice are assigned unique identification numbers (tail marked) and are group housed in standard mouse cages. All animals remain housed in groups of four during the study. All mice are acclimated to the colony room for at least two weeks prior to testing and are subsequently tested at an average age of 8-9 weeks of age. During the period of acclimation, mice are examined on a regular basis, handled, and weighed to assure adequate health and suitability. Mice are maintained on a 12 h/12 h light/dark cycle with the light on at 7:00 a.m. The room temperature is maintained between 20° C. and 23° C. with a relative humidity maintained between 30% and 70%. Feed and water are provided ad libitum during the study. For testing, animals are randomly assigned across treatment groups and balanced by PPI chamber.

Test compounds are prepared and administered according to the following procedures. An α-amino acid prodrug is dissolved in sterile injectable water and administered i.p. at a dose volume of 10 mL/kg at 60 min prior to testing. The amount of α-amino acid prodrug administered can range, for example, from 0.01 mg/kg to 100 mg/kg. Haloperidol (1 mg/kg) is dissolved in 10% DMSO and administered i.p. 30 minutes prior to testing the normal mouse-PPI portion of the study. As a positive control, clozapine (3 mg/kg) is dissolved in 1% Tween and administered i.p. 60 min prior to testing the PCP-PPI portion of the study. PCP (8 mg/kg) is dissolved in sterile injectable water and administered 30 minutes prior to testing. All compounds are delivered at a dose volume of 10 mL/kg.

Acoustic startle measures an unconditioned reflex response to external auditory stimulation. PPI consisting of an inhibited startle response (reduction in amplitude) to an auditory stimulation following the presentation of a weak auditory stimulus or prepulse, has been used as a tool for the assessment of deficiencies in sensory-motor gating, such as those seen in schizophrenia. Mice are placed in the PPI chamber (Med Associates) for a 5 min session of white noise (70 dB) habituation. A test session begins immediately after the 5 min acclimation period. The session starts with a habituation block of 6 presentations of the startle stimulus alone, followed by 10 PPI blocks of 6 different types of trials. Trial types are: null (no stimuli), startle (120 dB), startle plus prepulse (4, 8 and 12 dB over background noise i.e., 74, 78 or 82 dB) and prepulse alone (82 dB). Trial types are presented at random within each block. Each trial begins with a 50 ms null period during which baseline movements are recorded. There is a subsequent 20 ms period during which prepulse stimuli are presented and responses to the prepulse measured. Following a 100 ms pause, the startle stimuli are presented for 40 ms and responses are recorded for 100 ms from startle onset. Responses are sampled every ms. The inter-trial interval is variable with an average of 15 s (range from 10 to 20 s). In startle alone trials the basic auditory startle is measured and in prepulse plus startle trials the amount of inhibition of the normal startle is determined and expressed as a percentage of the basic startle response (from startle alone trials), excluding the startle response of the first habituation block.

For the normal mouse-PPI portion of the study, C57BL/6J mice are treated with vehicle, haloperidol or α-amino acid and placed back in their holding cages. Thirty min following injection of vehicle or haloperidol and 60 min following injection of vehicle or α-amino acid, normal mouse-PPI testing commenced.

For the PCP-PPI portion of the study, C57BL/6J mice are treated with vehicle, clozapine, or α-amino acid prodrug and returned to their holding cages. Thirty min later, all treatment groups are injected with vehicle or PCP. Thirty min following vehicle or PCP injection, PPI testing commences.

Mice are returned to holding cages and sacrificed immediately following testing.

Data is analyzed by analysis of variance (ANOVA) followed by post-hoc analysis when appropriate. An effect is considered significant if $p<0.05$. For the PPI analysis, all mice that had a startle response below 100 are removed from the analysis.

Example 56

Animal Model for Assessing Therapeutic Efficacy of α-Amino Acid Prodrugs for Treating Anxiety A method for assessing the effects of test compounds on anxiety described by Pellow and File, *Pharmacol Biochem Behav* 1986, 24, 524-529, i.e., the elevated plus-maze test, is used. A plus-maze is consists of two open arms (50×10 cm) and two closed arms (50×10×40 cm). The arms extend from a central platform (10×10 cm) and are raised 50 cm. Each mouse is placed at the center of the maze facing a closed arm and is allowed to explore the maze for 5 min. The time spent in the open arms and the time spent in the closed arms is monitored, and the percent of time spent in the open arms determined. Increased time spent in the open arms indicates an anxiolytic effect for the test condition. A test that measures spontaneous locomotor activity such as measurement in an activity cage can be used to determine whether the test compound also affects locomotor activity. It is desirable that a compound exhibiting an anxiolytic effect not decrease locomotor activity.

Example 57

Animal Models of Depression

Forced Swim Test in Rats

Male Wistar rats weighting 230-270 g are acclimated to the colony room for a minimum of I week, handled daily for at least 4 days and habituated to saline injections for 2 days before the experiments.

Two glass cylinders (20 cm dia×40 cm height) are separated by black opaque partitions and filled with water at about 24° C. to a depth of 30 cm. At this depth a rat cannot stand on the cylinder bottom. The water level is 10 cm from the top. Water is changed before each animal is placed into the water tank. An experimental session consists of two trials. During the conditioning trial, rats are gently placed into the cylinders for 15 min. After the trail, rats are dried and placed into a warm cage with the paper towels for 10-15 min before being returned to their home cages. Twenty-four hours later, for the test trail, animals are placed again into the cylinders for a 5-min test session. Tests are video taped for subsequent quantitative behavioral analysis. The frequency and/or total duration are calculated for each of the following categories: passive/immobile behavior (floating is scored when an animal remains in the water with all four limbs motionless, except for occasional alternate movements of paws and tail necessary to prevent sinking and to keep head/nose above the water); active/mobile behaviors (swimming characterized by rigorous movements with all four legs; paddling characterized by floating with rhythmical simultaneous kicks and occasional pushes off the wall to give speed and direction to the drift), including escape-oriented behaviors (climbing characterized by intense movements with all four limbs, with the two forepaws breaking the surface of the water and being directed against the walls of the cylinder; diving characterized by movements towards the bottom of the cylinder with the head of the rat below its hind limbs), and self-directed behaviors (headshakes, vigorous headshakes to get water off the snout and eyes; wiping, rubbing water away form the snout). In addition, at the end of each test trial, fecal boli are counted. A test compound, control, or positive control (e.g., imipramine) is administered prior to the test.

Tail Suspension Test in Mice

Mice are housed in standard laboratory cages and acclimated. Mice are moved from the housing room to the testing area in their home cages and allowed to adapt to the new environment for at least 1 h before testing. Immobility is induced by tail suspension according to the procedure of Steru et al., *Psychopharmacology* 1985, 85, 367-370. Mice are hung individually on a paper adhesive tape, 65 cm above a tabletop. Tape is placed approximately 1 cm from the tip of the tail. Animals are allowed to hang for 6 min and the duration of immobility is recorded. Mice are considered immobile only when hanging passively and completely motionless. Mice from these experiments are used one week later in locomotor activity studies. A test compound, control, or positive control (e.g., imipramine) is administered prior to the test.

Locomotor Activity

The spontaneous locomotor activity of rats is measured in photoresistor actometers (40×40×25 cm, two light sources, two photoresistors), where the animals are placed after administration of a test compound. The number of crossings of light beams is measured during the first 30 min of an experimental session. The first measurement is performed 5 min after placing an animal in the actometer.

Example 58

Animal Model for Assessing Therapeutic Efficacy of α-Amino Acid Prodrugs for Treating Spasticity The mutant spastic mouse is a homozygous mouse that carries an autosomal recessive trait of genetic spasticity characterized by a deficit of glycine receptors throughout the central nervous system (Chai et al., *Proc. Soc. Exptl. Biol. Med.* 1962, 109, 491). The mouse is normal at birth and subsequently develops a coarse tremor, abnormal gait, skeletal muscle rigidity, and abnormal righting reflexes at two to three weeks of age. Assessment of spasticity in the mutant spastic mouse can be performed using electrophysiological measurements or by measuring the righting reflex (any righting reflex over one second is considered abnormal), tremor (holding mice by their tails and subjectively rating tremor), and flexibility.

Models of acute spasticity including the acute decerebrate rat, the acute or chronic spinally transected rat, and the chronically spinal cord-lesioned rat (see e.g., Wright and Rang, *Clin Orthop Relat Res* 1990, 253, 12-19; Shimizu et al., *J Pharmacol Sci* 2004, 96, 444-449; and Li et al., *J Neurophysiol* 2004, 92, 2694-2703). The acute models, although valuable in elucidating the mechanisms involved in the development of spasticity, have come under criticism due to the fact that they are acute. The animals usually die or have total recovery from spasticity. The spasticity develops immediately upon intervention, unlike the spasticity that evolves in the human condition of spasticity, which most often initially manifests itself as a flaccid paralysis. Only after weeks and months does spasticity develop in humans. Some of the more chronic-lesioned or spinally transected models of spasticity do postoperatively show flaccid paralysis. At approximately four weeks post-lesion/transection, the flaccidity changes to spasticity of variable severity. Although all of these models have their own particular disadvantages and lack of true representation of the human spastic condition, they are shown useful in developing treatments for spasticity in humans. Many of these models have also made use of different species, such as cats, dogs, and primates. Baclofen, diazepam, and tizanidine, effective antispastic agents in humans, are effective on different parameters of electrophysiologic assessment of muscle tone in these models.

The Irwin Test is used to detect physiological, behavioral, and toxic effects of a test substance, and indicates a range of dosages that can be used for later experiments (Irwin, *Psychopharmacologia* 1968, 13, 222-57). Typically, rats (three per group) are administered the test substance and are then observed in comparison with a control group given vehicle. Behavioral modifications, symptoms of neurotoxicity, pupil diameter, and rectal temperature are recorded according to a standardized observation grid derived from that of Irwin. The grid contains the following items: mortality, sedation, excitation, aggressiveness, Straub tail; writhes, convulsions, tremor, exopthalmos, salivation, lacrimation, piloerection, defecation, fear, traction, reactivity to touch, loss of righting reflexes, sleep, motor incoordination, muscle tone, stereotypes, head-weaving, catalepsy, grasping, ptosis, respiration, corneal reflex, analgesia, abnormal gait, forepaw treading, loss of balance, head twitches, rectal temperature, and pupil diameter. Observations are performed at 15, 30, 60, 120, and 180 minutes following administration of a test compound, and also 24 hours later.

In the Rotarod Test (Dunham et al., *J. Am. Pharm. Assoc.* 1957, 46, 208-09) rats or mice are placed on a rod rotating at a speed of eight turns per minute. The number of animals that drop from the rod before three minutes is counted and the drop-off times are recorded (maximum: 180 sec). Diazepam, a benzodiazepine, can be administered at 8 mg/kg, i.p., as a reference substance.

Example 59

Animal Models for Assessing Therapeutic Efficacy of α-Amino Acid Prodrugs for Treating Parkinson's Disease MPTP Induced Neurotoxicity MPTP, or 1-methyl-4-phenyl-1,2,3,6-tetrahydropyridine is a neurotoxin that produces a Parkinsonian syndrome in both man and experimental animals. Studies of the mechanism of MPTP neurotoxicity show that it involves the generation of a major metabolite, $MPP^+$, formed by the activity of monoamine oxidase on MPTP. Inhibitors of monoamine oxidase block the neurotoxicity of MPTP in both mice and primates. The specificity of the neurotoxic effects of $MPP^+$ for dopaminergic neurons appears to be due to the uptake of $MPP^+$ by the synaptic dopamine transporter. Blockers of this transporter prevent $MPP^+$ neurotoxicity. $MPP^+$ has been shown to be a relatively specific inhibitor of mitochondrial complex I activity, binding to complex I at the retenone binding site and impairing oxidative phosphorylation. In vivo studies have shown that MPTP can deplete striatal ATP concentrations in mice. It has been demonstrated that $MPP^+$ administered intrastriatally to rats produces significant depletion of ATP as well as increased lactate concentration confined to the striatum at the site of the injections. Compounds that enhance ATP production can protect against MPTP toxicity in mice.

A prodrug of Formula (I) is administered to animals such as mice or rats for three weeks before treatment with MPTP. MPTP is administered at an appropriate dose, dosing interval, and mode of administration for 1 week before sacrifice. Control groups receive either normal saline or MPTP hydrochloride alone. Following sacrifice the two striate are rapidly dissected and placed in chilled 0.1 M perchloric acid. Tissue is subsequently sonicated and aliquots analyzed for protein content using a fluorometer assay. Dopamine, 3,4-dihydroxyphenylacetic acid (DOPAC), and homovanillic acid (HVA) are also quantified. Concentrations of dopamine and metabolites are expressed as nmol/mg protein.

Prodrugs of Formula (I) that protect against DOPAC depletion induced by MPTP, HVA, and/or dopamine depletion are neuroprotective and therefore can be useful for the treatment of Parkinson's disease.

Haloperidol-Induced Hypolocomotion

The ability of a compound to reverse the behavioral depressant effects of dopamine antagonists such as haloperidol, in rodents and is considered a valid method for screening drugs with potential antiparkinsonian effects (Mandhane, et al., *Eur. J. Pharmacol.* 1997, 328, 135-141). Hence, the ability of prodrugs of Formula (I) to block haloperidol-induced deficits in locomotor activity in mice can be used to assess both in vivo and potential anti-Parkinsonian efficacy.

Mice used in the experiments are housed in a controlled environment and allowed to acclimatize before experimental use. One and one-half hours before testing, mice are administered 0.2 mg/kg haloperidol, a dose that reduces baseline locomotor activity by at least 50%. A test compound is administered 5-60 min prior to testing. The animals are then placed individually into clean, clear polycarbonate cages with a flat perforated lid. Horizontal locomotor activity is determined by placing the cages within a frame containing a 3×6 array of photocells interfaced to a computer to tabulate beam interrupts. Mice are left undisturbed to explore for 1 h, and the number of beam interruptions made during this period serves as an indicator of locomotor activity, which is compared with data for control animals for statistically significant differences.

6-Hydroxydopamine Animal Model

The neurochemical deficits seen in Parkinson's disease can be reproduced by local injection of the dopaminergic neurotoxin, 6-hydroxydopamine (6-OHDA) into brain regions containing either the cell bodies or axonal fibers of the nigrostriatal neurons. By unilaterally lesioning the nigrostriatal pathway on only one-side of the brain, a behavioral asymmetry in movement inhibition is observed. Although unilaterally-lesioned animals are still mobile and capable of self maintenance, the remaining dopamine-sensitive neurons on the lesioned side become supersensitive to stimulation. This is demonstrated by the observation that following systemic administration of dopamine agonists, such as apomorphine, animals show a pronounced rotation in a direction contralateral to the side of lesioning. The ability of compounds to induce contralateral rotations in 6-OHDA lesioned rats has been shown to be a sensitive model to predict drug efficacy in the treatment of Parkinson's disease.

Male Sprague-Dawley rats are housed in a controlled environment and allowed to acclimatize before experimental use. Fifteen minutes prior to surgery, animals are given an intraperitoneal injection of the noradrenergic uptake inhibitor desipramine (25 mg/kg) to prevent damage to nondopamine neurons. Animals are then placed in an anaesthetic chamber and anaesthetized using a mixture of oxygen and isoflurane. Once unconscious, the animals are transferred to a stereotaxic frame, where anesthesia is maintained through a mask. The top of the head of an animal is shaved and sterilized using an iodine solution. Once dry, a 2 cm long incision is made along the midline of the scalp and the skin retracted and clipped back to expose the skull. A small hole is then drilled through the skull above the injection site. In order to lesion the nigrostriatal pathway, the injection cannula is slowly lowered to position above the right medial forebrain bundle at −3.2 mm anterior posterior, −1.5 mm medial lateral from the bregma, and to a depth of 7.2 mm below the duramater. Two minutes after lowering the cannula, 6-OHDA is infused at a rate of 0.5 µL/min over 4 min, to provide a final dose of 8 µg. The cannula is left in place for an additional 5 min to facilitate diffusion before being slowly withdrawn. The skin is then sutured shut, the animal removed from the stereotaxic frame, and returned to its housing. The rats are allowed to recover from surgery for two weeks before behavioral testing.

Rotational behavior is measured using a rotameter system having stainless steel bowls (45 cm dia×15 cm high) enclosed in a transparent Plexiglas cover around the edge of the bowl and extending to a height of 29 cm. To assess rotation, rats are placed in a cloth jacket attached to a spring tether connected to an optical rotameter positioned above the bowl, which assesses movement to the left or right either as partial (45°) or full (360°) rotations.

To reduce stress during administration of a test compound, rats are initially habituated to the apparatus for 15 min on four consecutive days. On the test day, rats are given a test compound, e.g., a prodrug of Formula (I). Immediately prior to testing, animals are given a subcutaneous injection of a subthreshold dose of apomorphine, and then placed in the harness and the number of rotations recorded for one hour. The total number of full contralatral rotations during the hour test period serves as an index of antiparkinsonian drug efficacy.

Example 60

Use of Clinical Trials to Assess the Efficacy of α-Amino Acid Prodrugs for Treating Parkinson's Disease The following clinical study may be used to assess the efficacy of a compound in treating Parkinson's disease.

Patients with idiopathic PD fulfilling the Queen Square Brain Bank criteria (Gibb et al., *J Neurol Neurosurg Psychiatry* 1988, 51, 745-752) with motor fluctuations and a defined short duration GABA analog response (1.5-4 hours) are eligible for inclusion. Clinically relevant peak dose dyskinesias following each morning dose of their current medication are a further pre-requisite. Patients are also required to have been stable on a fixed dose of treatment for a period of at least one month prior to starting the study. Patients are excluded if their current drug regime includes slow-release formulations of L-Dopa, COMT inhibitors, selegiline, anticholinergic drugs, or other drugs that could potentially interfere with gastric absorption (e.g. antacids). Other exclusion criteria include patients with psychotic symptoms or those on antipsychotic treatment, patients with clinically relevant cognitive impairment, defined as MMS (Mini Mental State) score of less than 24 (Folstein et al., *J Psychiatr Res* 1975, 12, 189-198), risk of pregnancy, Hoehn & Yahr stage 5 in off-status, severe, unstable diabetes mellitus, and medical conditions such as unstable cardiovascular disease or moderate to severe renal or hepatic impairment. Full blood count, liver, and renal function blood tests are taken at baseline and after completion of the study.

A randomized, double blind, and cross-over study design is used. Each patient is randomized to the order in which either LD/DC or one of the two dosages of test compound, e.g., an α-amino acid prodrug, is administered in a single-dose challenge in double-dummy fashion in three consecutive sessions. Randomization is by computer generation of a treatment number, allocated to each patient according to the order of entry into the study. All patients give informed consent.

Patients are admitted to a hospital for an overnight stay prior to administration of test compound the next morning on three separate occasions at weekly intervals. After withdrawal of all antiparkinsonian medication from midnight the previous day, test compound is administered at exactly the same time in the morning in each patient under fasting conditions.

Patients are randomized to the order of the days on which they receive placebo or test compound. The pharmacokinetics of a test compound can be assessed by monitoring plasma α-amino acid concentration over time. Prior to administration, a 22 G intravenous catheter is inserted in a patient's forearm. Blood samples of 5 ml each are taken at baseline and 15, 30, 45, 60, 75, 90, 105, 120, 140, 160, 180, 210, and 240 minutes after administering a test compound or until a full off state has been reached if this occurs earlier than 240 minutes after drug ingestion. Samples are centrifuged immediately at the end of each assessment and stored deep frozen until assayed. Plasma α-amino acid levels are determined by high-pressure liquid chromatography (HPLC). On the last assessment additional blood may be drawn for routine hematology, blood sugar, liver, and renal function.

For clinical assessment, motor function is assessed using UPDRS (United Parkinson's Disease Rating Scale) motor score and BrainTest (Giovanni et al., *J Neurol Neurosurg Psychiatry* 1999, 67, 624-629), which is a tapping test performed with the patient's more affected hand on the keyboard of a laptop computer. These tests are carried out at baseline and then immediately following each blood sample until patients reach their full on-stage, and thereafter at 3 intervals of 20 min, and 30 min intervals until patients reach their baseline off-status. Once patients reach their full on-state, video recordings are performed three times at 20 min intervals. The following mental and motor tasks, which have been shown to increase dyskinesia (Duriff et al., *Mov Disord* 1999, 14, 242-245) are monitored during each video session: (1) sitting still for 1 minute; (2) performing mental calculations; (3) putting on and buttoning a coat; (4) picking up and drinking from a cup of water; and (5) walking. Videotapes are scored using, for example, versions of the Goetz Rating Scale and the Abnormal Involuntary Movements Scale to document a possible increase in test compound induced dyskinesia. Actual occurrence and severity of dyskinesia is measured with a Dyskinesia Monitor (Manson et al., *J Neurol Neurosurg Psychiatry* 2000, 68, 196-201). The device is taped to a patient's shoulder on their more affected side. The monitor records during the entire time of a challenging session and provides a measure of the frequency and severity of occurring dyskinesias.

Results can be analyzed using appropriate statistical methods.

Example 61

Animal Model for Assessing Therapeutic Efficacy of α-Amino Acid Prodrugs for Treating Alzheimer's Disease Heterozygous transgenic mice expressing the Swedish AD mutant gene, hAPPK670N, M671L (Tg2576; Hsiao, *Learning & Memory* 2001, 8, 301-308) are used as an animal model of Alzheimer's disease. Animals are housed under standard conditions with a 12:12 light/dark cycle and food and water available ad libitum. Beginning at 9 months of age, mice are divided into two groups. The first two groups of animals receive increasing doses of an α-amino acid prodrug, over six weeks. The remaining control group receives daily saline injections for six weeks.

Behavioral testing is performed at each drug dose using the same sequence over two weeks in all experimental groups: 1) spatial reversal learning, 2) locomotion, 3) fear conditioning, and 4) shock sensitivity. This order is selected to minimize interference among testing paradigms.

Acquisition of the spatial learning paradigm and reversal learning are tested during the first five days of test compound administration using a water T-maze as described in Bardgett et al., *Brain Res Bull* 2003, 60, 131-142. Mice are habituated to the water T-maze during days 1-3, and task acquisition begins on day 4. On day 4, mice are trained to find the escape platform in one choice arm of the maze until 6 to 8 correct choices are made on consecutive trails. The reversal learning phase is then conducted on day 5. During the reversal learning phase, mice are trained to find the escape platform in the choice arm opposite from the location of the escape platform on day 4. The same performance criterion and inter-trial interval are used as during task acquisition.

Large ambulatory movements are assessed to determine that the results of the spatial reversal learning paradigm are not influenced by the capacity for ambulation. After a rest period of two days, horizontal ambulatory movements, excluding vertical and fine motor movements, are assessed in a chamber equipped with a grid of motion-sensitive detectors on day 8. The number of movements accompanied by simultaneous blocking and unblocking of a detector in the horizontal dimension are measured during a one-hour period.

The capacity of an animal for contextual and cued memory is tested using a fear conditioning paradigm beginning on day 9. Testing takes place in a chamber that contains a piece of absorbent cotton soaked in an odor-emitting solution such as mint extract placed below the grid floor. A 5-min, 3 trial 80 db, 2800 Hz tone-foot shock sequence is administered to train the animals on day 9. On day 10, memory for context is tested by returning each mouse to the chamber without exposure to the tone and foot shock, and recording the presence or absence of freezing behavior every 10 seconds for 8 minutes. Freezing is defined as no movement, such as ambulation, sniffing or stereotypy, other than respiration.

On day 11, the response of an animal to an alternate context and to the auditory cue is tested. Coconut extract is placed in a cup and the 80 dB tone is presented, but no foot shock is delivered. The presence or absence of freezing in response to the alternate context is then determined during the first 2 minutes of the trial. The tone is then presented continuously for the remaining 8 minutes of the trial, and the presence or absence of freezing in response to the tone is determined.

On day 12, the animals are tested to assess their sensitivity to the conditioning stimulus, i.e., foot shock.

Following the last day of behavioral testing, animals are anesthetized and the brains removed, post-fixed overnight, and sections cut through the hippocampus. The sections are stained to image β-amyloid plaques (see e.g., Dong et al., *Neuroscience* 2004, 127, 601-609).

Data are analyzed using appropriate statistical methods.

Example 62

Animal Model for Assessing Therapeutic Efficacy of α-Amino Acid Prodrugs for Treating Huntington's Disease Neuroprotective Effects in a Transgenic Mouse Model of Huntington's Disease Transgenic HD mice of the N171-82Q strain and non-transgenic littermates are treated with a prodrug of Formula (I) or a vehicle from 10 weeks of age. The mice are placed on a rotating rod ("rotarod"). The length of time at which a mouse falls from the rotarod is recorded as a measure of motor coordination. The total distance traveled by a mouse is also recorded as a measure of overall locomotion. Mice administered prodrugs of Formula (I) that are neuroprotective in the N171-82Q transgenic HD mouse model remain on the rotarod for a longer period of time and travel further than mice administered vehicle.

Malonate Model of Huntington's Disease

A series of reversible and irreversible inhibitors of enzymes involved in energy generating pathways has been used to generate animal models for neurodegenerative diseases such as Parkinson's and Huntington's diseases. In particular, inhibitors of succinate dehydrogenase, an enzyme that impacts cellular energy homeostasis, has been used to generate a model for Huntington's disease (Brouillet et al., *J. Neurochem.* 1993, 60, 356-359; Beal et al., *J. Neurosci.* 1993, 13, 4181-4192; Henshaw et al., *Brain Research* 1994, 647, 161-166; and Beal et al., *J. Neurochem.* 1993, 61, 1147-1150). The enzyme succinate dehydrogenase plays a central role in both the tricarboxylic acid cycle as well as the electron transport chain in mitochondria. Malonate is a reversible inhibitor of succinate dehydrogenase. Intrastriatal injections of malonate in rats have been shown to produce dose dependent striatal excitotoxic lesions that are attenuated by both competitive and noncompetitive NMDA antagonists (Henshaw et al., *Brain Research* 1994, 647, 161-166). For example, the glutamate release inhibitor, lamotrigine, also attenuates the lesions. Co-injection with succinate blocks the lesions, consistent with an effect on succinate dehydrogenase. The lesions are accompanied by a significant reduction in ATP levels as well as a significant increase in lactate levels in vivo as shown by chemical shift resonance imaging (Beal et al., *J. Neurochem.* 1993, 61, 1147-1150). The lesions produce the same pattern of cellular sparing, which is seen in Huntington's disease, supporting malonate challenge as a useful model for the neuropathologic and neurochemical features of Huntington's disease.

To evaluate the effect of α-amino acid prodrugs of Formula (I) in this malonate model for Huntington's disease, a prodrug of Formula (I) is administered at an appropriate dose, dosing interval, and route, to male Sprague-Dawley rats. A prodrug is administered for two weeks prior to the administration of malonate and then for an additional week prior to sacrifice. Malonate is dissolved in distilled deionized water and the pH adjusted to 7.4 with 0.1 M HCl. Intrastriatal injections of 1.5 μL of 3 μmol malonate g are made into the left striatum at the level of the Bregma 2.4 mm lateral to the midline and 4.5 mm ventral to the dura. Animals are sacrificed at 7 days by decapitation and the brains quickly removed and placed in ice cold 0.9% saline solution. Brains are sectioned at 2 mm intervals in a brain mold. Slices are then placed posterior side down in 2% 2,3,5-triphenyltetrazolium chloride. Slices are stained in the dark at room temperature for 30 min and then removed and placed in 4% paraformaldehyde pH 7.3. Lesions, noted by pale staining, are evaluated on the posterior surface of each section. The measurements are validated by comparison with measurements obtained on adjacent Nissl stain sections. Compounds exhibiting a neuroprotective effect and therefore potentially useful in treating Huntington's disease show a reduction in malonate-induced lesions.

Example 63

Animal Models of Pain

Inflammatory Pain—Formalin Test

A formalin assessment test is performed according to the procedure described by Dubuisson and Dennis, *Pain* 1977, 4, 161-174. Fifty μL of a 5% formalin solution is injected subcutaneously into the dorsal aspect of the right hind paw and the rats are then individually placed into clear observation cages. Rats are observed for a continuous period of 60 min or for periods of time corresponding to phase I (from 0 to 10 min following formalin injection) and phase II (from 30 to 50 min following formalin injection) of the formalin test (Abbott et al., *Pain* 1995, 60, 91-102). The number of flinching behaviors of the injected paw is recorded using a sampling technique in which each animal is observed for one 60-sec period during each 5-min interval. Test compound is administered 30 min or other appropriate interval prior to formalin injection.

Inflammatory Pain—Carrageenan-Induced Acute Thermal Hyperalgesia and Edema

Paw edema and acute thermal hyperalgesia are induced by injecting 100 μL of a 1% solution of λ-carrageenan in physiological saline into the plantar surface of the right hind paw. Thermal hyperalgesia is determined 2 h following carrageenan injection, using a thermal paw stimulator as described by Hargreaves et al., *Pain* 1988, 32, 77-88. Rats are placed into plastic cubicles mounted on a glass surface maintained at 30° C. and a thermal stimulus in the form of radiant heat emitted from a focused projection bulb is then applied to the plantar surface of each hind paw. The stimulus current is maintained at 4.50±0.05 Amp, and the maximum time of exposure is set at 20.48 sec to limit possible tissue damage. The elapsed time until a brisk withdrawal of the hind paw from the thermal stimulus is recorded automatically using photodiode motion sensors. The right and left hind paw of each rat is tested in three sequential trials at about 5-min intervals. Carrageenan-induced thermal hyperalgesia of paw withdrawal latency ($PWL_{thermal}$) is calculated as the mean of the two shortest latencies. Test compound is administered 30 min before assessment of thermal hyperalgesia.

The volume of paw edema is measured using water displacement with a plethysmometer 2 h following carrageenan injection by submerging the paw up to the ankle hairline (approx. 1.5 cm). The displacement of the volume is measured by a transducer and recorded. Test compound is administered at an appropriate time following carrageenan injection, such as for example, 30 min or 90 min.

Visceral Pain

Thirty min following administration of test compound, mice receive an injection of 0.6% acetic acid in sterile water (10 mL/kg, i.p.) as described by Mogil et al., *Pain* 1999, 80, 67-82. Mice are then placed in table-top Plexiglass observation cylinders (60 cm high×40 cm diameter) and the number of constrictions/writhes (a wave of mild constriction and elongation passing caudally along the abdominal wall, accompanied by a slight twisting of the trunk and followed by bilateral extension of the hind limbs) is recorded during the 5-20 min following acetic acid injection for a continuous observation period of 15 min.

Neuropathic Pain—Spinal Nerve Ligation

Rats receive unilateral ligation of the lumbar 5 (L5) and lumbar 6 (L6) spinal nerves as described by Kim and Chung, *Pain* 1992, 50, 355-363. The left L5 and L6 spinal nerves of the rat are isolated adjacent to the vertebral column and tightly ligated with a 5-0 silk suture distal to the dorsal root ganglia, and care is taken to avoid injury of the lumbar 4 (L4) spinal nerve. Control rats undergo the same procedure but without nerve ligation. All animals are allowed to recover for at least 1 week and not more than 3 weeks prior to assessment of mechanical allodynia. Mechanical allodynia is measure using calibrated von Frey filaments as described by Chaplan et al., *J Neurosci Methods* 1994, 53, 55-63. Rats are placed into inverted plastic containers (20×12.5×20 cm) on top of a suspended wire mesh grid and acclimated to the test chamber for 20 min. The von Frey filaments are presented perpendicularly to the plantar surface of the selected hind paw, and then held in this position for approximately 8 s with enough force to cause a slight bend in the filament. Positive responses include an abrupt withdrawal of the hind paw from the stimulus or flinching behavior immediately following removal of the stimulus. A 50% paw withdrawal threshold (PWT) is determined using the procedure described by Dixon, *Rev Pharmacol Toxicol* 1980, 20, 441-462. Rats with a PWT≦5.0 g are considered allodynic and utilized to test the analgesic activity of a test compound. The test compound can be administered 30 min prior to the assessment of mechanical allodynia.

Neuropathic Pain—Chronic Constriction Injury of the Sciatic Nerve

A model of chronic constriction injury of the sciatic nerve-induced neuropathic pain according to the method of Bennett and Xie, *Pain* 1988, 33, 87-107, is used. The right common sciatic nerve is isolated at mid-thigh level and loosely ligated by four chromic gut (4-0) ties separated by an interval of 1 mm. Control rats undergo the same procedure but without sciatic nerve constriction. All animals are allowed to recover for at least 2 weeks and for no more than 5 weeks prior to testing of mechanical allodynia. Allodynic PWT is assessed in the animals as described for animals with spinal nerve ligation. Only rats with a PWT≦5.0 g are considered allodynic and utilized to evaluate the analgesic activity of a test compound. Test compound is administered 30 min or other appropriate time prior to the assessment of mechanical allodynia.

Neuropathic Pain—Vincristine-Induced Mechanical Allodynia

A model of chemotherapy-induced neuropathic pain is produced by continuous intravenous vincristine infusion (Nozaki-Taguchi et al., *Pain* 20.01, 93, 69-76). Anesthetized rats undergo a surgical procedure in which the jugular vein is catheterized and a vincristine-primed pump is implanted subcutaneously. Fourteen days of intravenous infusion of vincristine (30 μg/kg/day) results in systemic neuropathic pain of the animal. Control animals undergo the same surgical procedure, with physiological saline infusion. PWT of the left paw is assessed in the animals 14 days post-implantation as described for the spinal nerve ligation model. Test compound is administered 30 min prior to the test for mechanical allodynia in rats with PWT≦5.00 g before treatment.

Post-Operative Pain

A model of post-operative pain is performed in rats as described by Brennan et al., *Pain* 1996, 64, 493-501. The plantar aspect of the left hind paw is exposed through a hole in a sterile plastic drape, and a 1-cm longitudinal incision is made through the skin and fascia, starting 0.5 cm from the proximal edge of the heel and extending towards the toes. The plantaris muscle is elevated and incised longitudinally leaving the muscle origin and insertion points intact. After hemostasis by application of gently pressure, the skin is opposed with two mattress sutures using 5-0 nylon. Animals are then allowed to recover for 2 h following surgery, at which time mechanical allodynia and thermal hyperalgesia are assessed.

Effects of test compound on mechanical allodynia are assessed 30 min following administration, with PWT being examined in these animals for both the injured and non-injured paw as described for the spinal nerve ligation model with the von Frey filament systematically pointing towards the medial side of the incision. In a separate experiment, the effects of test compound on thermal hyperalgesia are assessed 30 min following administration of test compound, with $PWL_{thermal}$ being determined as described for the carrageenin-induced thermal hyperalgesia model with the thermal stimulus applied to the center of the incision of the paw planter aspect.

Example 64

Animal Models to Assess the Efficacy of α-Amino Acid Prodrugs for Treating Social Phobia Fear-Potentiated Startle Model The fear-potentiated startle paradigm, e.g., increased startle in the presence of a conditioned fear stimulus (CFS), is a learned fear paradigm that has been shown to involve the central amygdala (see, e.g., Davis, *Behav. Neurosci.* 1986, 100, 814-824; and Helton et al., *J. Pharmacol. Exp. Ther* 1998, 284, 651-660). Fear potentiated startle evokes a neurological process that mimics the behavioral pathology manifest in post-traumatic stress disorder and other anxiety-based diseases. Elevated anxiety impairs sensory processing with consequent deterioration of memory, cognition, and social function. Anxiogenic states seen in human conditions such as generalized social phobia (Stein et al., *Arch. Gen. Psychiatry* 2002, 59, 1027-1034) or drug-induced animal models of anxiety (Sanders and Shekhar, *Pharmacol. Biochem. Behav.* 1995, 52, 701-706) are accompanied by abnormal amygdala function. Human studies have demonstrated that both the baseline and fear-potentiated responses can be inhibited by anxiolytic drugs such as the benzodiazepine, alprazolam (Riba et al., *Psychopharmacology (Berl)* 2001, 157, 358-367). Measures of fear-potentiated startle response in rats and humans provide a good indication for the potential anxiolytic activity of a drug (see e.g., Belzung, *Current Opinion in Investigational Drugs.* 2001, 2(8), 1108-1111; and Nestler et al., *Neuron*, 2002, 34, 13-25). Thus, these known models can be used to confirm the efficacy of one or more compounds of Formula (I) as therapies for affective disorders.

Male Sprague-Dawley rats weighing 350-450 g are used. Animals are maintained on a 12:12 hour light-dark cycle with food and water continuously available. Animals are trained and tested in 8×15×15 $cm^3$ Plexiglas™ and wire-mesh cages. Each cage floor consists of four 6 mm diameter stainless-steel bars spaced 18 mm apart. Each cage is suspended between compression springs within a steel frame and located within a 90×70×70 $cm^3$ ventilated sound-attenuating chamber. Background noise (60 dB wide-band) is provided by a noise generator and delivered through high-frequency speakers located 5 cm in front of each cage. Sound level measurements (sound pressure level) are made with a sound-level meter (A scale; random input) with a microphone located 7 cm from the center of the speaker (approximating the distance of the rat's ear from the speaker).

Startle responses are evoked by 50 msec, 95 dB white noise bursts (5 msec rise-decay) delivered through the same speakers used to provide background noise. An accelerometer affixed to the bottom of each cage produces a voltage output proportional to the velocity of cage movement. This output is amplified and digitized. Startle amplitude is defined as the maximal peak-to-peak voltage that occurs during the first 200 msec after onset of the startle-eliciting stimulus.

The conditioned stimulus (CS) is a 3.7 sec light (80 lux) produced by an 8 W fluorescent bulb (100 msec rise time) located 10 cm behind each cage. Luminosity is measured using a light meter. The US is a 0.5 second shock, delivered to the floorbars and produced by a shock generator. Shock intensities (measured as in, for example, Cassella et al., *Physiol Behav* 1986, 36, 1187-91) are 0.4 mA.

Test compounds are administered prior to evaluation. To match the animals for assessment, on each of the next 2 days animals are placed in the test chambers and presented with 30 95 dB noise bursts at a 30 sec interstimulus interval (ISI). The mean startle amplitude across the 30 stimuli on the second day is used to divide rats into groups with similar startle amplitudes.

To fear condition the test animals, on each of the next 2 days, rats are returned to the test chambers and 5 min later given the first of 10 light-footshock pairings. The 0.4 mA 0.5 sec shock is delivered during the last 0.5 sec of the 3.7 sec light. The average intertrial interval (ITI) is 4 min (range, 3-5 min).

Twenty-four (24) hours after the last fear conditioning session, test compound or vehicle is administered to the rats and the rats are immediately placed into the test chambers. After 5 min the rats receive 30 95 dB noise bursts (30 sec ISI) to habituate the startle response to a stable baseline prior to the test trials. Each test trial (18 total) involves the presentation of a noise burst of one of 3 intensities (95, 100, or 105 dB); half of these occurring in the presence and half in the absence of the light CS. On the CS trials the startle stimulus is presented 3.2 sec after the onset of the 3.7 sec light. Trial types are presented in a balanced, irregular order (30 sec ITI) with the restriction that each of the 6 trial types occur once within each of the 3 trial blocks.

The initial startle stimuli of the test session are used to habituate startle responses to asymptotic levels and are not included in statistical analyses. Subsequent startle responses generated by the three different startle intensities are averaged for each animal to obtain a single score for both the startle stimulus alone (baseline) and the CS and startle stimulus trials. A difference score is computed for each animal by subtracting the mean baseline startle amplitudes from the mean startle amplitudes in the presence of the CS. Analysis of the data is performed using appropriate statistical methods.

Activity and Functional Observation Measurements

Rats are dosed with vehicle or test compound from postnatal day 25 to post natal day 70. The locomotor activity of 10 randomly selected rats/sex/group is measured on postnatal day 30 (adolescent) and postnatal day 72 (adult). On postnatal day 30 and postnatal day 72, each rat is placed in a shoebox cage equipped with the automated Photobeam Activity System. Locomotor activity is monitored during a 60 min session composed of 12, 5-min intervals. The total number of photobeam breaks that occur during each of the 12, 5-min intervals is recorded. Changes in habituation to novel environments are assessed by comparing locomotor activity over 3 session intervals between the control versus test groups for habituation. Emotionality is determined by following behavioral facets including defecation, urination, rearing, grooming, and backing (see e.g., Hall, *J. Comp. Physiol. Psychol.*, 1936, 22, 325-352; and Spyker, in Behavioral Toxicology, Ed. Weiss and Laties, Plenum Press, New York, pp 311-349, 1975). A functional observation battery is performed on postnatal day 75 according to the parameters described by Irwin, *Psychopharmacologia* 1968, 13, 222-257, to evaluate gait, posture, abnormal behavior, and vocalization.

Spatial Navigation in an M Swim Maze

Drugs with anxiolytic or anti-depression activity often demonstrate unwanted side-effects, such as sedation, amnesia or other cognitive impairment, hyperactivity, or hypoactivity. A standard test for these unwanted side-effects is to quantify activity and emotionality to a novel surrounding in rats after repeated exposure to drug. An additional test to measure effects of a drug on aspects of learning and memory is the M Swim Maze.

The M Swim Maze was developed to test spatial learning and memory (e.g., functional memory). The animal has no visual or spatial cues in the pool and must rely on extra-maze cues (e.g., light setup outside the pool that can be seen by the swimming animal). Through a series of trials a rat develops "place learning" or knowledge about the position of the escape platform based upon the extra-maze cues. The platform can be moved to a different arm of the M configuration each day, combining spatial memory with working memory. This paradigm involves extinction of the prior memory and resolution of a new spatial problem. Many drugs that have anxiolytic or anti-depressive effects have detrimental effects on functional memory important for daily life. Additionally, spatial learning and memory tasks in rodents during stressful activities, such as escape from water, are useful to evaluate drugs for unwanted side effects of impairment of functional memory. Results in rodents correlate well to those in humans and other mammals. Decreased performance in this model indicates a negative locomotor or cognitive side-effect of drug treatment. An improvement may indicate improved cognition due to reduced stress or anxiety from task performance.

As an example, vehicle or test compound is administered to rats on postnatal day 25 through postnatal day 70 (45 days). Learning and memory are evaluated in a water M-maze. The evaluation consists of 10 trials/day for each animal on 4 successive days to assess short-term memory. The animals are evaluated for their ability to escape from the maze via a platform located on the lighted arm of an M-shaped maze. After placement of the animal in the central arm of the M-shaped maze, the goal side is varied for each animal at each trial according to a predetermined computer generated sequence. The same animals are also tested 5 days after the initial testing to assess long-term memory. On that day each animal is allowed 10 trials in the maze and time to escape is measured. Analysis of the data is performed using appropriate statistical analysis methods.

Social Interaction Test

The Social Interaction Test is another test that can be used to assess anxiolytic properties (see e.g., File and Hyde, *Pharmacol Biochem Behav* 1979, Jul. 11(1), 65-69).

Rats are allowed to acclimate to the animal care facility for 5 days and are housed singly for 5 days prior to testing with free access to food and water. Animals are handled for 5 min per day. The design and procedure for the Social Interaction Test can be performed as described by Kennett et al., *Neuropharmacology* 1997, 36(4-5), 601-608). On the test day, weight matched pairs of rats, unfamiliar to each other, are given identical treatments and returned to their home cages. Animals are randomly divided into treatment groups and are administered test compound, vehicle, or chlordiazepoxide (5 mg/kg). Dosing is at least 1 hr prior to testing. Rats are subsequently placed in a white Perspex test box or arena (54×37×26 cm³) in which the floor is divided up into 24 equal squares, for 15 min. Background noise is applied. Sessions are videotaped. Active social interaction, defined as time involved in grooming, sniffing, biting, boxing, wrestling, following, and crawling over or under, is scored. The number of episodes of rearing (animal completely rises up its body on its hind limbs), grooming (licking, biting, scratching of body), and face washing (i.e., hands are moved repeatedly over face), and number of squares crossed are scored. Passive social interaction (animals lying beside or on top of each other) is not scored. The social interaction data is analyzed by appropriate statistical methods.

Finally, it should be noted that there are alternative ways of implementing the embodiments disclosed herein. Accordingly, the present embodiments are to be considered as illustrative and not restrictive, and the claims are not to be limited to the details given herein, but may be modified within the scope and equivalents thereof.

What is claimed is:

1. A compound of Formula (I):

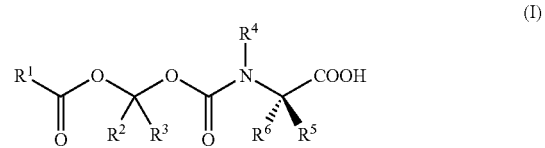

or a pharmaceutically acceptable salt of any of the foregoing, wherein:

$R^1$ is chosen from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^2$ and $R^3$ are independently chosen from hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl, and substituted heteroarylalkyl; or $R^2$ and $R^3$ together with the carbon atom to which they are bonded form a ring chosen from a cycloalkyl, substituted cycloalkyl, cycloheteroalkyl, and substituted cycloheteroalkyl ring;

$R^4$ is chosen from hydrogen and methyl;

$R^5$ and $R^6$ together with the carbon atom to which they are bonded form a ring chosen from a 1,1-cyclopropane ring and a substituted 1,1-cyclopropane ring.

2. The compound of claim 1, wherein $R^1$ is chosen from $C_{2-4}$ alkyl, phenyl, substituted phenyl, cyclohexyl, and substituted cyclohexyl; $R^2$ is chosen from hydrogen, and $C_{1-4}$ alkyl; and $R^3$ is hydrogen.

3. The compound of claim 1, wherein $R^4$ is hydrogen.

4. The compound of claim 3, wherein $R^1$ is chosen from $C_{1-6}$ alkyl, phenyl, substituted phenyl, cyclohexyl, substituted cyclohexyl, $C_{7-9}$ phenylalkyl, and adamantyl; $R^2$ is chosen from hydrogen and $C_{1-4}$ alkyl; and $R^3$ is hydrogen.

5. The compound of claim 1, wherein $R^1$ is chosen from $C_{1-6}$ alkyl, substituted $C_{1-6}$ alkyl, $C_{6-10}$ aryl, substituted $C_{6-10}$ aryl, $C_{3-7}$ cycloalkyl, substituted $C_{3-7}$ cycloalkyl, $C_{6-10}$ arylalkyl, and $C_{6-10}$ substituted arylalkyl.

6. The compound of claim 1, wherein $R^1$ is chosen from $C_{1-4}$ alkyl, phenyl, substituted phenyl, cyclohexyl, substituted cyclohexyl, styryl, and substituted styryl.

7. The compound of claim 1, wherein $R^1$ is chosen from methyl, ethyl, n-propyl, isopropyl, n-butyl, isobutyl, sec-butyl, tert-butyl, phenyl, o-tolyl, cyclohexyl, and styryl.

8. The compound of claim 1, wherein the substituents of each substituted group are each independently chosen from halogen, $C_{1-3}$ alkyl, —OH, —$NH_2$, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino.

9. The compound of claim 1, wherein $R^2$ and $R^3$ are independently chosen from hydrogen, $C_{1-6}$ alkyl, substituted $C_{1-6}$ alkyl, $C_{6-10}$ aryl, substituted $C_{6-10}$ aryl, $C_{3-7}$ cycloalkyl, and substituted $C_{3-7}$ cycloalkyl.

10. The compound of claim 1, wherein $R^2$ and $R^3$ are independently chosen from hydrogen, methyl, ethyl, n-propyl, isopropyl, phenyl, and cyclohexyl.

11. The compound of claim 1, wherein $R^2$ is hydrogen; and $R^3$ is chosen from hydrogen, methyl, ethyl, n-propyl, isopropyl, phenyl, and cyclohexyl.

12. The compound of claim 1, wherein $R^1$ is chosen from $C_{1-6}$ alkyl, substituted $C_{1-6}$ alkyl, $C_{6-10}$ aryl, substituted $C_{6-10}$ aryl, $C_{3-7}$ cycloalkyl, substituted $C_{3-7}$ cycloalkyl, $C_{6-10}$ arylalkyl, and $C_{6-10}$ substituted arylalkyl; and $R^2$ and $R^3$ are independently chosen from hydrogen, $C_{1-6}$ alkyl, substituted $C_{1-6}$ alkyl, $C_{6-10}$ aryl, substituted $C_{6-10}$ aryl, $C_{3-7}$ cycloalkyl, and substituted $C_{3-7}$ cycloalkyl.

13. The compound of claim 1, wherein $R^1$ is chosen from methyl, ethyl, n-propyl, isopropyl, n-butyl, isobutyl, sec-butyl, tert-butyl, phenyl, o-tolyl, cyclohexyl, and styryl; $R^2$ is hydrogen; and $R^3$ is chosen from hydrogen, methyl, ethyl, n-propyl, isopropyl, phenyl, and cyclohexyl.

14. A pharmaceutical composition comprising at least one pharmaceutically acceptable vehicle and at least one compound of claim 1.

15. The pharmaceutical composition of claim 14, wherein the pharmaceutical composition is formulated for oral administration.

16. The pharmaceutical composition of claim 15, wherein the pharmaceutical composition is a sustained release oral formulation.

17. The pharmaceutical composition of claim 14, wherein the at least one compound of Formula (I) is present in an amount effective for the treatment of a disease in a patient, wherein the disease is chosen from post-partum depression, premenstrual syndrome, premenstrual dysphoric disorder, a learning disorder, autistic disorder, attention-deficit hyperactivity disorder, Tourette's syndrome, phobia, post-traumatic stress disorder, dementia, AIDS dementia, Alzheimer's disease, Parkinson's disease, Huntington's disease, spasticity, myoclonus, muscle spasm, depression, anxiety, bipolar disorder, a substance abuse disorder, and urinary incontinence.

18. The pharmaceutical composition of claim 14, wherein the disease is schizophrenia.

19. A method of treating a disease in a patient, wherein the disease is chosen from post-partum depression, premenstrual syndrome, premenstrual dysphoric disorder, a learning disorder, autistic disorder, attention-deficit hyperactivity disorder, Tourette's syndrome, phobia, post-traumatic stress disorder, dementia, AIDS dementia, Alzheimer's disease, Parkinson's disease, Huntington's disease, spasticity, myoclonus, muscle spasm, depression, anxiety, bipolar disorder, a substance abuse disorder, and urinary incontinence, comprising administering to a patient in need of such treatment a pharmaceutical composition comprising a therapeutically effective amount of at least one compound of claim 1 and at least one pharmaceutically acceptable vehicle.

20. The method of claim 19, wherein the disease is schizophrenia.

21. The method of claim 19, wherein the pharmaceutical composition is a sustained release oral dosage form.

22. The method of claim 19, wherein the pharmaceutical composition is administered to the patient once or twice per day.

23. The method of claim 19, comprising administering a therapeutically effective amount of at least one additional therapeutic agent.

24. The method of claim 23, wherein the at least one additional therapeutic agent is chosen from an antipsychotic, an antidepressant, an anxiolytic, an anti-anxiety agent, a sedative, and a hypnotic.

* * * * *